(12) United States Patent
Riback et al.

(10) Patent No.: US 9,533,097 B2
(45) Date of Patent: Jan. 3, 2017

(54) APPARATUS AND METHOD FOR PROCESSING A SET OF DATA VALUES

(75) Inventors: Jacob Lars Fredrik Riback, Taeby (SE); Michael Kjell Ljuhs, Solna (SE); Lars Gustaf Liljeryd, Stockholm (SE)

(73) Assignee: DIABETES TOOLS SWEDEN AB (SE)

(*) Notice: Subject to any disclaimer, the term of this patent is extended or adjusted under 35 U.S.C. 154(b) by 1129 days.

(21) Appl. No.: 13/370,653

(22) Filed: Feb. 10, 2012

(65) Prior Publication Data

US 2012/0209091 A1  Aug. 16, 2012

Related U.S. Application Data

(63) Continuation of application No. PCT/EP2010/061640, filed on Aug. 10, 2010.
(Continued)

(51) Int. Cl.
*G01N 33/48* (2006.01)
*G01N 31/00* (2006.01)
(Continued)

(52) U.S. Cl.
CPC ........ *A61M 5/1723* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS 6,135,966 A    10/2000  Ko
6,923,763 B1   8/2005   Kovatchev et al.
(Continued)

FOREIGN PATENT DOCUMENTS

CN    1192273    9/1998
CN    1192665    9/1998
(Continued)

OTHER PUBLICATIONS

Kovatchev, et al., "Symmetrization of the Blood Glucose Measurement Scale and Its Applications", Diabetes Care, Clinical Care/Education/Nutrition, vol. 20, No. 11, Nov. 1997, pp. 1655-1658.
(Continued)

*Primary Examiner* — Larry D Riggs, II
(74) *Attorney, Agent, or Firm* — Condo Roccia Koptiw LLP

(57) ABSTRACT

An apparatus for processing a set of data values, a data value representing a physiological measure of a body fluid at a time instant, comprising: an estimated probability function calculator for calculating an estimated probability function associated with the set of data values; a transform calculator for calculating a non-linear transform rule using a predetermined target probability function being different from the estimated probability function, so that the probability function of a set of transform data values is closer to the target probability function than the estimated probability function; and a transformer for applying the transform rule to the set of data values or to at least one further data value not included in the set of data values and sampled at the different time instant from the time instants for the set of data values to obtain at least one transformed value representing the physiological measure.

13 Claims, 36 Drawing Sheets

Related U.S. Application Data

(60) Provisional application No. 61/232,697, filed on Aug. 10, 2009.

(51) Int. Cl.
*G06G 7/48* (2006.01)
*G06G 7/58* (2006.01)
*A61M 5/172* (2006.01)
*A61B 5/145* (2006.01)
*A61B 5/00* (2006.01)
*G06F 19/00* (2011.01)

(52) U.S. Cl.
CPC ........ *G06F 19/345* (2013.01); *G06F 19/3437* (2013.01); *G06F 19/3456* (2013.01); *A61M 2230/005* (2013.01); *A61M 2230/201* (2013.01); *G06F 19/322* (2013.01)

(56) References Cited

U.S. PATENT DOCUMENTS

| | | |
|---|---|---|
| 2003/0212317 A1 | 11/2003 | Kovatchev et al. |
| 2005/0027180 A1 | 2/2005 | Goode, Jr. et al. |
| 2005/0214892 A1 | 9/2005 | Kovatchev et al. |
| 2008/0033254 A1 | 2/2008 | Kamath et al. |

FOREIGN PATENT DOCUMENTS

| | | |
|---|---|---|
| CN | 1117331 | 8/2003 |
| CN | 1622785 | 6/2005 |
| CN | 1325015 | 7/2007 |
| CN | 101079082 | 11/2007 |
| CN | 100515335 | 7/2009 |
| CN | 101488162 | 7/2009 |
| EP | 1728469 | 12/2006 |
| EP | 1956371 | 8/2008 |
| JP | 2002541883 | 12/2002 |
| JP | 2004-514493 | 5/2004 |
| JP | 2007-14751 | 1/2007 |
| JP | 2007-501028 | 1/2007 |
| JP | 2008194452 | 8/2008 |
| WO | WO-96/39926 | 12/1996 |
| WO | WO-96/41151 | 12/1996 |
| WO | WO-0049941 | 8/2000 |
| WO | WO-02/43583 | 6/2002 |
| WO | WO-02/065090 | 8/2002 |
| WO | WO-03/063699 | 8/2003 |
| WO | WO-2005/011489 | 2/2005 |
| WO | WO-2008/052199 | 5/2008 |
| WO | WO-2008/085309 | 7/2008 |
| WO | WO-2008/141306 | 11/2008 |

OTHER PUBLICATIONS

Norman, et al., "Biostatistics: The Bare Essentials", People's Medical Publishing House, Shelton, Dec. 2008, p. 173.

x : small ⟶ - influence of log. characteristic is high
- influence of linear characteristic is low
(but not zero)

x : high ⟶ - influence of log. characteristic is low
(but not zero)
- influence of linear characteristic is high

APPARATUS AND METHOD FOR PROCESSING A SET OF DATA VALUES

CROSS-REFERENCE TO RELATED APPLICATIONS

This application is a continuation of copending International Application No. PCT/EP2010/061640, filed Aug. 10, 2010, and additionally claims priority from U.S. Application No. 61/232,697, filed Aug. 10, 2009, all of which are incorporated herein by reference in their entirety.

The present invention relates to medical instruments and systems for monitoring, displaying, controlling and interpreting data typically extracted from bodily fluid analytes of mammalians.

BACKGROUND OF THE INVENTION

Diabetes mellitus (DM) is the common name for a series of metabolic disorders caused mainly by defects in the glucose regulatory system leading to a partial or total destruction of the insulin producing beta cells. Insulin resistance, insufficient amount or total loss of insulin, reduce or inhibit counter regulatory means to achieve glucose homeostasis. Impaired glucose regulation is reflected in elevated glucose levels and glucose fluctuations.

Elevated levels of glucose, hyperglycemia, gradually induce or increase the risk of developing diabetic micro- and macrovascular complications. Long term risk and complications increase approximately exponentially in relation to a glucose mean level. Microvascular complications include neuropathy (nerve damage), nephropathy (kidney disease) and vision disorders (e.g. retinopathy, glaucoma, cataract and corneal disease). Macrovascular complications include heart disease, stroke and peripheral vascular disease (which can lead to ulcers, gangrene and amputation). Additionally, other complications include infections, metabolic difficulties, impotence, autonomic neuropathy and pregnancy problems.

The objective of DM treatment is to continuously maintain the concentration of blood glucose close to normoglycemia. This means staying below hyperglycemic levels but above the critical concentration level at which the amount of glucose is not sufficient for vital energy supply, hypoglycemia. When the glucose concentration is too low, symptoms like unconsciousness, confusion or seizure that preclude self-treatment set in. Recurring severe hypoglycemic events increase the risk of brain damage.

For patients with diabetes, self-management is a lifelong struggle trying to achieve treatment targets while balancing between the short term risk of hypoglycemia and the risk of long-term medical complications due to hyperglycemia. The dynamics and complexity of DM with multiple influencing factors, in combination with insufficient options for treatment, make successful therapy a difficult challenge. For example, in Sweden, (known for its good health care), only approximately 50% of the diabetic patients reach treatment targets.

Apart from insulin regimens, DM treatment primarily relies upon behavioral dietary adjustments, lifestyle management and/or anti-diabetic drug therapy. The latter generally becomes necessary as the disease progresses, and may be treated by a variety of drugs. The most common drugs are oral agents, like metformin that increases sensitivity to insulin and sulfonylurea that stimulates the pancreas to produce more insulin. Insulin on the other hand acts on cells to stimulate uptake, utilization and storage of glucose.

Regardless of DM type, treatment targets and strategies are based on glucometer readings either from sparsely sampled finger pricking using self-monitoring of blood glucose (SMBG) or by densely sampled continuous glucose monitoring (CGM).

Using a glucometer is the most common method for quantifying the concentration of blood glucose. The frequency of measurements varies widely among individuals depending on type and progression of the disease, motivation, treatment regime and other circumstances. FBG (fasting blood glucose), pre-prandial (before meal) and post prandial (after meal) blood glucose measurements are practiced in modern intensive treatment of diabetes. In general, more daily measurements allow better control and less glucose variability.

In CGM a disposable glucose sensor is inserted subcutaneously and determines the blood glucose level continuously until sensor replacement is needed after a few days. While CGM has proven useful, its use is still limited, partly due to high costs, accuracy and reliability issues. In addition, CGM technology forms the basis for closed loop artificial pancreas research and involves connecting an insulin pump to the CGM using a controller.

Presentation of glycemic data can be found in hand-held measuring devices, medical device displays and diabetes software for computers, smart phones etc. Many glucometers only display blood glucose values as discrete digits while some graphically display glucose levels that enable monitoring of blood glucose changes and trends over time. Advanced glucometers, CGM and software for diabetes data analysis sometimes display data in one-dimensional bar-graphs or thermometer-type displays or two-dimensional diagrams where the Y-axis represent a glucose-level with a linear range and the X-axis represent time. Moreover, standard statistical measures including the arithmetic mean value, standard deviation, coefficient of variation, min and max values are usually applied on glucose readings over different time ranges and time segments in diabetes software. The glucose readings are the only feedback available to the user to assess and evaluate the effects of treatment regimens.

Despite pharmaceutical and technical advances in treatment of diabetes the means to reach satisfactory blood glucose levels are neither adequate nor sufficient. The complexity of glucose dynamics requires the patient to develop an understanding of causality in order to act proactive instead of reactive. Treatment feedback from typical instruments and tools exhibit serious limitations that hampers understanding of the problems involved in the control of diabetes.

Current tools and methods used for presentation and interpretation of blood glucose data are based on common statistical methods that assume that the sampled glucose data is normally (Gaussian) distributed. Normally distributed data provides a probability distribution that has the characteristic bell shape that decreases symmetrically on both sides of the mean peak.

In contrast, some researchers, [U.S. application Ser. No. 10/240,228, Kovatchev and Cox] have incorrectly suggested that the distribution of blood glucose follows a log-normal distribution. In addition, in their proposed method, the glycemic identity in mmol/l or mg/dl is lost and a surrogate value is used. As of today, there are no commercially available instruments or tools based on the assumption of glucose data being log-normally distributed or any other distribution, besides the normal Gaussian distribution.

The research behind the invention indicates that the concentration and dynamics of blood glucose are affected by biological constrains, various complex interactions and non-linear biological control mechanisms. Therefore, blood glucose and its measurements, generally is neither normally nor log-normally distributed. Thus, presentation, indication and statistics of glucose data are often biased and therefore impairing interpretation, treatment and potential feedback to the observer.

The glucose concentration exhibits a lower boundary, which implies that this concentration never drops to zero. Biologically, there are safety mechanisms like hormone signaling and glucose release that strives to supply vital organs with essential amounts of energy for survival. At the upper end of the scale another protective mechanism, the renal threshold, restricts cellular damage and acute ketoacidosis from elevated glucose levels. This inter-individually variable threshold triggers the kidneys to release excess glucose into the urine in relation to glucose level in gradually increasing amounts.

The above described boundaries are general in their mechanism. However, the concentration level at which they emerge and the resulting metabolic impact varies substantially between individuals. Importantly but entirely overlooked is the fact that every individual has a unique glucose probability distribution which in addition changes over time. Its shape and asymmetry are vastly affected by DM type, DM stage, glucose control and treatment regimen, see FIGS. 1 and 2. Consequently, current methods, instruments and tools do not take this into account and typically suffer from incorrect bias.

Presentation and Graphical Interpretation

Currently used means for the presentation and display of glucose data in self-management of diabetes or clinical instruments utilize a linear presentation scale. Typical instruments are glucometers, CGM and various computer software tools. The presentation and display of glucose information are neither adapted to, nor corrected for the unique physiological state, glucose dynamics and glucose statistics that characterize an individual diabetic patient, or patient population. The typical cluster of glucose readings will generally not be symmetrically distributed around the mean—making interpretation of changes in glucose levels difficult and sometimes misleading or obscured for the observer. Additionally, a universal presentation scale based on the assumption of a typical distribution (normal or even log-normal), will for many patients suppress the resolution in important areas of the blood glucose range such as in the hypo- or hyperglycemic regions, thus obscuring potential risk assessment.

Real Time Glucose Monitoring and Related Methods

A subarea of glucose monitoring focuses on real-time measurements. This mainly involves a continuous glucose monitoring device (CGM), or in combination with an insulin administration pump, forming an artificial pancreas. Real-time monitoring of changes in glucose concentration usually consists of rate of change indicators and predictive alarms. For adequate performance such features require some kind of linearization of the glucose propagation over time. This precondition is generally not fulfilled.

Rate of change is presented in some instruments by an arrow where the tilt angle reflects the velocity and estimated risk of the glucose change. As the detector driving the tilt angle of the arrow usually does not take into account the non-linear glucose propagation, the indication is often misleading. Thus such indicators fail to properly demonstrate the magnitude of the risk posed by a certain glucose level change.

Furthermore, the non-linear glucose propagation impairs the accuracy and reliability of typical alarm prediction algorithms. This results in unnecessary and irrelevant alarms and indications in the hyperglycemic range, and too few alarms and too small indications in the hypoglycemic range for certain types of DM patients. Thus, the true clinical value of this feature has been somewhat limited.

Statistical Measures

Statistical analyses, for example estimation of glucose mean values and glucose variability is a typical feature within more advanced glucometers, COM and computer software tools. The estimation of average glucose levels is fundamental in diagnosis, classification, self-care and treatment. The normal practice of estimating the average glucose value is by the use of the arithmetic mean. For asymmetric glucose distributions this renders unreliable results. Further, the variability measures, i.e. the standard deviation or coefficient of variation, are affected by both the properties of the glucose distribution and the way the mean value was obtained. From a treatment perspective, the disadvantages of these standard measures imply a reduced accuracy in diagnosis, improper interpretation and inaccurate results.

In conclusion, user feedback from measurements, diagnosis, analysis, treatment and self-care in the field of diabetes has since its inception been plagued with problems originating from the assumption that blood glucose data is normally distributed (or by some, logarithmically distributed). Unfortunately, this applies to everything from clinical lab equipment and self-management devices for glucose measurements, to results and statistics presented in clinical studies and scientific research.

SUMMARY

According to an embodiment, an apparatus for processing a set of data values, a data value representing a physiological measure of a body fluid at a time instant, may have: an estimated probability function calculator for calculating an estimated probability function associated with the set of data values; a transform calculator for calculating a non-linear transform rule using a predetermined target probability function being different from the estimated probability function and using the estimated probability function associated with the set of data values, so that the probability function of a set of transform data values is closer to the target probability function than the estimated probability function; and a transformer for applying the transform rule to the set of data values or to at least one further data value not included in the set of data values and sampled at the different time instant from the time instants for the set of data values to acquire at least one transformed value representing the physiological measure.

According to another embodiment, a method of processing a set of data values, a data value representing a physiological measure of a body fluid at a time instant, may have the steps of: calculating an estimated probability function associated with the set of data values; calculating a non-linear transform rule using a predetermined target probability function being different from the estimated probability function and using the estimated probability function associated with the set of data values, so that the probability function of a set of transform data values is closer to the target probability function than the estimated probability function; and applying the transform rule to the set of data values or to at least one further data value not included in the set of data values and sampled at the different time instant from the time instants for the set of data values to acquire at least one transformed value representing the physiological measure.

Another embodiment may have a computer program having a program code for performing, when running on a computer or a processor, the method of processing a set of data values, a data value representing a physiological measure of a body fluid at a time instant, which method may have the steps of: calculating an estimated probability function associated with the set of data values; calculating a non-linear transform rule using a predetermined target probability function being different from the estimated probability function and using the estimated probability function associated with the set of data values, so that the probability function of a set of transform data values is closer to the target probability function than the estimated probability function; and applying the transform rule to the set of data values or to at least one further data value not included in the set of data values and sampled at the different time instant from the time instants for the set of data values to acquire at least one transformed value representing the physiological measure.

The theoretical research behind the present invention demonstrates that every individual has a unique and—over time—changing glucose probability distribution vastly affected by DM type, DM stage, glucose control and treatment regimen, see FIG. 1. The invention and the embodiments described herein, teaches a novel transform method for improving presentation, interpretation, self-care, clinical decision-making and glycemic control from stored, displayed and/or measured glycemic data.

In particular, the invention teaches a transform method that transforms any glycemic data set into a specific target distribution. The choice of target distribution depends of the nature of the specific application and use of the transform such as visual presentation (treatment guidance), statistical analysis (diagnosis and classification), prediction (alarms) or insulin dosing (artificial pancreas). Further, the transform can be optimized for any individual or any population independent of the glucose distribution of the raw data. The transforms based on the invention are intended for use in various types of devices related to glucose monitoring, calculations or presentations including glucometers, systems involving insulin pumps, computer software and medical devices.

A further embodiment of the invention teaches a simplified transform of reduced flexibility and accuracy, which can be used in applications where computational cost and complexity is of concern.

Presentation and Graphical Interpretation

One embodiment of the present invention teaches a method, based on the transformation, for improved visual presentation of glycemic data and readings. The method is based on a presentation scale obtained from a given population's statistical distribution. The invention offers enhanced visualization of glucose changes and variations. This improves the user's understanding of glucose dynamics which in turn benefits self-care and treatment. Thus the risk and physiological impact posed by a certain glucose level change is more adequately reflected. The improved utilization of the diagram space results in superior interpretation of small, but from a treatment perspective important glucose concentration changes. From a treatment perspective this presentation scale enables a statistically and more physiologically accurate way of presenting, displaying, and analyzing glycemic information thus improving the probability of taking appropriate action and improving self-care.

The transform can be used to generate presentation scales for different populations defined by DM type, blood glucose control or for a defined treatment regimen. The glycemic data is visualized graphically by using an individualized or population based non-linear transformed scale in a graphic diagram, where the tick positions on the Y-axis are re-located according to the transform while the corresponding tick labels retain their original identity. The glycemic identity i.e. mmol/l or mg/dl is therefore retained. The positioning and resolution of tick marks can be adjusted according to the user's preference.

For instance, in one mode of the embodiment the relocated tick marks are equidistant (and the tick-mark values are approximately exact), in order to resemble a typical linear graphic diagram. In another mode of the embodiment the relocated tick marks are near-equidistant (and the tick-mark values are coarsely rounded) in order to resemble a typical linear graphic diagram as closely as possible.

Real Time Glucose Monitoring and Related Methods

Another embodiment of the invention teaches a method, based on the transformation, for linearizing arbitrary blood glucose level changes along the glucose concentration range in CGM. The proposed method is preferably applied prior to rate of change indicators. This improves sensitivity and accuracy, visualizing the true impact that a given blood glucose rate of change will impose on the individual. Thus, the user can better interpret and understand the dynamics of the glycemic events and react accordingly. The rate of change can be presented visually, most typically in the form of an arrow or an audible signal where the arrow tilt angle or audible tone reflects the rate of change.

Another embodiment of the invention applies the linearizing transform to improve predictive alarms concerning real-time monitoring typical of CGM. The accuracy and reliability of such alarms are thus improved, resulting in better predictions of potential hyper- or hypoglycemic events and a reduction of irrelevant alarms.

Statistical Measures

For diagnosis, classification and treatment of different types and stages of diabetes and metabolic syndrome, it is fundamental to observe and analyze how and why the mean value and the variability of the glucose concentration changes over time with various self-care and treatment methods. With accurate and reliable statistical measures according to the invention, new insight and understanding is gained.

Another embodiment of the invention teaches a method based on the transformation, for conducting statistical analysis on glycemic data in the form of an improved and significantly more accurate mean value measure of glycemic data compared to what is currently available. The method is more robust as well as more effective in the sense that the number of measurements needed to generate a reliable mean value are significantly reduced.

Yet another embodiment of the invention teaches a method based on the transformation, for conducting improved and significantly more accurate variability measures of glycemic data i.e. the standard deviation (SD) or the coefficient of variation (CV), This includes the upside standard deviation (USD) and downside standard deviation (DSD) as well as the upside coefficient of variation (UCV) and downside coefficient of variation (DCV). Measures of variation have recently gained serious interest as risk measures due to scientific discoveries that link the development of diabetes complications not only to the mean glucose level but also to glucose variability.

Artificial Pancreas Regulation

Yet another embodiment of the invention teaches a method, based on the transformation, to improve the performance and accuracy of open or closed loop artificial pancreas regulation, by inserting the transform between the glucose sensor and the regulator, thus linearizing the response from the glucose sensor, and reducing the burden on the controller algorithm thus optimizing response.

In accordance with a first aspect of the present invention, an apparatus and a method are provided for processing a set of data values, a data value representing the physiological measure of a body fluid at a time instant. The apparatus comprising an estimated probability function calculator for calculating an estimated probability function associated with the set of data values, a transform calculator for calculating a non-linear transform rule using a predetermined target probability function being different from the estimated probability function, so that the probability function of a set of transform data values is closer to the target probability function than the actual probability function, and the transformer for applying the transform rule to the set of data values or to a further data value not included in the set of data values sampled at the different time instant from the time instance for the set of data values to obtain at least one transform value representing the physiological measure. Advantageously, the probability function is a probability density function or a cumulative distribution function. The probability density function or the cumulative distribution function can be used for the estimated probability function and/or for the target probability function. The data values can represent any physiological measure of a body fluid and in one embodiment, are glycemic values which have been obtained by a blood analysis, or which are sampled using any other non-invasive means.

In an embodiment, the apparatus for processing a set of data values additionally comprises a device for using the at least one transformed value for controlling a device for dosing a medicament in a closed or open loop configuration or for generating a visual, audible, tactile, mechanical, electro or magnetic indication of a medical characteristic of the body for which the set of data values or the at least one further data value have been taken.

It is a specific feature of this aspect that the transform is actually calculated so that the set of data values, when subjected to the transform, is transformed into a transformed set of data values which actually have the target probability function. Hence, in an implementation, a set of data values having a non-normal distribution can be transformed into a set of data values having a normal distribution so that any calculations, analysis steps or other processing, which rely on the assumption that the underlying data set has normal distribution can be applied to the transformed set of data values in order to obtain much more accurate results compared to the situation when the same procedures would be applied to a non-transformed set that violates the assumption of a normal distribution.

In accordance with a further aspect, an apparatus for processing a glycemic value comprises a transformer for transforming the glycemic value into a transformed glycemic value, wherein the transformer is configured for applying a transform rule to the glycemic value, the transform rule comprising a combination of a first logarithmic term comprising a logarithm of the glycemic value and of a second linear term comprising a linear contribution of the glycemic value, wherein the transform is such that, for each glycemic value of a set of glycemic values having more than one glycemic value, the first logarithmic term and the second linear term both influence the corresponding transformed glycemic value.

The transformer can be configured for using a transform map or transform parameters stored in a memory such as a look-up table for the transform map or any other memory for the parameters, or the transformer can be implemented for actually calculating the transform map having the linear/logarithmic characteristic from a set of data values belonging to a certain person or a certain population or a certain group of populations in order to have a very accurate and specific transform rule. The transform rule will have the basic characteristic that there is a linear contribution and a logarithmic contribution, and importantly a mixture or combination of both contributions, where in an implementation the linear term is for higher glycemic values and the logarithmic term is for lower glycemic values. Importantly, both terms influence more or less the transformed value, since a piecewise transform having a first portion until a certain border value which is a logarithmic function and having a second portion for higher values than the border value which is a linear function does not accurately reflect the statistics within glycemic data so that such a "piecewise" transform will not result in a high quality transform having a set of transformed values showing a more accurate Gaussian normal distribution than the set of values had before the transform.

In an implementation, the apparatus furthermore comprises a processor for processing the transformed glycemic value for the purpose of generating an optical, audio, tactile, electrical, magnetic or mechanical signal derived from the transformed glycemic value. An implementation is, for example, that the processor calculates a mean value of the transformed set of values and transforms the mean value back into the non-transformed domain, where the back-transformed mean value is displayed or indicated in any other way in order to give a much more accurate tool for the patient's self-control or the doctor's diagnosis/treatment strategy for a certain patient. Depending on the implementation, different tick marks can be used in order to represent data output by the transformer in a graphical way. Different spacings between tick marks or equal spacings between tick marks can be applied, where the specific position of a tick mark in a transform diagram illustrating transformed values is calculated by transforming the real value corresponding to this transformed value. Furthermore, it is advantageous to perform a graphical display in such a way that the real values are indicated near the tick marks for the corresponding transformed values in the graphical illustration of transformed data so that the user nevertheless has a good and intuitive understanding of the transform domain. This procedure can be applied for the log/lin transform, or of course for the transform calculated using the target and estimated probability function.

A further aspect relates to an apparatus and method for generating a condition indication using a time sequence of data values, where each data value represents a physiological measure of a condition of a subject. The apparatus comprises a transformer for transforming the time sequence of data values into a transformed sequence of data values using a transform rule, wherein the transform rule is such that a certain characteristic in a time course of the physiological measure is more linear than the time course of the certain characteristic before the transform. The apparatus furthermore comprises a rate of change calculator for calculating an estimated rate of change for the transformed sequence of data values, and a processor for processing the estimated rate of change to output the condition indication for a subject. The subject can be a human being or an animal. In an implementation, the certain characteristic is a fall or a rise of the physiological measure, wherein in a further embodiment, the physiological measure is a blood glucose measure so that the certain characteristic is a blood glucose rise or a blood glucose fall. However, any other physiological measure, for which a rate of change is of interest such as a characteristic to be measured from a body fluid such as blood, urine or lymphatic fluid, can be processed using the apparatus and method as well. Additionally, any other physiological measures which do not depend on a fluid or liquid sample can be analyzed as well, when a better rate of change calculation is of interest such as non-invasively taken measurement values obtained by an EKG, a blood pressure measurement or any other such non-invasive measurements.

Additionally, although a certain characteristic under consideration is a fall, for example, of a blood glucose value, another characteristic such as a rise of the value over time, an oscillation of the value over time or a certain pattern of the values over time, such as specific rises or falls e.g., logarithmic or sine-like rises and falls can be used as the certain characteristic as well. The selection of the certain characteristic and analysis of the certain characteristic only depends on the generation of the data being the basis for the transform rule, and additionally there should be an interest to linearize this certain characteristic in order to have a better rate of change measure compared to a situation where the transform has not been applied.

An implementation relates to a generation of graphical, audible or tactile display of the estimated rate of change or for generating an electrical, magnetic or electromagnetic signal representing the estimated rate of change. Another implementation relates to the prediction of a future or later data value, where depending on whether the later value is above or below a threshold such as an alarm threshold, an alarm indication is generated, which is visual, audible, tactile, mechanical, electro or magnetic-like.

The probability function can be any probability related function such as a probability density function (PDF) or a cumulative distribution function (CDF) or the like, as long as this function has values that are related or depend on a probability that a certain value or certain values of a set of values occurs.

In an implementation, the rate of change calculator is configured for calculating a difference between two transformed values of the sequence of transformed values and for dividing the difference by a time difference between the time instances associated with the two transformed values, where the time instances associated with the two transformed values depend on the certain characteristic such as typical blood glucose fall or typical blood glucose rise. Any rises or falls cannot only be used and calculated for blood glucose values but for any other physiological measures as discussed. In an implementation, the calculation of the predicted data value is performed using a linear function defined by a data value of the transformed time sequence of data values and the calculated rate of change so that based e.g. on an extrapolation, an intersection point between the linear function and the alarm threshold can be detected in order to find the time duration, in which an alarm state will be reached in order to warn accordingly. Instead of an extrapolation, one could also use a higher order or more advanced prediction method to find an even more accurate estimate of the true intersection point.

An alternative implementation is to find out whether a predicted value in a certain selected future time period is, for example, below an alarm threshold so that when this is the case a physical warning indication can be communicated to the patient. This procedure is specifically used for continuous blood glucose measurement devices, but can also be applied for non-continuous blood glucose measurements where, for example, samples are not taken in five minute distances or so, but probably with a sampling period of hours or even more, as long as a time sequence of data values is obtained and is ready for processing.

Aspects of the present invention relate to a transform method and embodiments used to display, present, interpret, control and/or convert glycemic values in a novel and substantially improved way. Specifically aspects of the invention teach how to apply a transform method that is optimized for a large or small population, or even for an individual, in order to improve and enhance observation, interpretation and decision-making when presenting, reading, interpreting, controlling or making decisions from stored, displayed and/or measured glycemic data. The non-linear glucose transform (NLGT) according to aspects of the present invention, offers a physiologically and statistically more accurate way of representing glycemic information. In addition it offers higher accuracy compared to conventional methods, when interpreting and evaluating the effect, impact and risk from glycemic information.

BRIEF. DESCRIPTION OF THE DRAWINGS

A better understanding of the features and advantages of the present invention will be obtained by reference to the following description that sets forth illustrative embodiments in which principles of the invention are utilized by reference to the accompanying drawings:

FIG. 1: illustrates PDFs for three example patients with different glucose mean values.

FIG. 2: illustrates a mean skewness for glucose data sets with different glucose mean values.

FIG. 3: illustrates a block diagram for creating a data optimized NLGT-transform.

FIG. 4a: illustrates an estimated PDF, as a sum of weighted normal probability density functions for each bin.

FIG. 4b: illustrates an estimated CDF, as a sum of weighted normal cumulative distribution functions for each bin.

FIG. 4c is a flowchart illustrating an implementation of the estimated probability function calculator.

FIG. 5: illustrates an estimated cumulative distribution function, CDF, and true CDF for the data set.

FIG. 6: illustrates an estimated CDF and target function.

FIG. 7: illustrates a block diagram for creating a population based NLGT transform.

FIG. 8a: illustrates a population optimized transform based on data sets from 60 individuals from the DCCT study and the estimated Log-linear transform with a specific P and M.

Figure 9A:
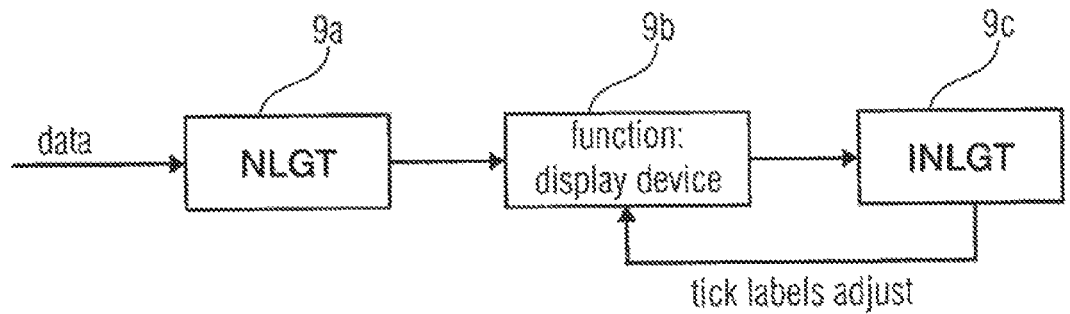

FIG. 9a: illustrates a block diagram for graphical presentation of data.

Figure 9B:
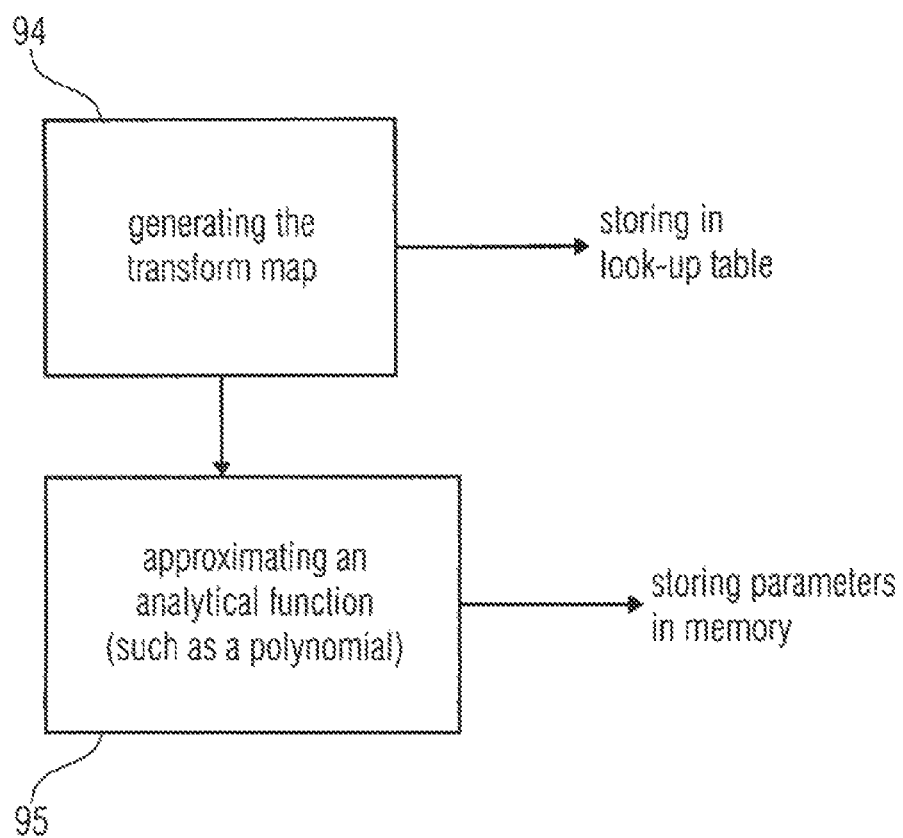

FIG. 9b illustrates an implementation of a transform calculator of the apparatus for processing a set of data values in accordance with a further aspect.

Figure 9C:
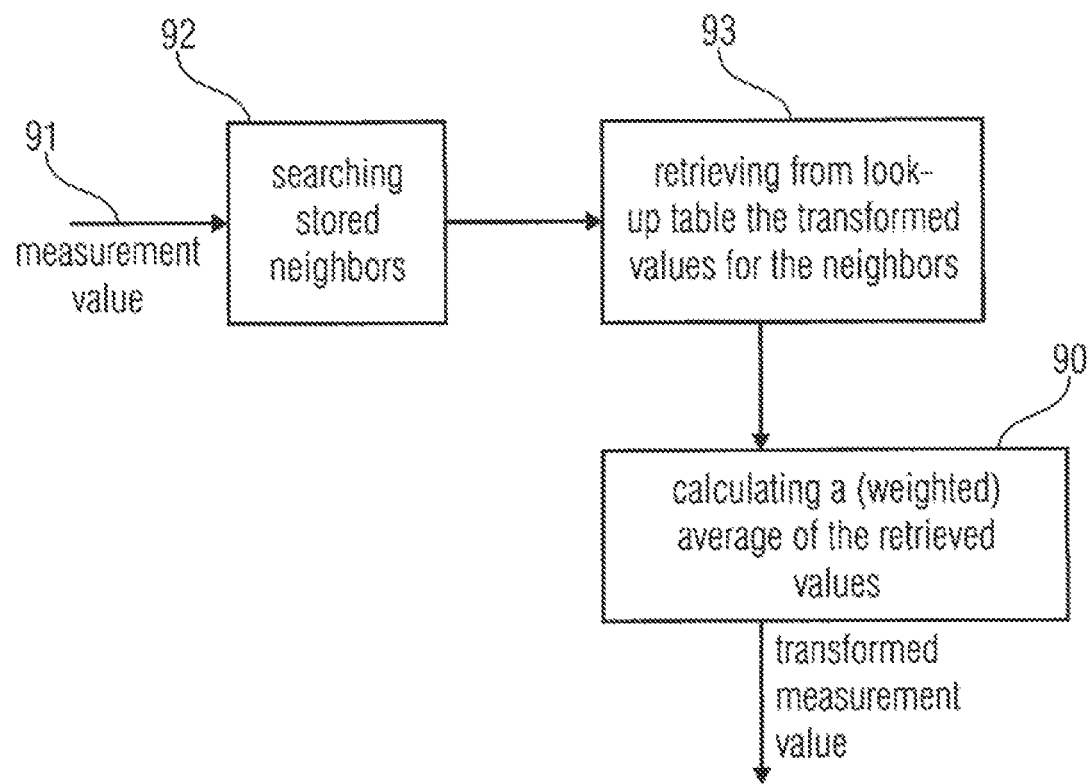

FIG. 9c illustrates an implementation of an interpolation procedure in the context of a transform map stored in a look-up table as pairs of values where one value of the pair is a non-transformed value and the other value of the pair is a correspondingly transformed value.

Figure 10:
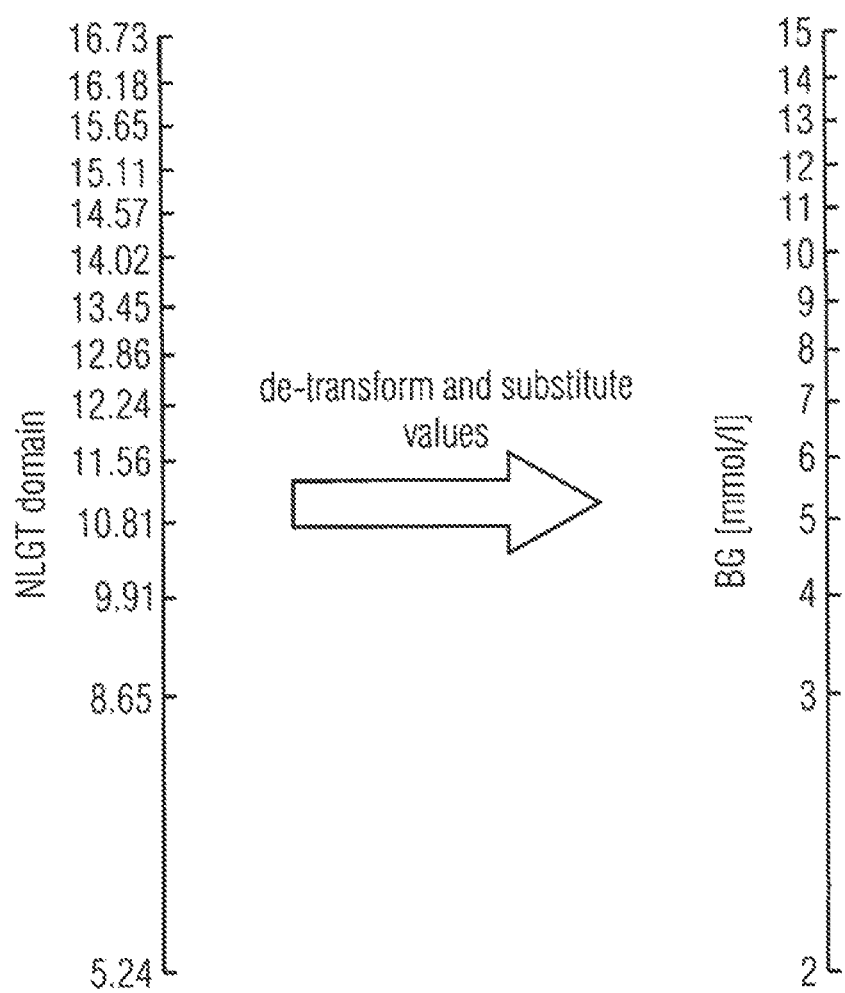

FIG. 10: illustrates a substitution of axis values to restore and retain the blood glucose identity in mmol/l or mg/dl.

Figure 11:
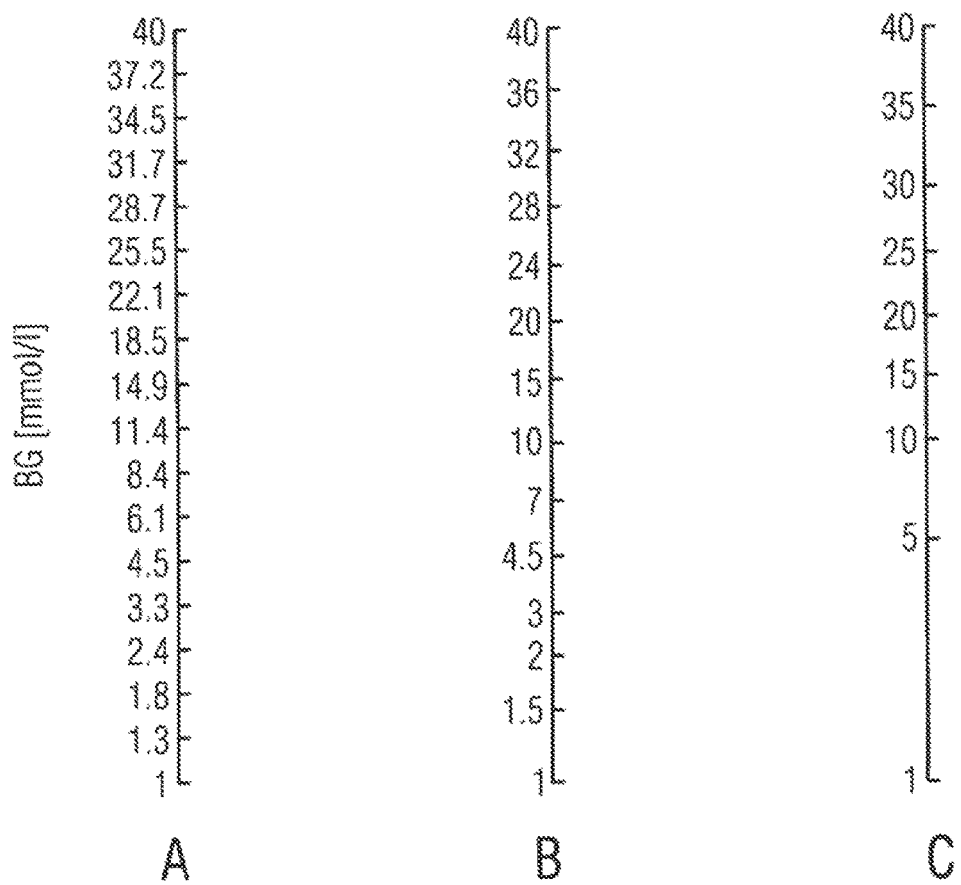

FIG. 11: illustrates different designs of the NLGT-axis.

Figure 12A:
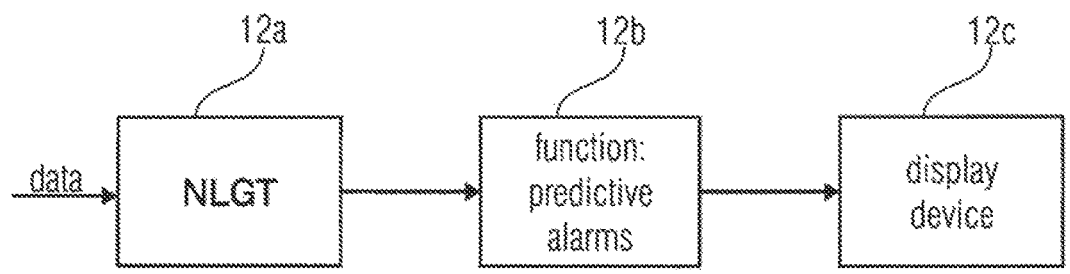

FIG. 12a: illustrates a block diagram for predictive alarms using NLGT.

Figure 12B:
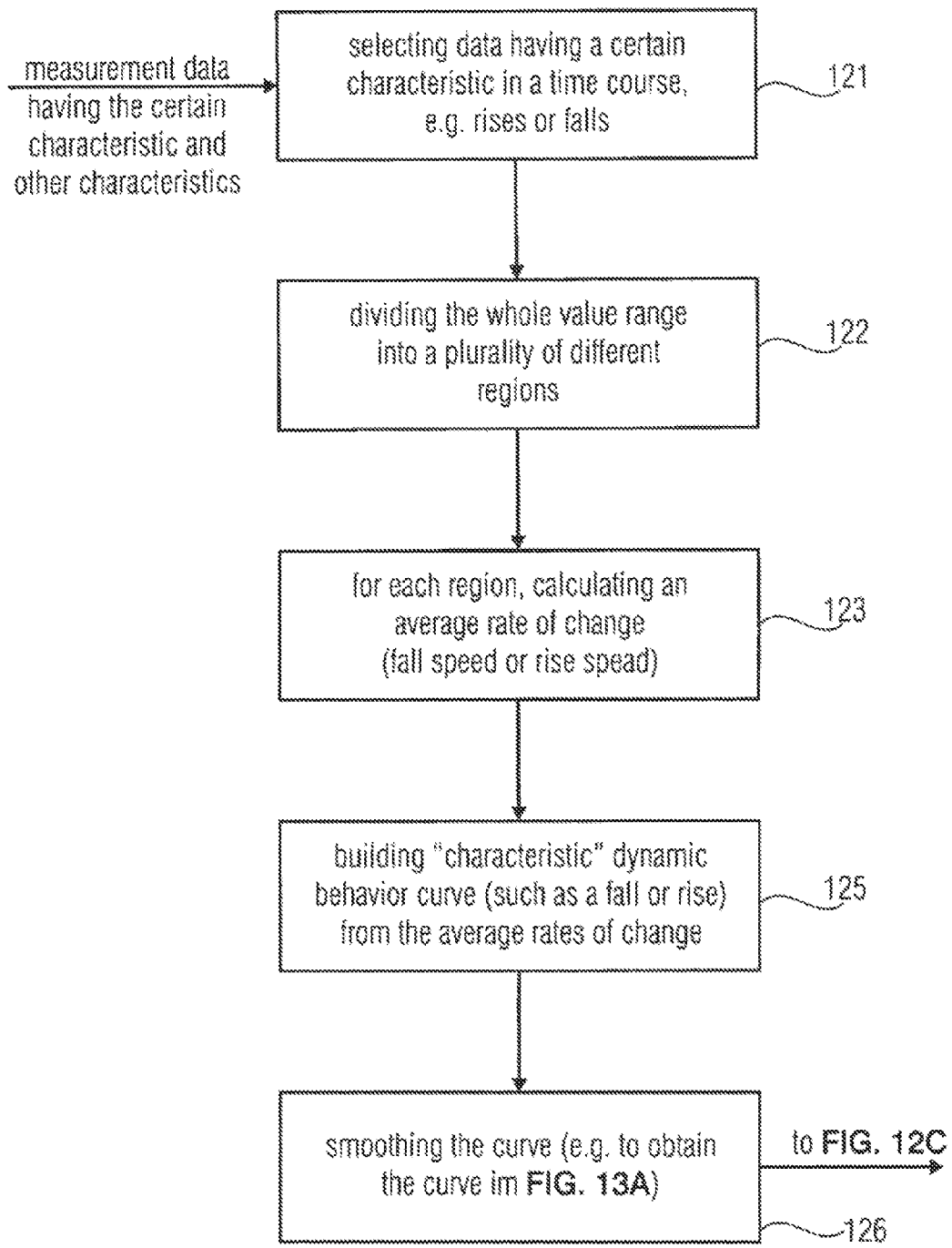

FIG. 12b illustrates an implementation of a transformer of the apparatus for generating a condition indication in accordance with a further aspect in order to find the certain characteristic such as a typical blood glucose fall over the whole value range.

Figure 12C:
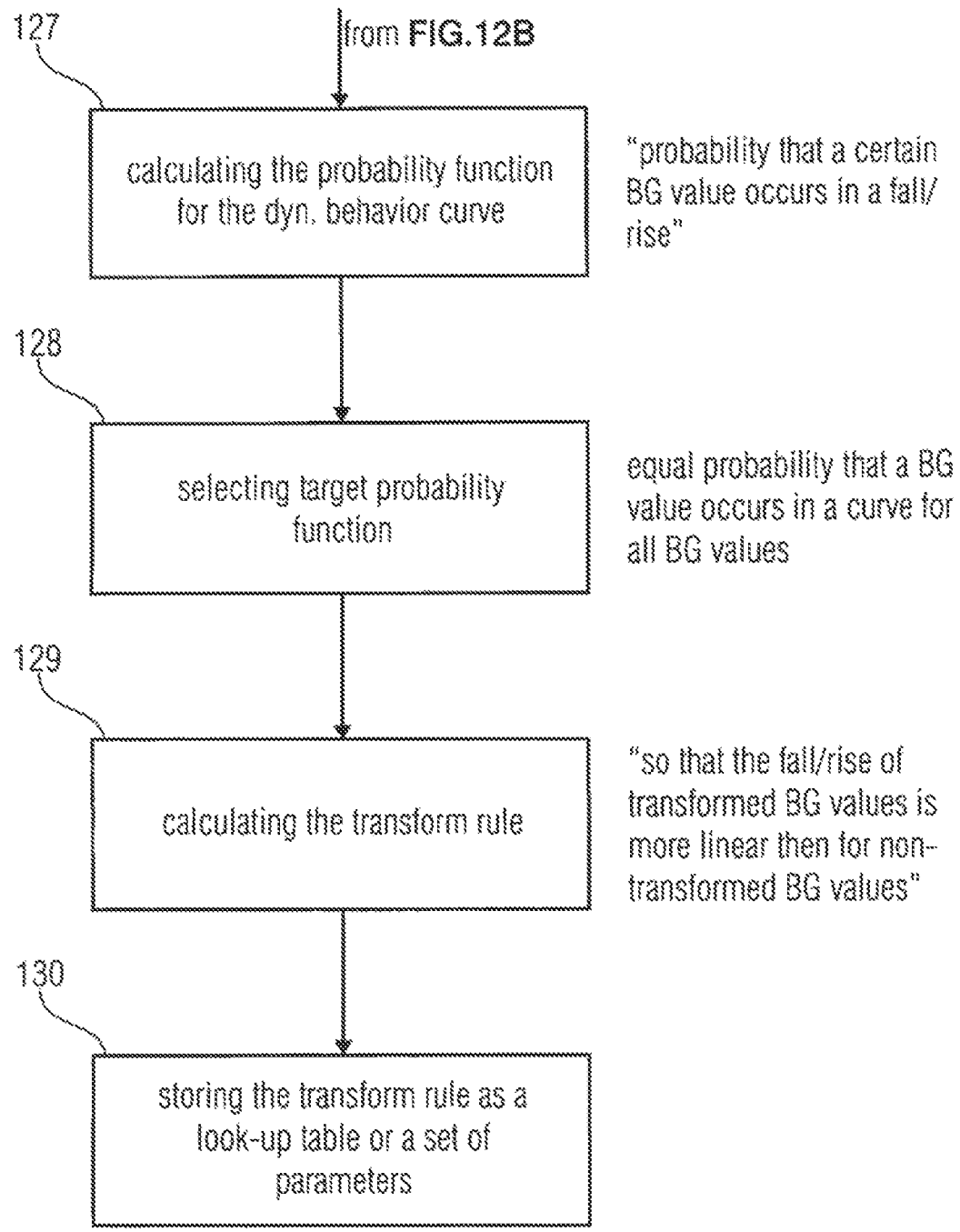

FIG. 12c illustrates an implementation of the transformer where the transformer actually calculates a probability function for the dynamic behavior curve and finally calculates, from the probability function and a target probability function being a probability function for a linear characteristic, the transform rule.

Figure 12D:
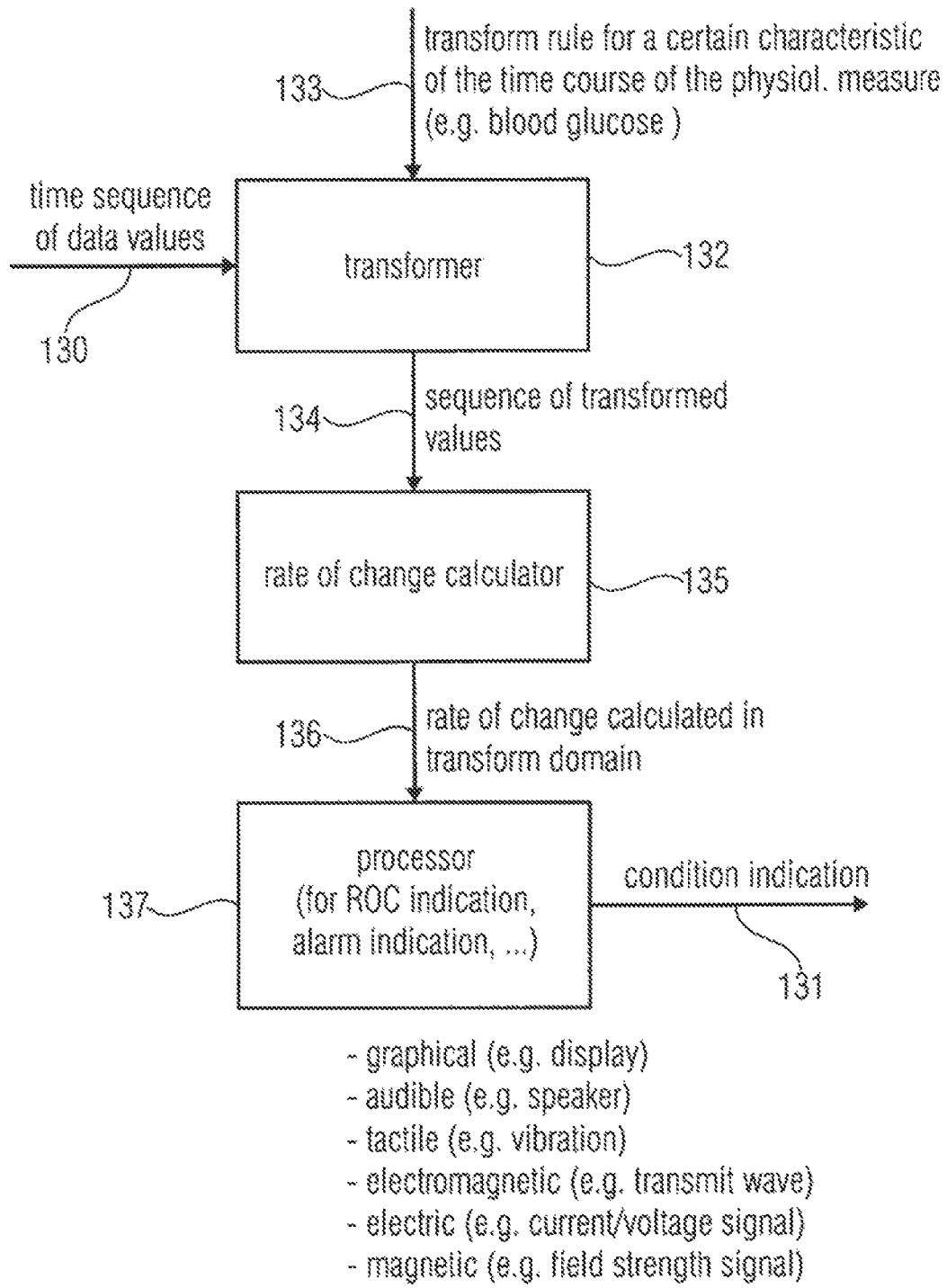

FIG. 12d illustrates a block diagram of an apparatus for generating a condition indication in accordance with an aspect of the invention.

Figure 12E:
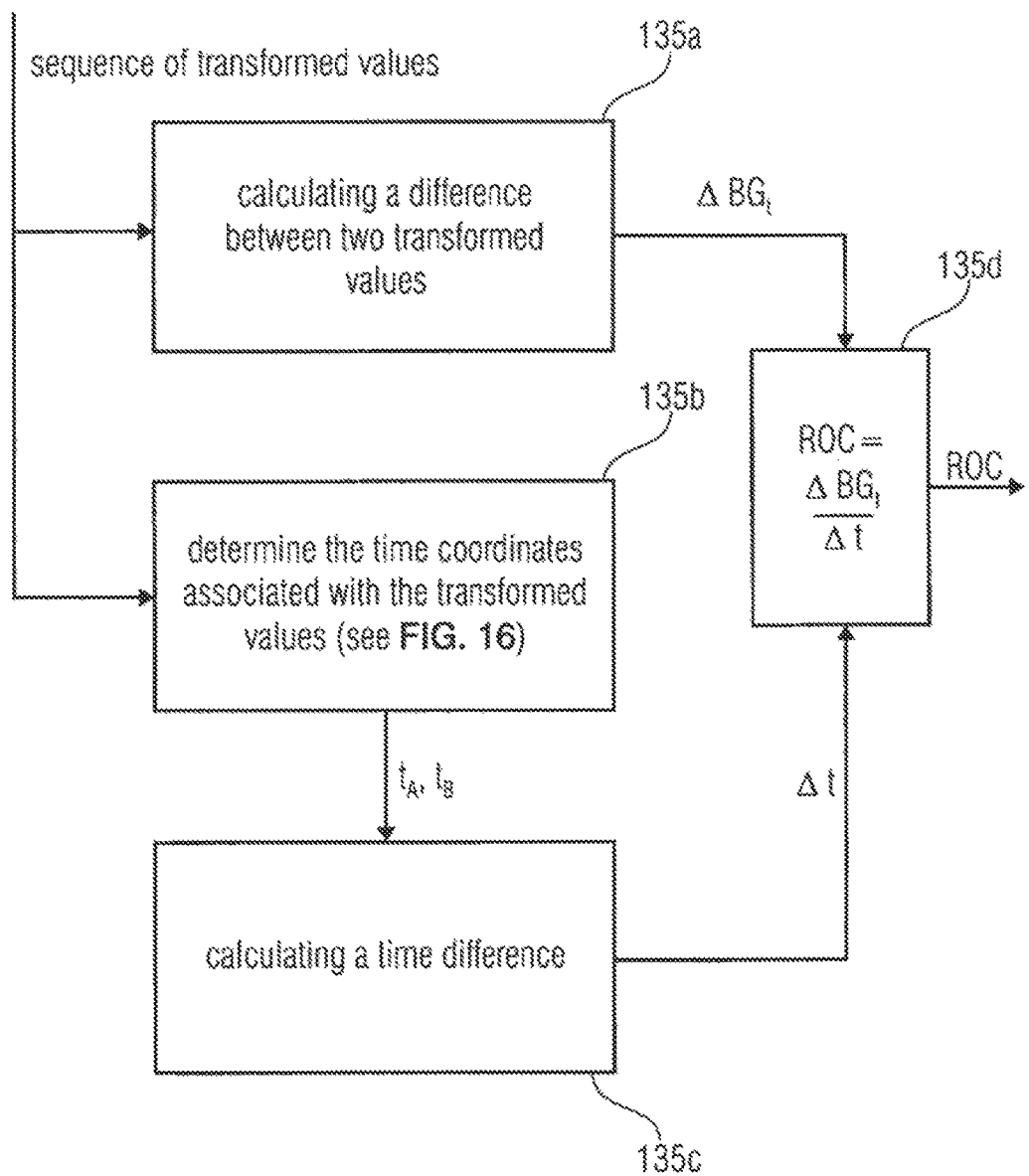

FIG. 12e illustrates an implementation of the rate of change calculator.

Figure 12F:
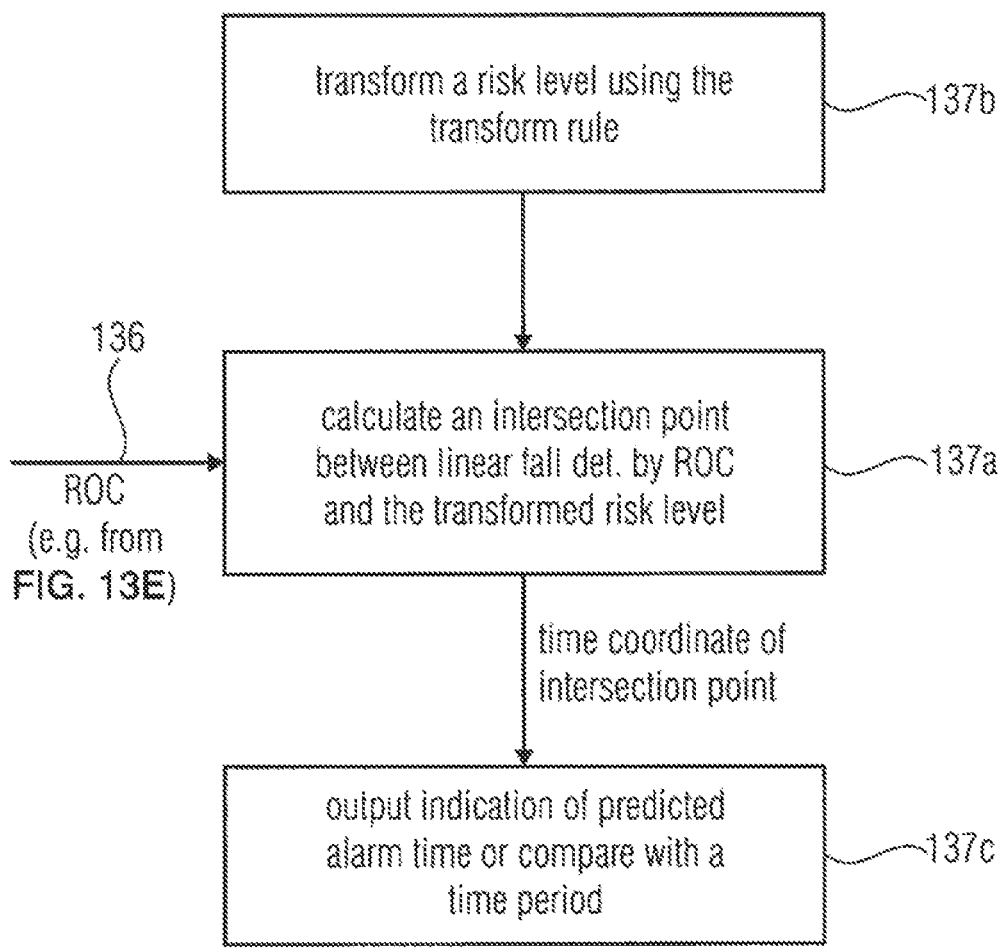

FIG. 12f illustrates an implementation of the processor when operating in a prediction operation.

Figure 12G:
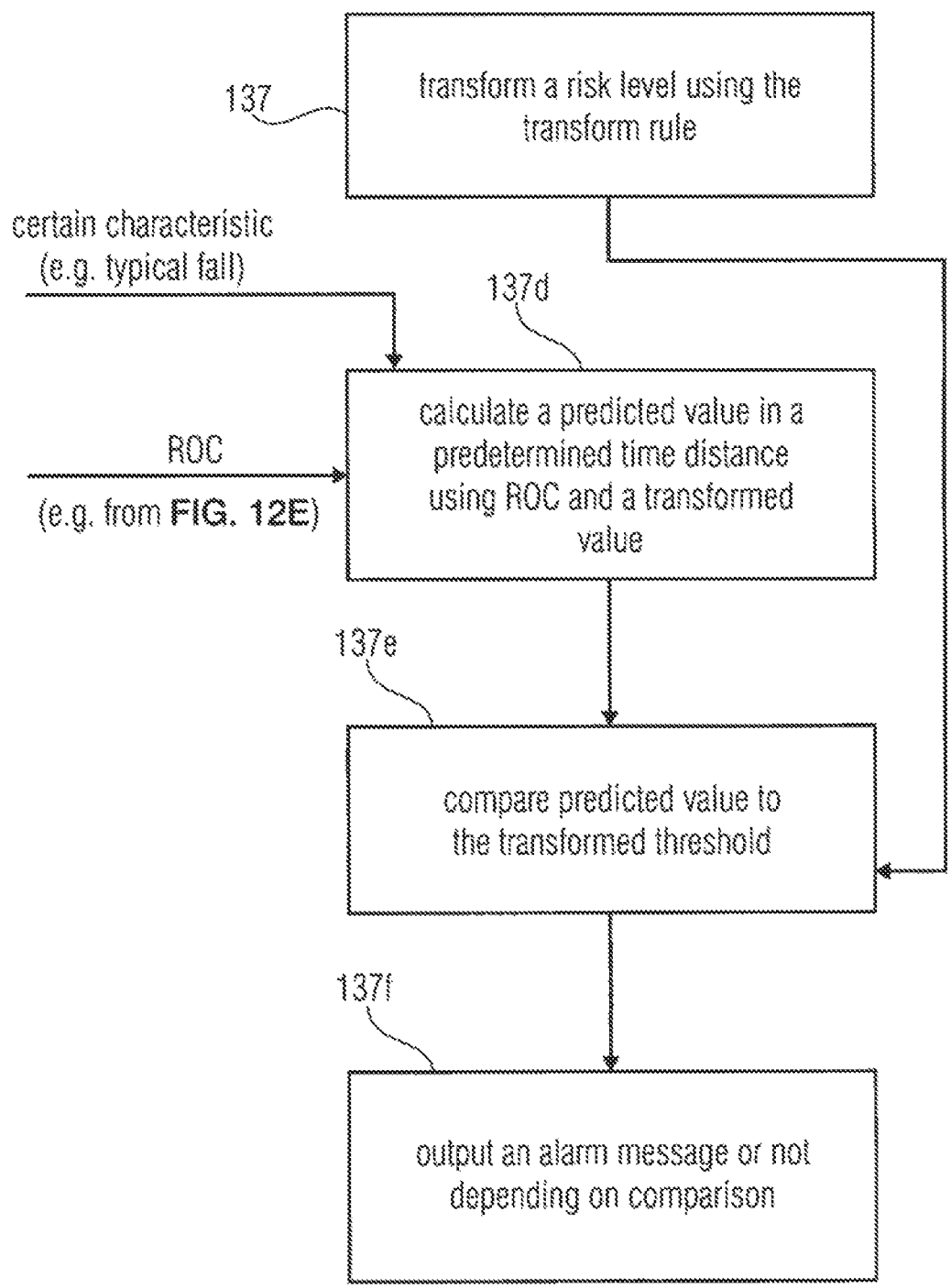

FIG. 12g illustrates a further implementation of the processor when operating in a further prediction mode.

Figure 12H:
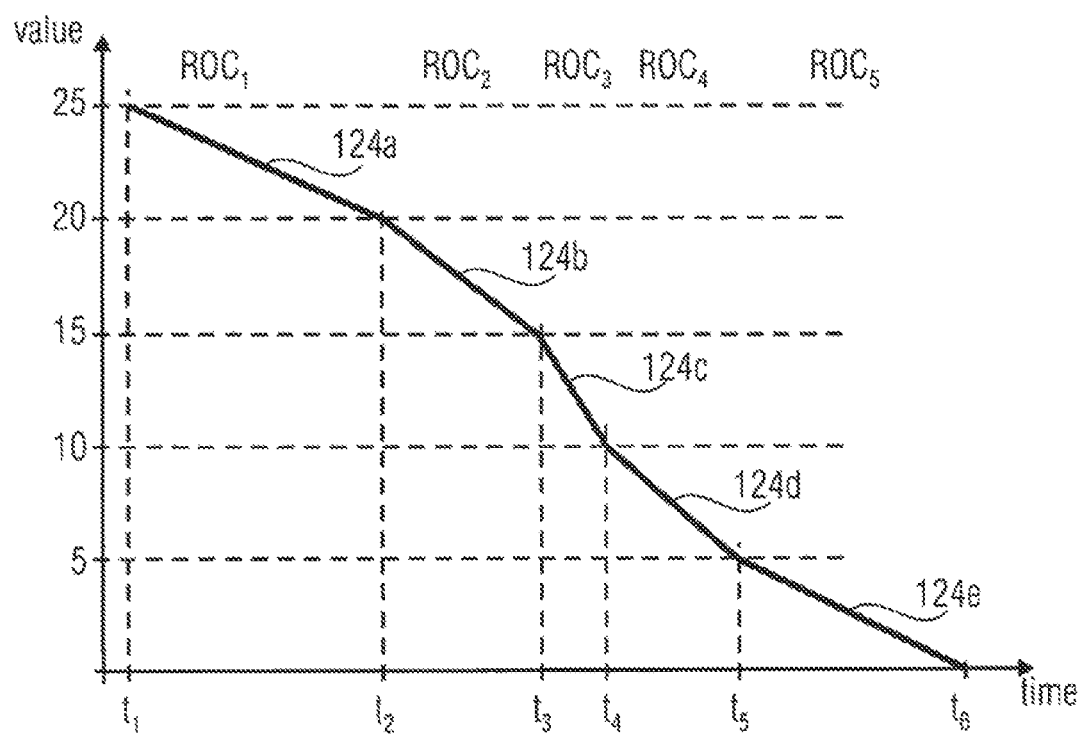

FIG. 12h illustrates a typical characteristic for explaining the generation of the data illustrated in FIG. 13 with a higher number of value ranges.

Figure 13A:
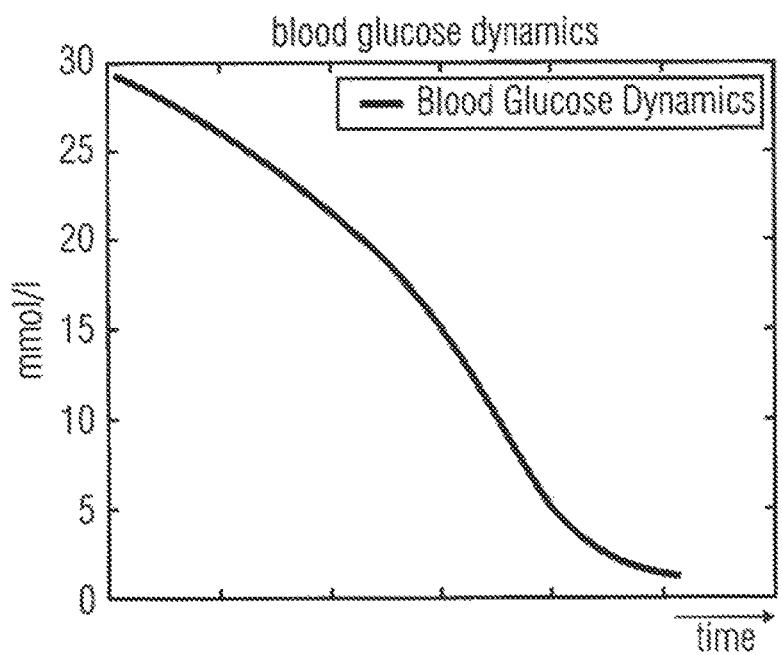

FIG. 13a: illustrates an example of blood glucose dynamics originating from 30 type-1 diabetics, using CGM with 5 minutes sampling rate.

Figure 13B:
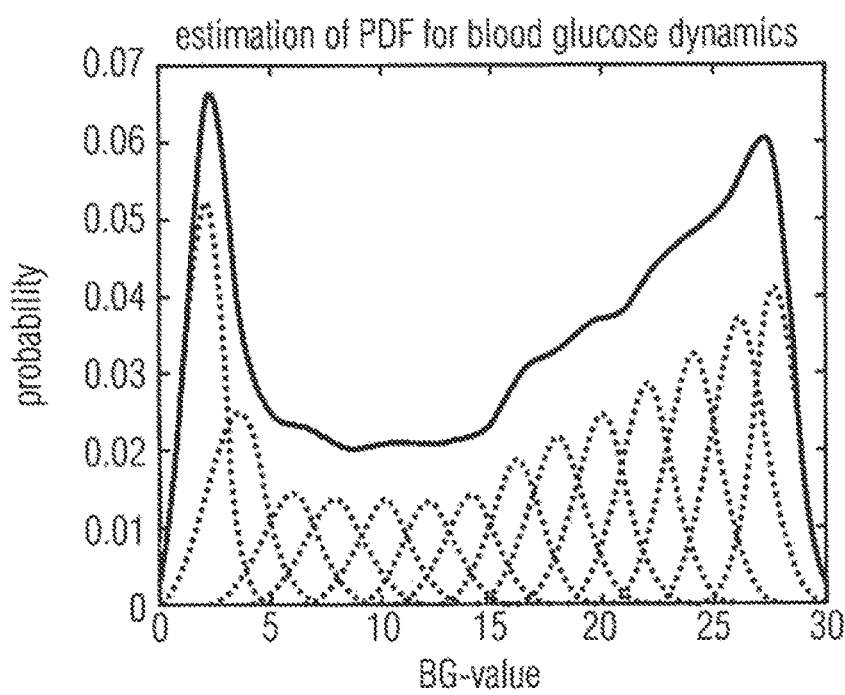

FIG. 13b: illustrates an estimated PDF for the blood glucose dynamics in FIG. 13a.

Figure 13C:
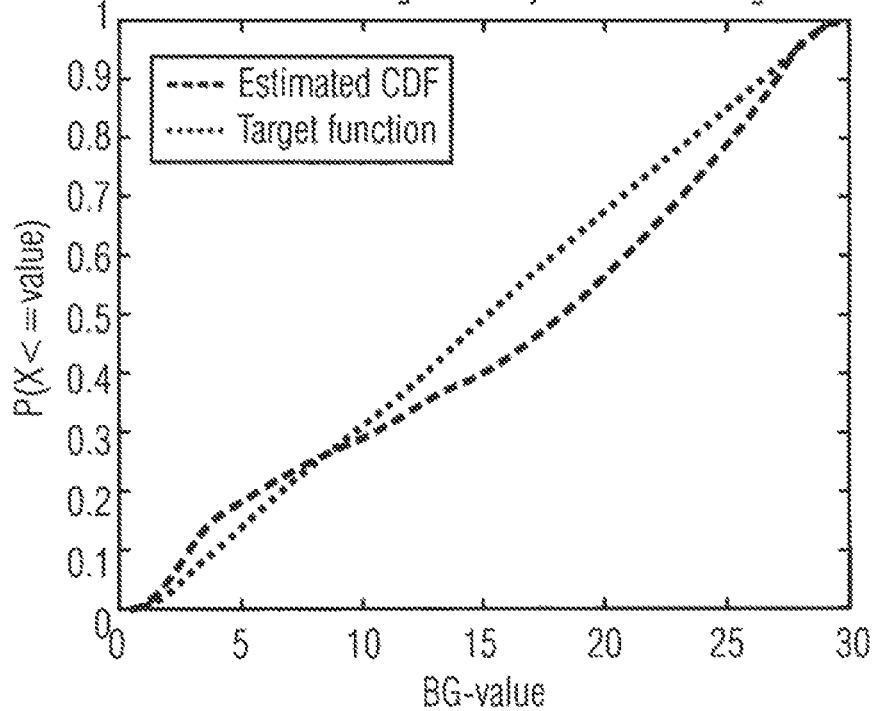

FIG. 13c: illustrates an estimated CDF for the blood glucose dynamics in FIG. 13a and the uniform target CDF.

Figure 13D:
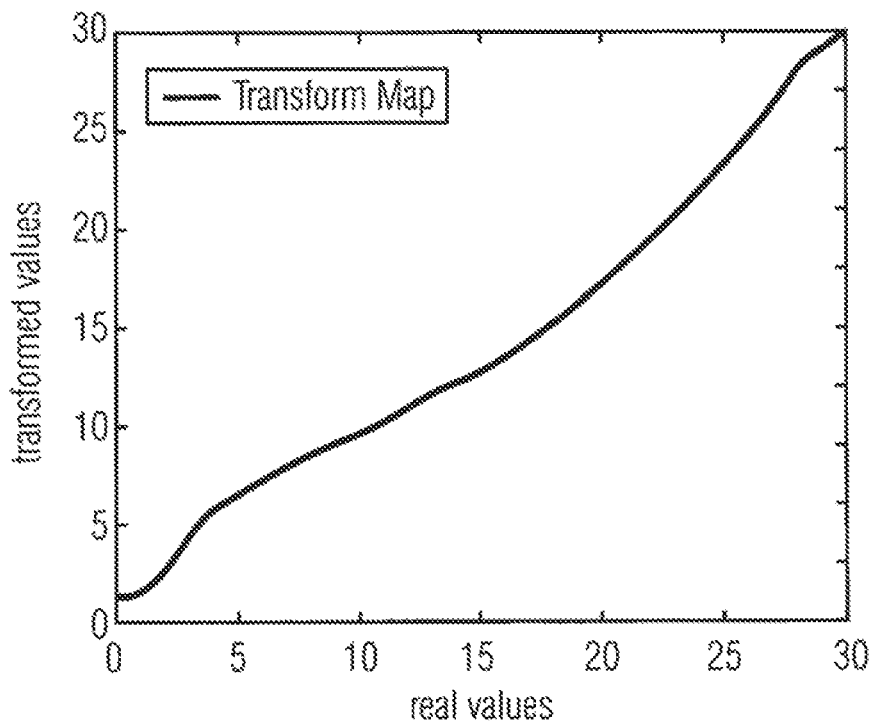

FIG. 13d: illustrates a transform map generated from the estimated CDF for the blood glucose dynamics in FIG. 13a and the uniform target CDF, shown in FIG. 13c.

Figure 13E:
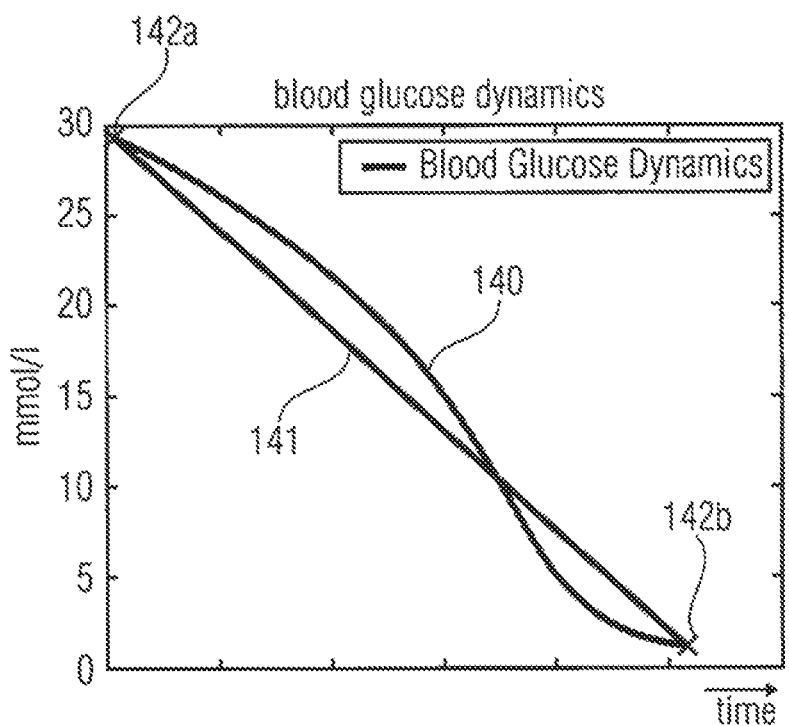

FIG. 13e: illustrates an alternative implementation and determination of the transform rule for linearizing the certain characteristic.

Figure 14:
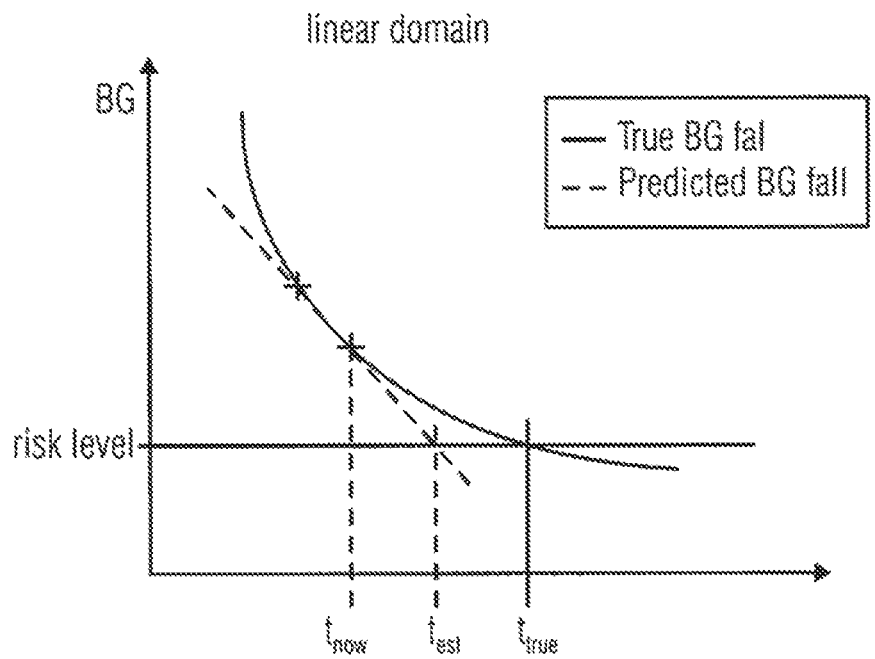

FIG. 14: illustrates a schematic depiction of how non-linear glucose propagation affects alarm prediction algorithms.

Figure 15:
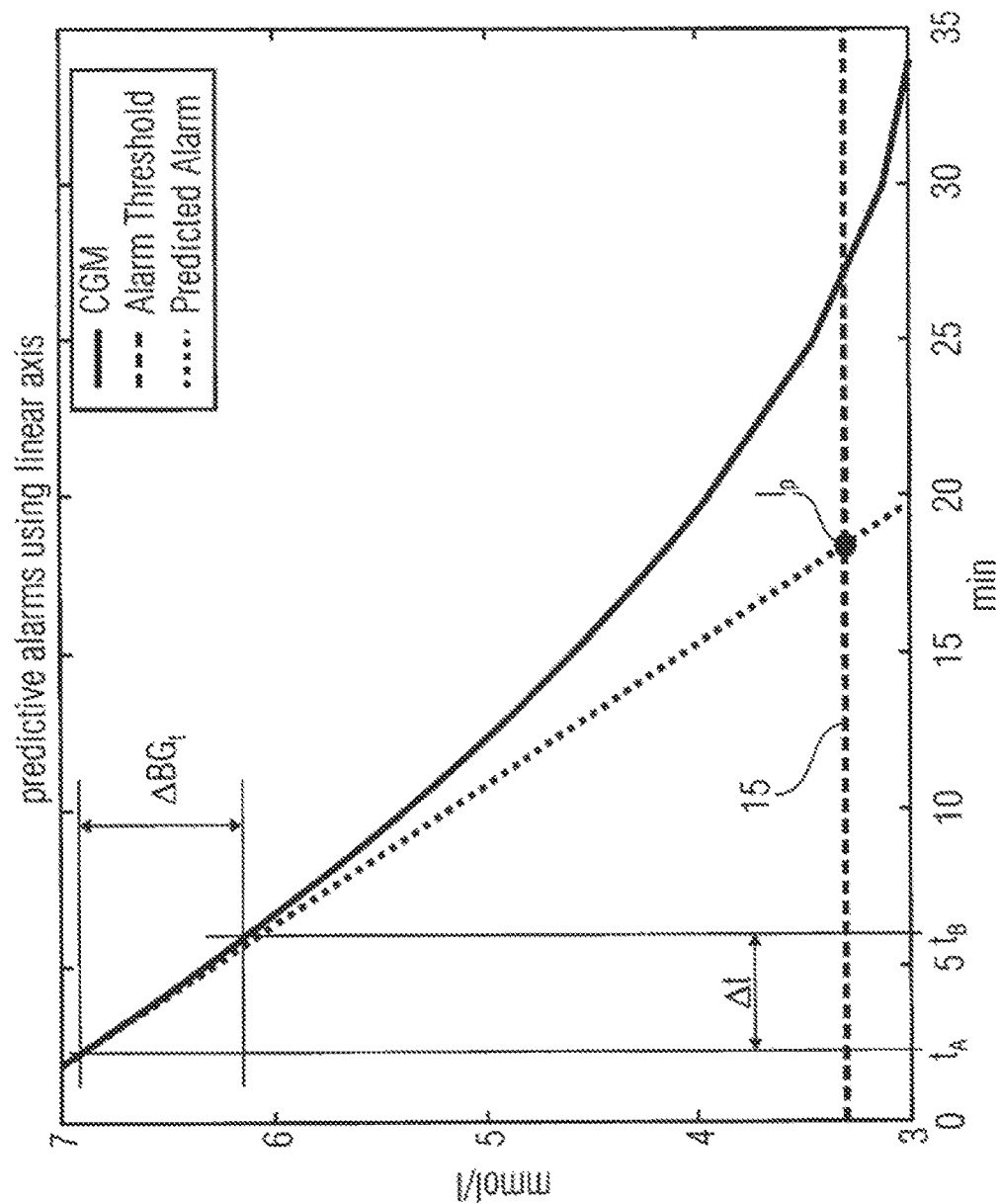

FIG. 15: illustrates an alarm prediction using linear scale.

Figure 16:
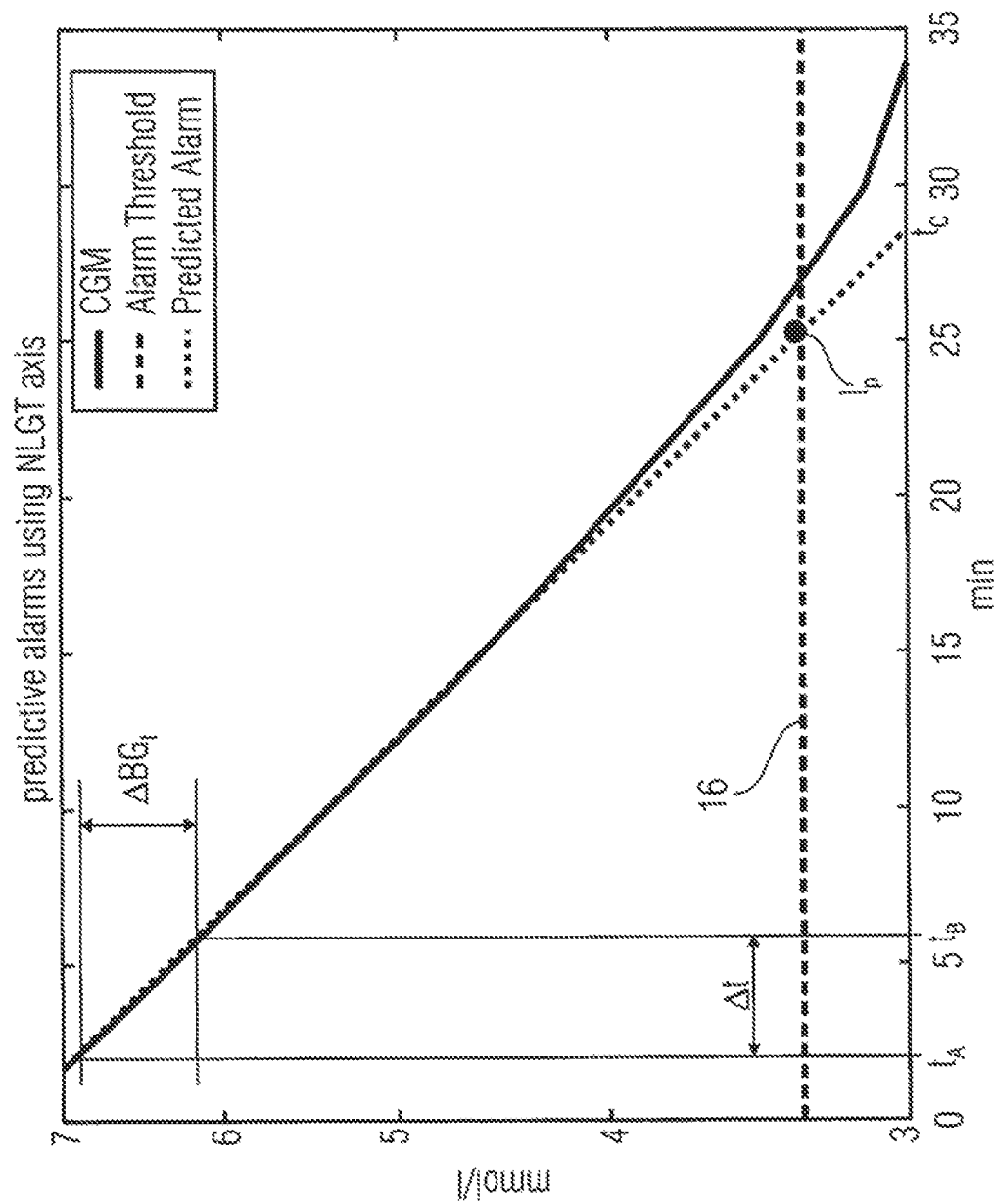

FIG. 16: illustrates an alarm prediction using NLGT scale.

Figure 17:
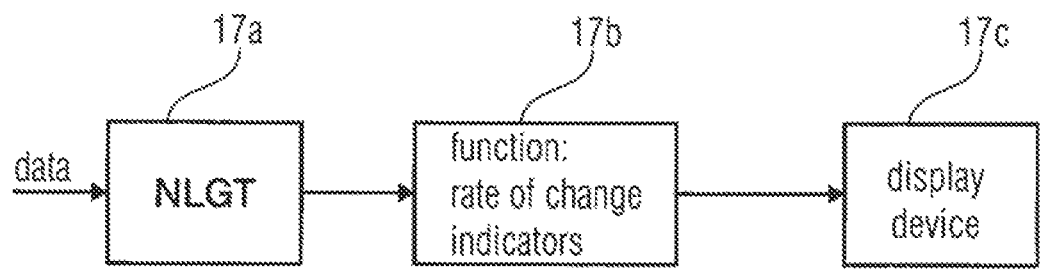

FIG. 17: illustrates a block diagram for rate of change indication using NLGT.

Figure 18:
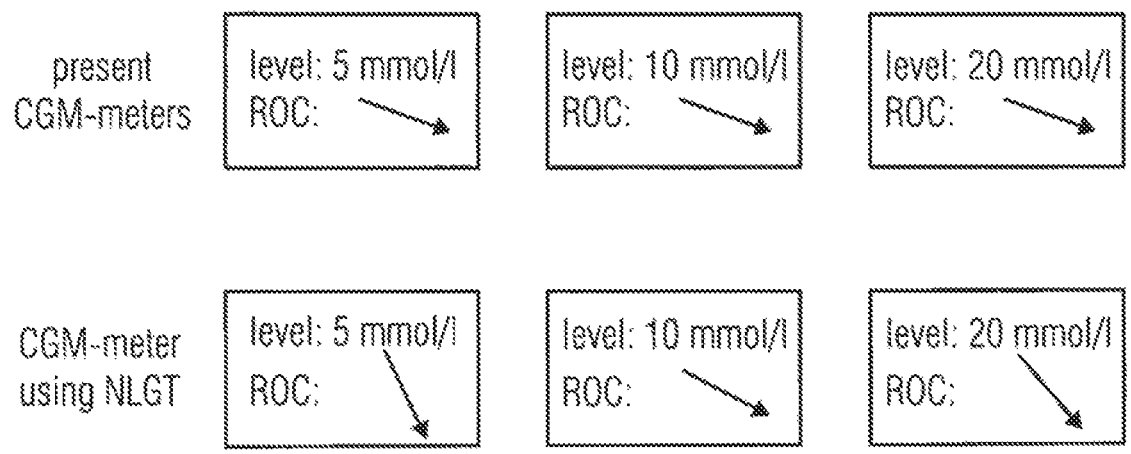

FIG. 18: illustrates an example of a blood glucose rate of change of −3 mmol/lh at different blood glucose levels presented as arrows.

Figure 19:
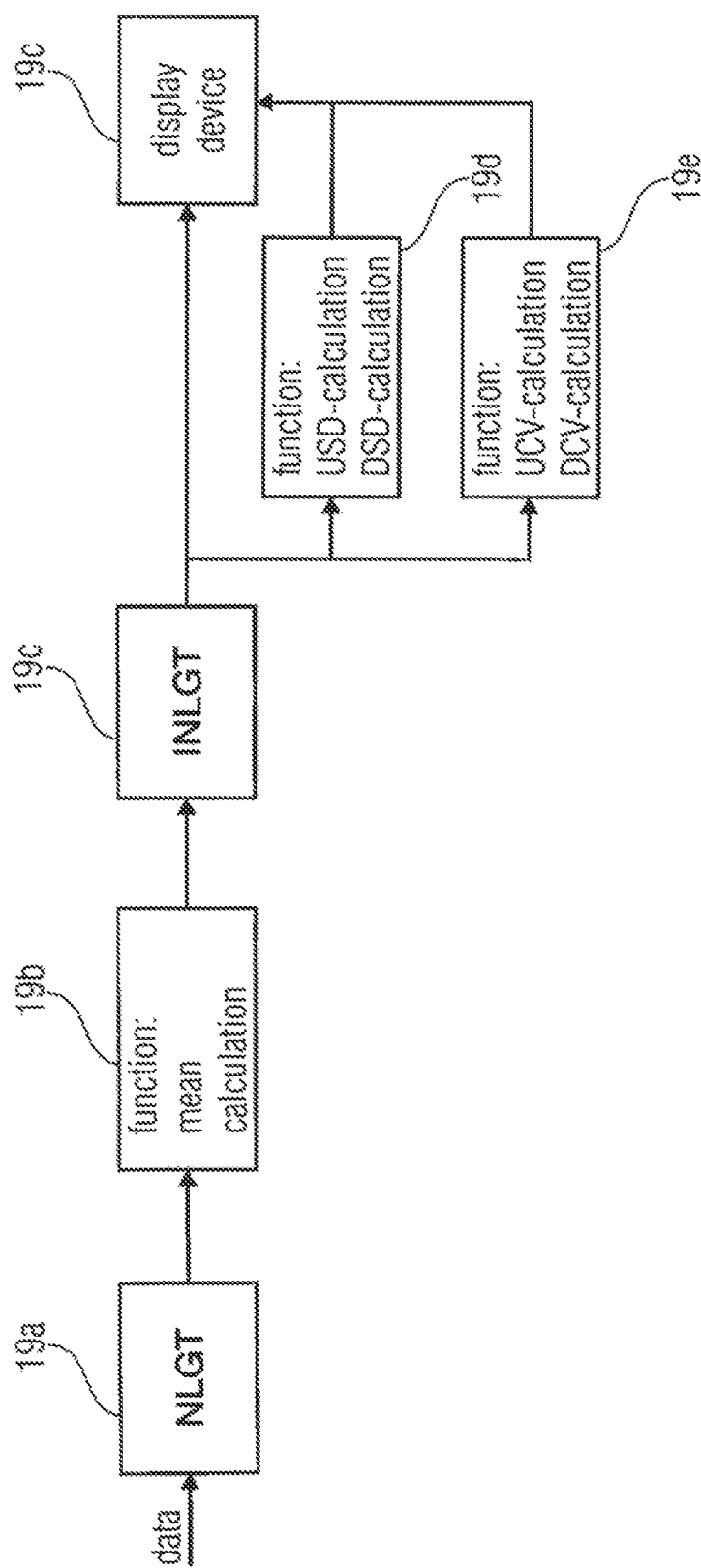

FIG. 19: illustrates a block diagram of the NLGT mean calculation, the variability measures NLGT USD/DSD and measures NLGT UCV/DCV.

Figure 20:
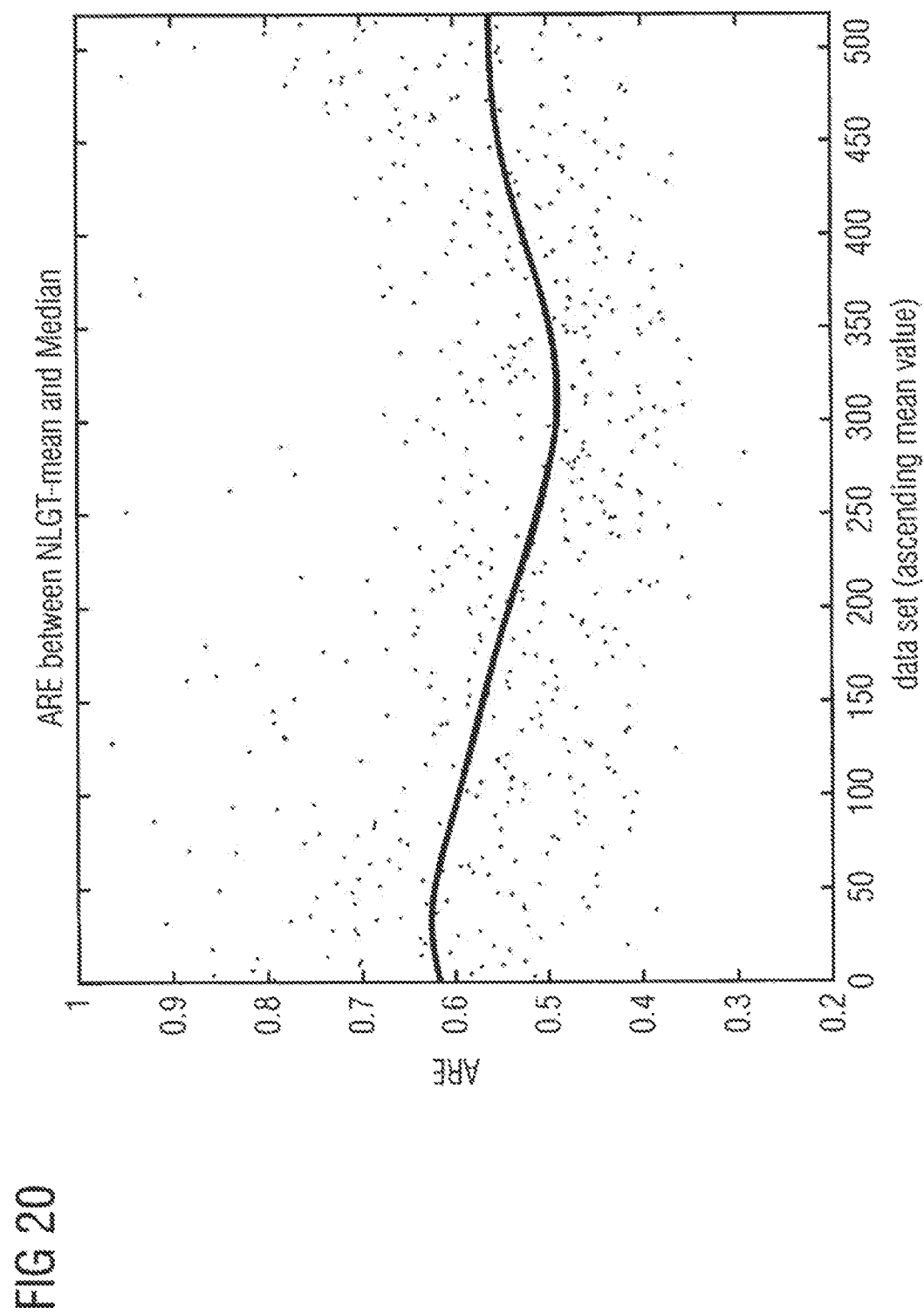

FIG. 20: illustrates a calculated ARE between the NLGT-mean and median.

Figure 21:
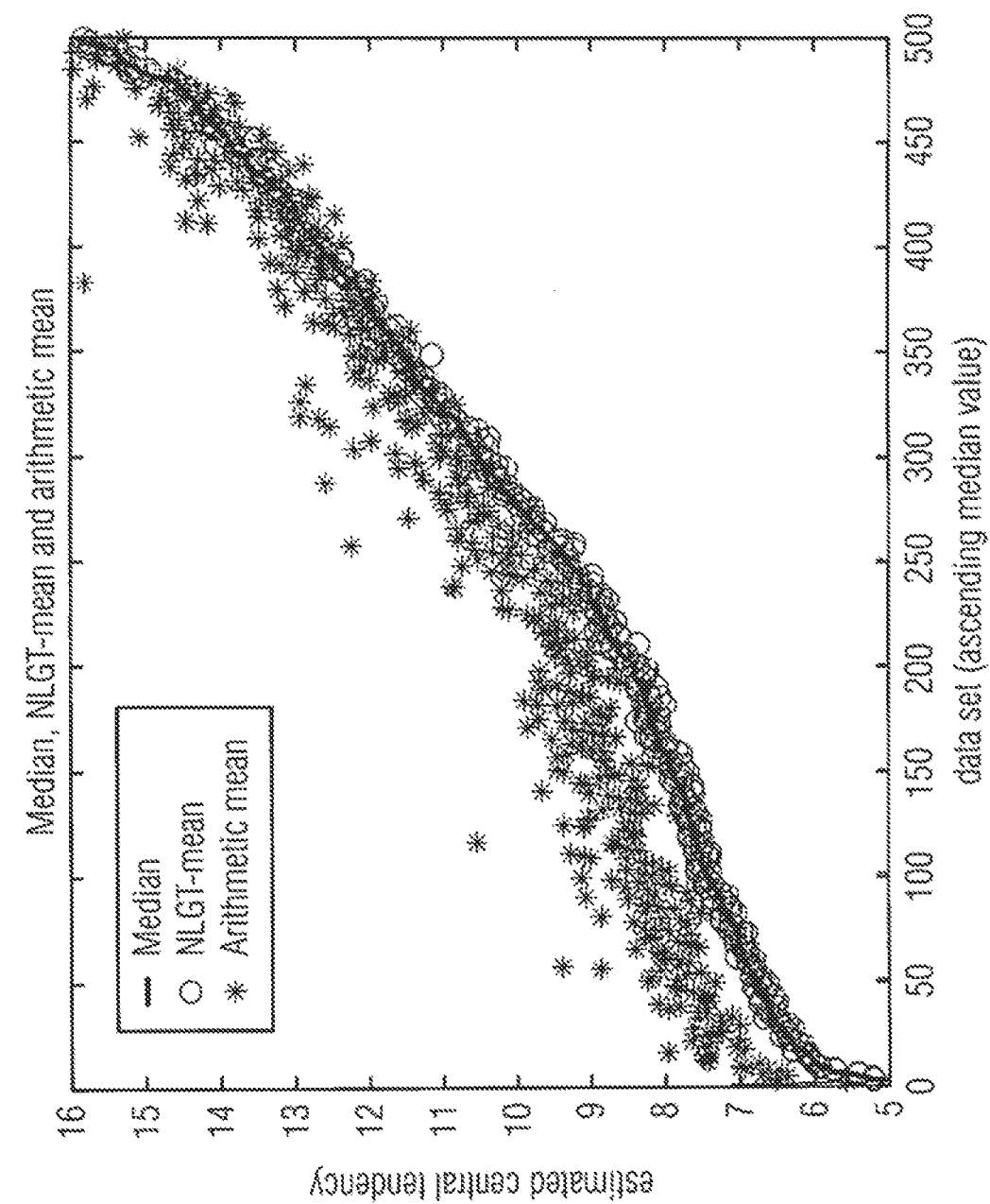

FIG. 21: illustrates point estimations of central tendency for the DCCT datasets.

Figure 22:
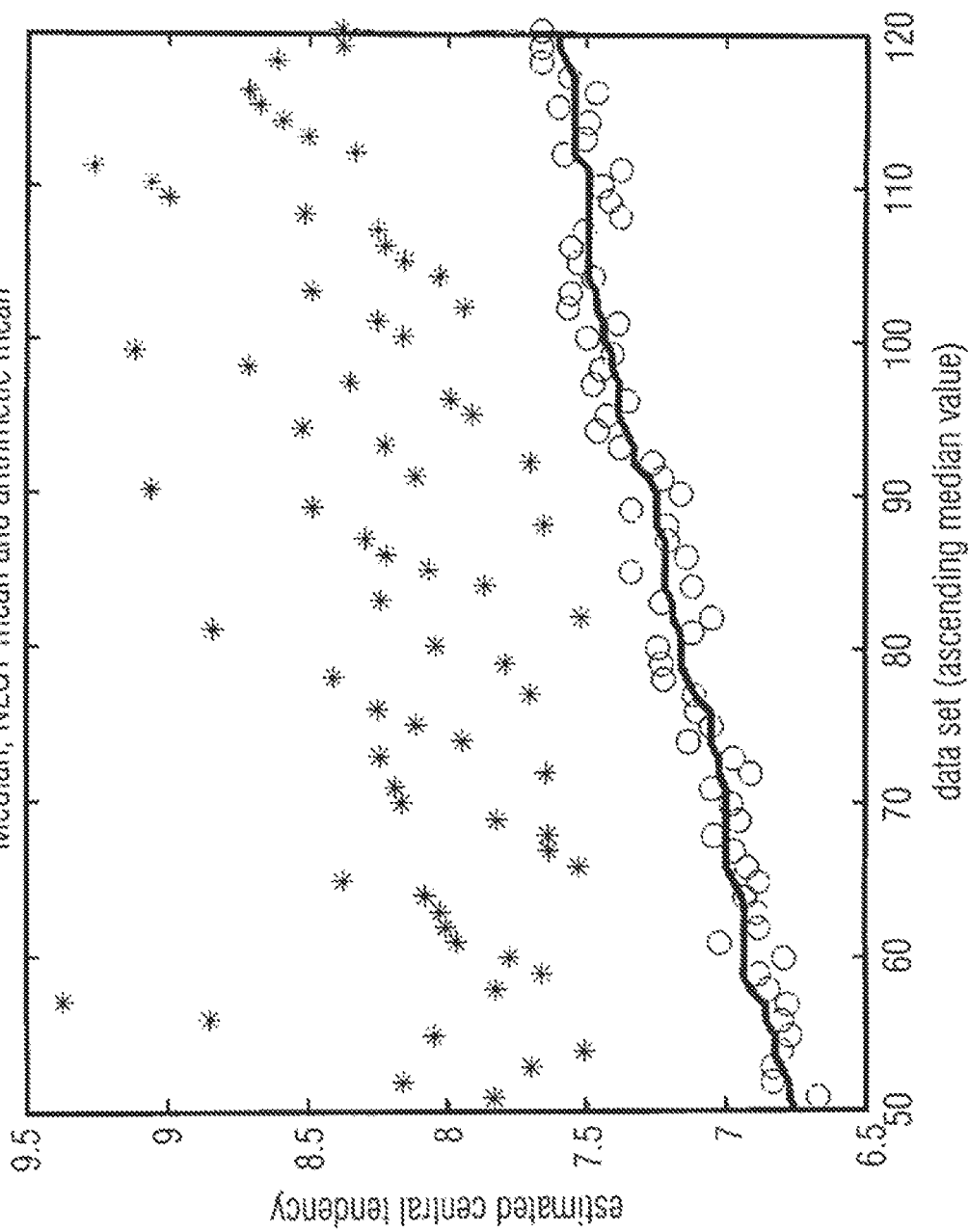

FIG. 22: illustrates point estimations of central tendency for the DCCT datasets, zoomed.

Figure 23:
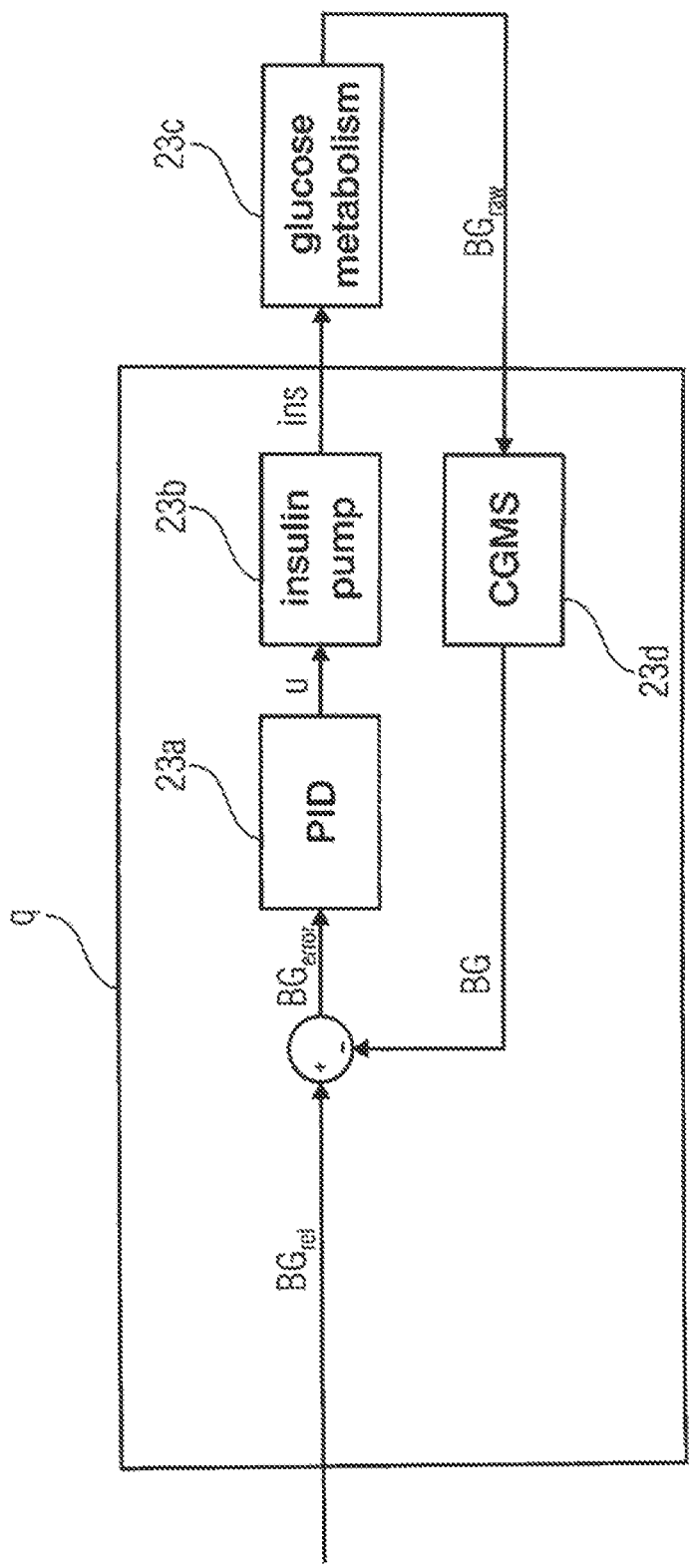

FIG. 23: illustrates a simplified example of an artificial pancreas with a closed loop or semi-closed loop control using real-time data from a continuous blood glucose sensor.

Figure 24:
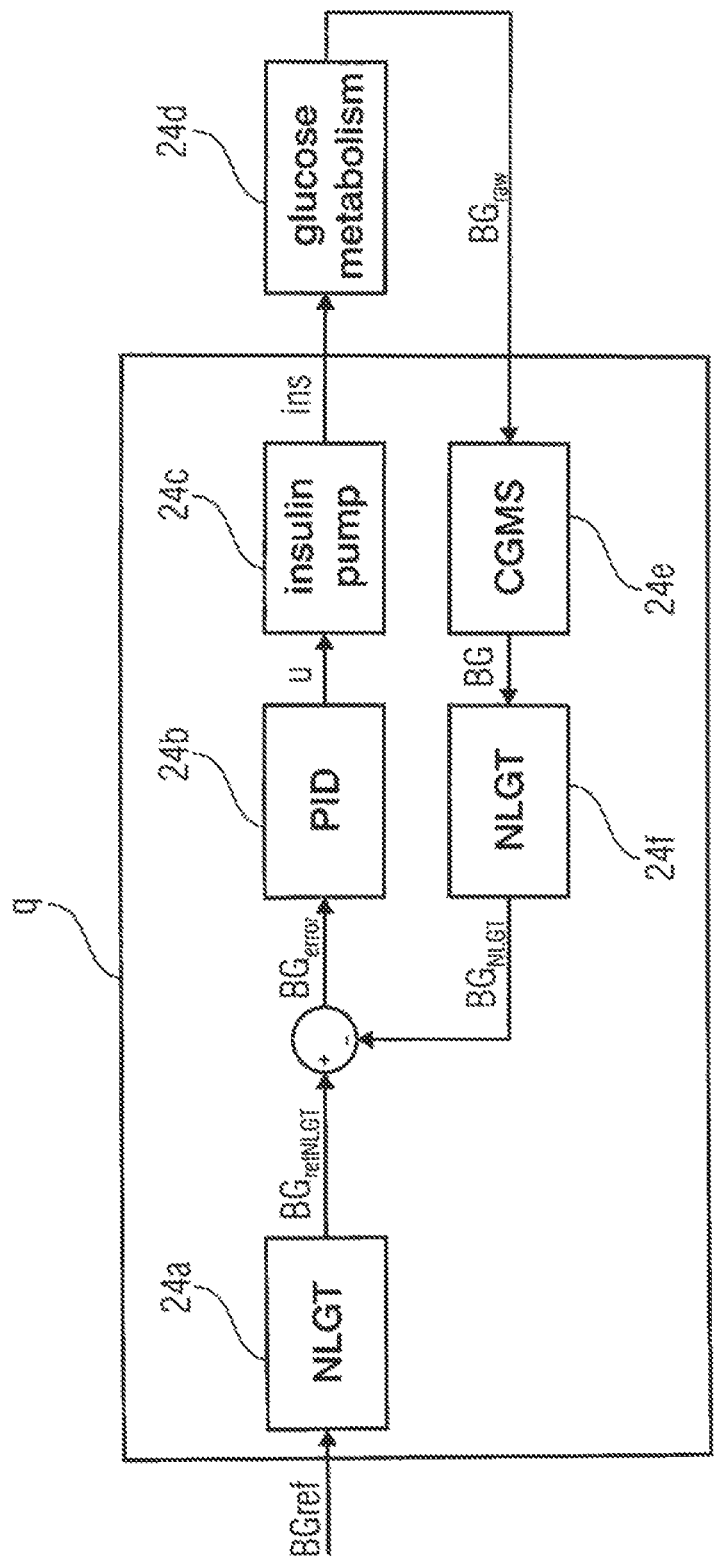

FIG. 24: illustrates a simplified example of an artificial pancreas using the NLGT transform on the reference and the actual glucose level.

Figure 25:
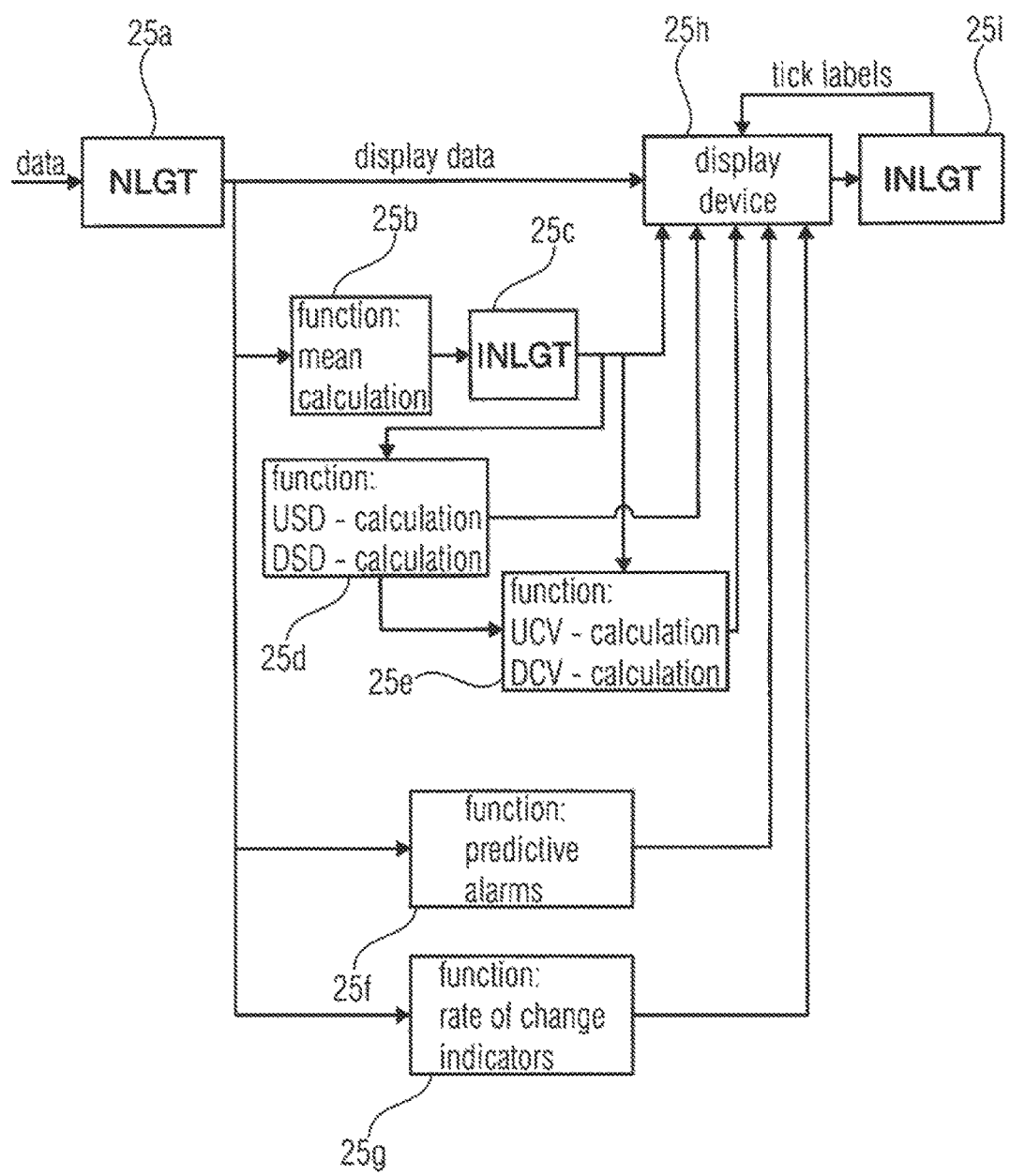

FIG. 25: illustrates a block diagram for a comprehensive apparatus containing graphical presentation using NLGT, predictive alarms using NLGT, rate of change indication using NLGT, NLGT mean calculation, the variability and risk measures NLGT USD/DSD and NLGT UCV/DCV.

DETAILED DESCRIPTION OF EMBODIMENTS

It is to be noted that the above and subsequently described aspects can be used in combination or separately from each other. Furthermore, the other different features of the invention related to the CDF smoothing, target function, generating the transform map/transform function, transforming data, universal transform for a collection of data sets, a simplified universal transform for a collection of data sets, a graphical interpretation, predictive alarms and glucose dynamics interpretation, estimation of central tendency, estimation of variability, or artificial pancreas can be used in combination or separately from each other, i.e. as alternatives, in accordance with the present invention.

Figure 1:
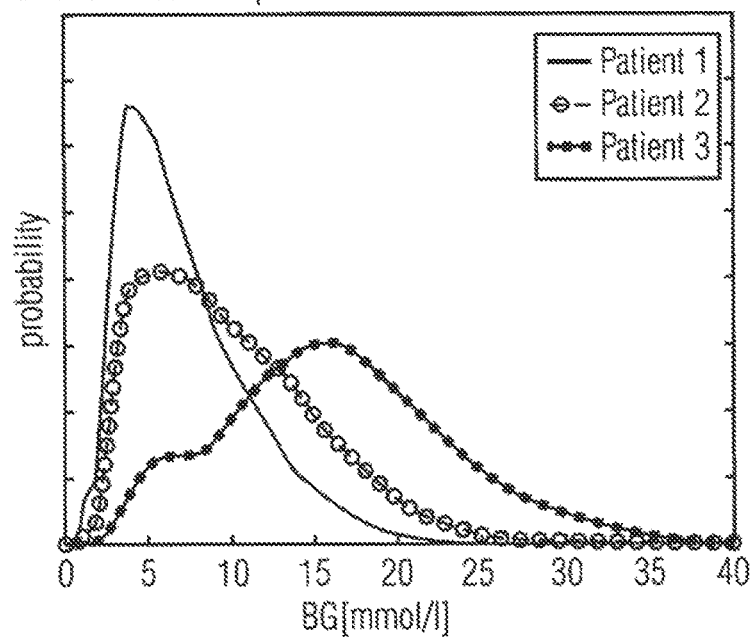

FIG. 1 illustrates PDFs for three example patients with different glucose mean values.

Figure 2:
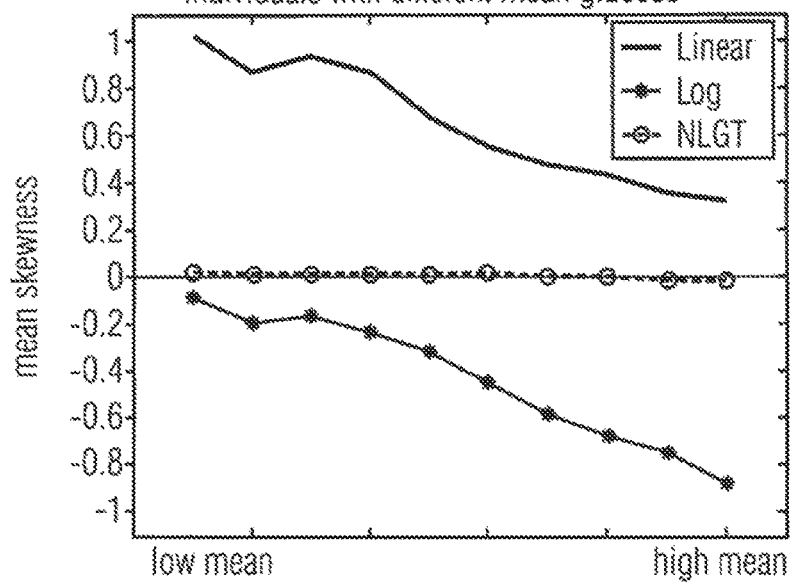

FIG. 2 illustrates a mean skewness for glucose data sets with different glucose mean values. The diagram is based on 520 data sets from the well-known DCCT study. The skewness has been calculated for each data set in the linear, log and NLGT domain.

Figure 3:
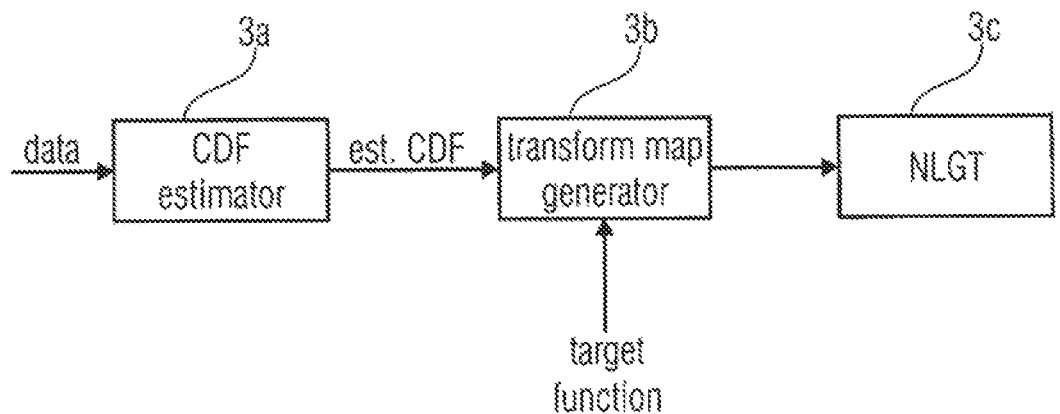

FIG. 3 illustrates a block diagram for creating a data optimized NLGT-transform.

Figure 4A:
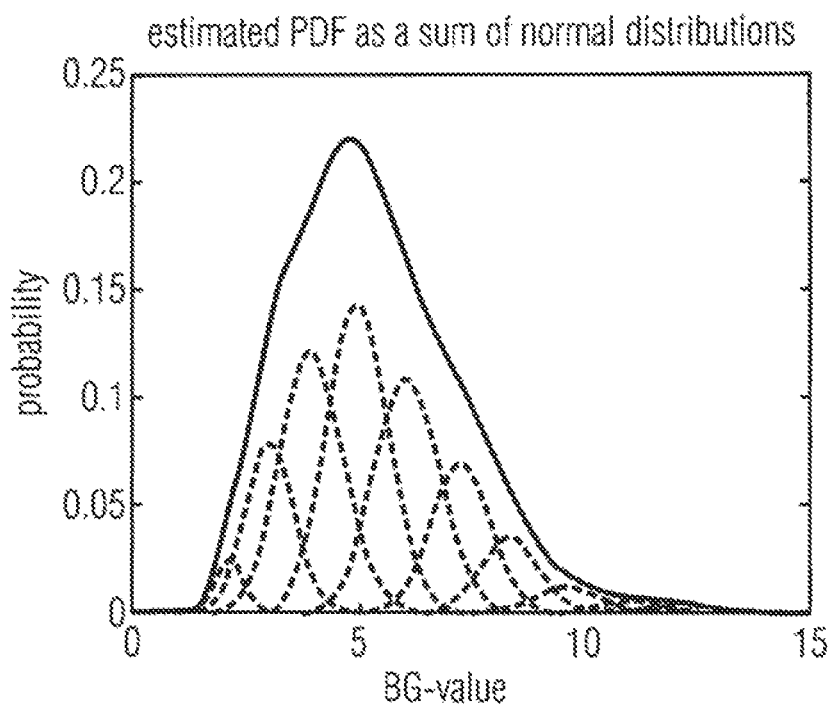

FIG. 4a illustrates an estimated PDF, as a sum of weighted normal probability density functions for each bin.

Figure 4B:
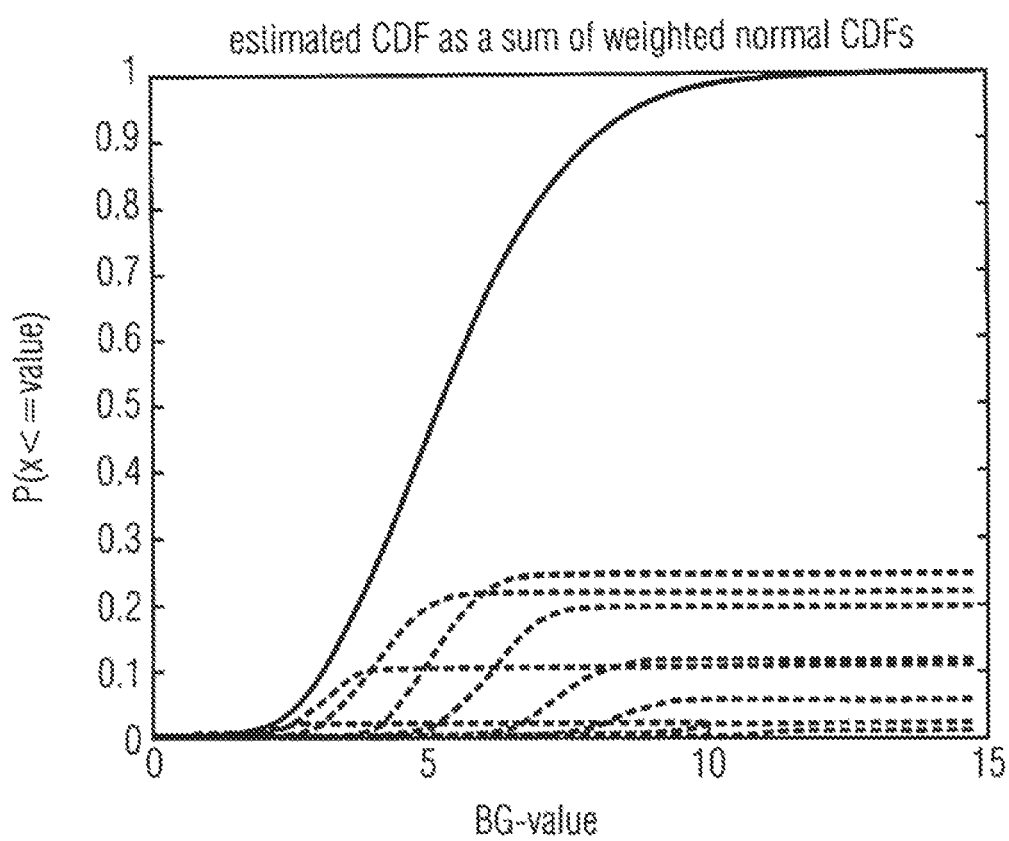

FIG. 4b illustrates an estimated CDF, as a sum of weighted normal cumulative distribution functions for each bin.

Figure 5:
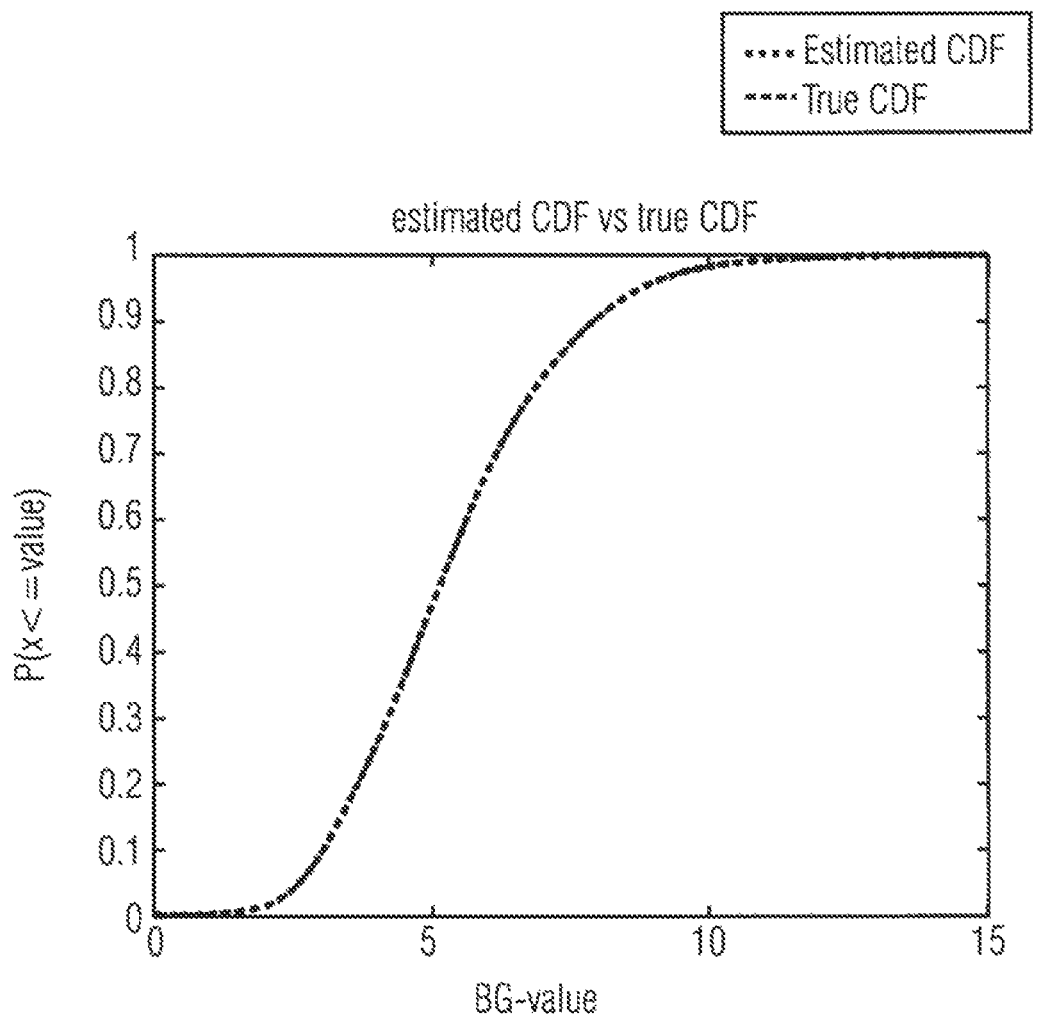

FIG. 5 illustrates an estimated cumulative distribution function, CDF, and true CDF for the data set. The estimated CDF accuracy is proven by the total overlap of the true CDF.

Figure 6:
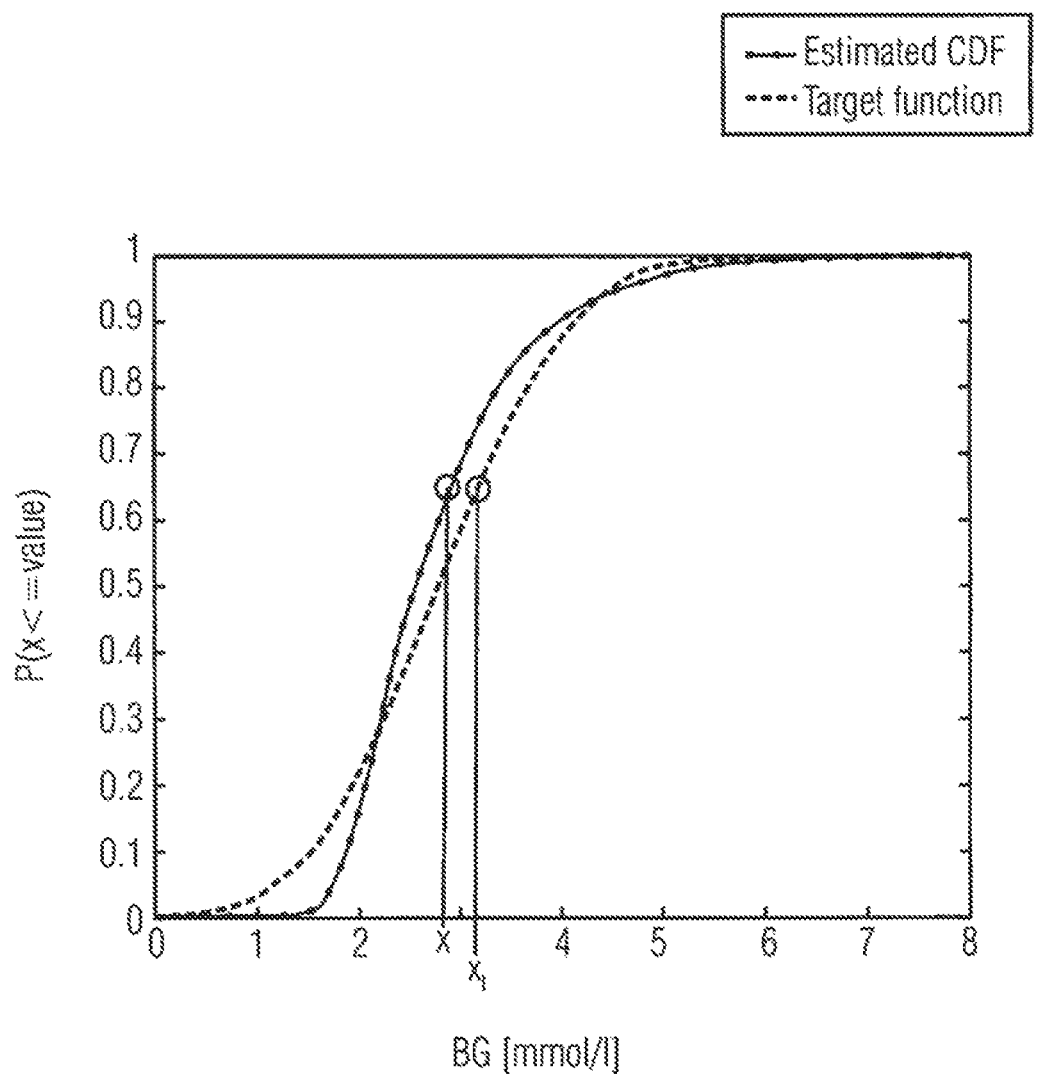

FIG. 6 illustrates an estimated CDF and target function. In the transform map, x is mapped to $x_t$.

Figure 7:
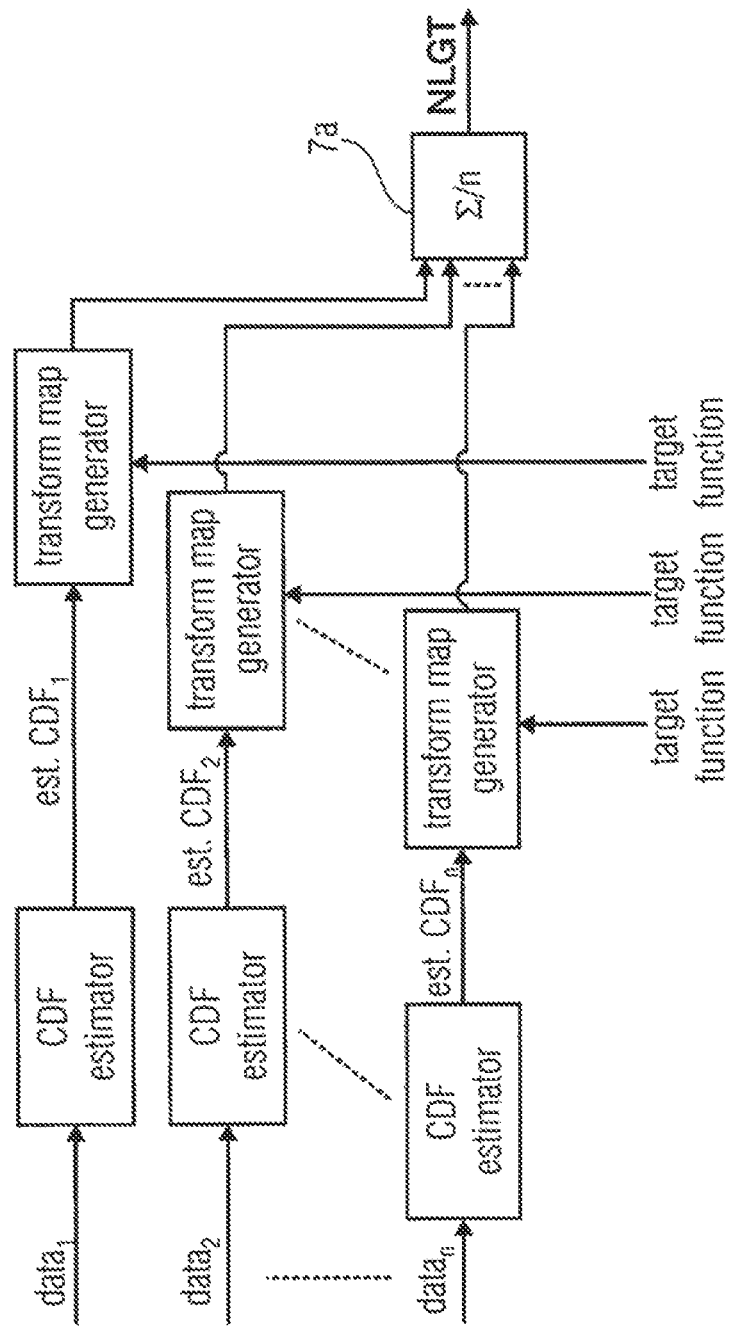

FIG. 7 illustrates a block diagram for creating a population based NLGT transform. CDF Estimator represents the method to estimate the CDF for the incoming data. Transform map Generator represents the creation of a transform map given the estimated CDF and a specific target function. 7a represents the mean calculation of the n number of transform maps.

FIG. 8 illustrates a population optimized transform based on data sets from 60 individuals from the DCCT study and the estimated Log-linear transform with a specific P and M.

FIG. 9 illustrates a block diagram for graphical presentation of data. 9a represents the transformation of glucose data to be presented. 9b represents a display device, e.g. a glucometer, a smartphone, a computer or any other monitoring device. 9c represents the inverse transformation of the tick labels to retain the glucose identity in the graphical presentation.

FIG. 10 illustrates a substitution of axis values to restore and retain the blood glucose identity in mmol/l or mg/dl.

FIG. 11 illustrates different designs of the NLGT-axis. 11a shows an implementation where the tick-marks are evenly spread with an exact distance on the y-axis and the corresponding values de-transformed and substituted. 11b shows an implementation where prioritizing the de-transformed values and placing the tick-marks almost on an exact distance. 11c shows an implementation in a non-linear way with respect to the de-transformed values.

FIG. 12 illustrates a block diagram for predictive alarms using NLGT. 12a represents the transformation of glucose data, where the transform is typically based on general glucose dynamics. 12b represents the predictive alarms algorithms. 12c represents a display device, e.g. a glucometer, a smartphone, a computer or any other monitoring device.

FIG. 13a illustrates an example of blood glucose dynamics originating from 30 type-1 diabetics, using CGM with 5 minutes sampling rate.

FIG. 13b illustrates an estimated PDF for the blood glucose dynamics in FIG. 13a.

FIG. 13c illustrates an estimated CDF for the blood glucose dynamics in FIG. 13a and the uniform target CDF.

FIG. 13d illustrates a transform map generated from the estimated CDF for the blood glucose dynamics in FIG. 13a and the uniform target CDF, shown in FIG. 13c.

FIG. 14 illustrates a schematic depiction of how non-linear glucose propagation affects alarm prediction algorithms.

FIG. 15 illustrates an alarm prediction using linear scale. The prediction is inaccurate due to the non linear propagation of glucose data.

FIG. 16 illustrates an alarm prediction using NLGT scale. The prediction in the NLGT domain is more accurate, thus improving the alarm function.

FIG. 17 illustrates a block diagram for rate of change indication using NLGT. 17a represents the transformation of glucose data, where the transform is typically based on general glucose dynamics. 17b represents the rate of change indication algorithms. 17c represents a display device, e.g. a glucometer, a smartphone, a computer or any other monitoring device.

FIG. 18 illustrates an example of a blood glucose rate of change of −3 mmol/lh at different blood glucose levels presented as arrows. Top: The presentation in the conventional linear domain. Bottom: The presentation in the NLGT domain.

FIG. 19 illustrates a block diagram of the NLGT mean calculation, the variability measures NLGT USD/DSD and measures NLGT UCV/DCV. 19a represents the transformation of glucose data. 19b represents an arithmetic mean value calculation. 19c represents the inverse transformation of the results to retain the glucose identity. 19d represents the NLGT upside and downside standard deviation calculations using the NLGT mean. 19e represents the NLGT upside and downside CV calculations using the NLGT mean and NLGT upside and downside standard deviations. 19f represents a display or indicating device, e.g. a glucometer, a smartphone, a computer or any other monitoring device.

FIG. 20 illustrates a calculated ARE between the NLGT-mean and median.

FIG. 21 illustrates point estimations of central tendency for the DCCT datasets.

FIG. 22 illustrates point estimations of central tendency for the DCCT datasets, zoomed.

FIG. 23 illustrates a simplified example of an artificial pancreas with a closed loop or semi-closed loop control using real-time data from a continuous blood glucose sensor. $BG_{ref}$=the desired glucose set-point, typically around 5-6 mmol/l; $BG_{raw}$=the actual glucose level; BG=the glucose level measured by a continuous blood glucose meter; $BG_{NLGT}$=the transformed BG signal; $BG_{refNLGT}$=the transformed $BG_{ref}$ signal. $BG_{error}$=the difference between the actual and the desired glucose signal; u=the control signal that steers the insulin pump; ins=the insulin that is infused into the glucose metabolism; 23a=the regulator system; 23b=the insulin pump; 23c=the actual glucose metabolism; 23d=the continuous glucose meter sensor; q=the artificial pancreas FIG. 24 illustrates a simplified example of an artificial pancreas using the NLGT transform on the reference and the actual glucose level. This will increase the error signal when the actual glucose level is in the hypo- or hyperglycemic range. $BG_{ref}$=the desired glucose set-point, typically around 5-6 mmol/l; $BG_{raw}$=the actual glucose level; BG=the glucose level measured by a continuous blood glucose meter; $BG_{NLGT}$=the transformed BG signal; $BG_{refNLGT}$=the transformed $BG_{ref}$ signal. $BG_{error}$=the difference between the actual and the desired glucose signal; u=the control signal that steers the insulin pump; ins=the insulin that is infused into the glucose metabolism; 24a, 24f=the NLGT transform; 24b=the regulator system; 24c=the insulin pump; 24d=the actual glucose metabolism; 24e=the continuous glucose meter sensor; q=the artificial pancreas.

FIG. 25 illustrates a block diagram for a comprehensive apparatus containing graphical presentation using NLGT, predictive alarms using NLGT, rate of change indication using NLGT, NLGT mean calculation, the variability and risk measures NLGTUSD/DSD and NLGT UCV/DCV and Poincare analysis using NLGT. 25a represents the transformation of glucose data. 25b represents an arithmetic mean value calculation. 25c represents the inverse transformation of the results to retain the glucose identity. 25d represents the NLGT upside and downside standard deviation calculations using the NLGT mean. 25e represents the NLGT upside and downside CV calculations using the NLGT mean and NLGT upside and downside standard deviations. 25f represents the predictive alarms algorithms. 25g represents the rate of change indication algorithms. 25h, represents a display device, e.g. a glucometer, a smartphone, a computer or any other monitoring device. 25i represents the inverse transformation of the tick labels in the display device to retain the glucose identity in the graphical presentation.

The theoretical research behind the present invention demonstrates that every individual has a unique glucose probability distribution that changes over time. The properties of glucose distributions depend on numerous factors. Our research has shown that DM type, DM stage, glucose control and treatment regimen have major influence on the distributions shape and asymmetry, see FIG. 1. Intuitively this can be explained by different impact of the threshold boundaries of the glucose dynamics. For instance a very well-regulated individual has a low HbA1c or a low mean glucose value, which implies many low values close to the lower boundary where physiologic counter regulatory actions may set in, but has few high values around the renal threshold. Contrary, a diabetic with high HbA1c or a high mean value experience many high values, thus in such case, the renal threshold highly influence the glucose distribution. These example individuals are on opposite sides of the glucose range or glucose scale, but all along the scale different individuals glucose data show different mean values, glucose ranges, variation and distribution patterns. Therefore, feedback to the patient from glucose measurements using traditional technologies, either from SMBG, CGM or other measuring devices is more or less biased and limits the potential benefit of self-care and treatment.

The proposed solution according to the invention presents ways to use glucose measurements in an optimized way. Enabling individually based as well as population based adjusted scales, accurate and correct statistical measures and improved aiding tools.

This entails transforming the properties of the raw glucose readings for improved use in different applications. Any set of glucose data belonging to any probability density function (PDF) could according to the invention be transformed into any advantageous and predefined target PDF function. The choice of PDF target function depends on the application in which the transform will operate.

The transform according to the invention can be created for 1 to N individuals. The transform target can be chosen as any probability density function. The transform design is based on the statistics of the dataset, or a subset of the dataset, that will be transformed. The design method comprises a number of useful steps which results in a transform map or a transform function that is used to transform the data set into an arbitrary distribution.

FIG. 3 illustrates an apparatus for processing a set of data values, a data value representing a physiological measure of a body fluid at a time instant. The apparatus comprises an estimated probability function calculator which is also mentioned in FIG. 3 as "CDF estimator" 3a. The estimated probability function calculator is configured to calculate an estimated probability function associated with a set of data values or "data" input into block 3a. Furthermore, the apparatus for processing a set of data value comprises a transform calculator or "transform map generator" 3b for calculating a non-linear transform rule using a predetermined target probability function which is input into the transform calculator or which is actually already stored in the transform calculator, so that the probability function of a set of transformed data values is closer to the target probability function than the estimated probability function associated with the set of data values. The apparatus for processing the set of data values furthermore comprises a transformer 3c for applying the transform rule calculated by the transform calculator 3b to the set of data values or to at least one further data value not included in the set of data values and sampled at the different time instants from the time instant for the set of data values to obtain at least one transformed value representing the physiological measure at the output of the transformer 3c which is also named "NLGT" where NLGT stands for non-linear glucose transform.

Additionally, the apparatus may comprise a device 24 for using the at least one transformed value for controlling a device for dosing a medication in a closed or open loop configuration or for processing 25 to obtain a visual, audible, tactile, mechanic, electro or magnetic indication of a physiological characteristic of the body, from which the set of data values or the further data values have been taken. The physiological characteristics can be a glycemic characteristic related to a blood glucose measurement or can also be any other physiological characteristic such as a concentration of any other substance apart from glucose in the blood, urine, lymphatic liquid or any other liquids of a body of a human being or an animal. Specifically, the transform calculator 3b is configured for calculating a function value of the estimated/actual probability function of an actual/estimated data value and for calculating a function value of the target probability function for a transformed value, wherein the transform value is selected by the transform calculator 3b, so that the function value of the actual/estimated probability function is equal to the functionality of the target probability function. In this context, reference is made to the equality given in equation (14).

CDF Smoothing

Each dataset of glucose readings contains characteristic statistics that originates from the individual from which the data originate. An arbitrary dataset exhibit an unknown distribution, often not normally distributed, thus the distribution has to be estimated in order to generate the transform. Advantageously the cumulative distribution function, CDF, is used to describe the distribution statistics. In order to make the transform accurate, the estimated CDF has to be not only accurate, but advantageously also exhibit a smooth function with no discontinuities. Smoothing can be performed in different ways. However, an improved method to find, an accurate, smooth estimation of the CDF for a dataset, regardless of distribution, has been developed.

3a in FIG. 3 represents the method to estimate the CDF for the incoming data. 3b represents the creation of a transform map given the estimated CDF and a specific target function. 3c represents the complete data optimized transform. The following method is represented as block 3a in FIG. 3. This method is based on estimating a true distribution function by the sum of a finite number of weighted normal distributions, see FIGS. 4a and 4b. By defining k number of bins, where each bin represents a certain value range and the bins overlap each other by a certain percentage, each value in the dataset can be placed in the bin or bins that cover the value range in which the values are situated. After doing this, each bin contains a certain number of data points from the dataset. The data points in each bin are assumed to belong to a normal distribution that can be estimated by for example the Maximum Likelihood method. The estimated normal distribution for each bin are weighted and added together to form the estimated distribution function for the dataset. A normal distribution, $N(\mu,\sigma^2)$, has got the following probability density function:

$$f(x \mid \mu, \sigma^2) = \frac{1}{\sigma\sqrt{2\pi}} e^{-\frac{(x-\mu)^2}{2\sigma^2}} \quad (1)$$

where $\mu$ is the expected value and $\sigma$ is the standard deviation. If the data points, $[x_1, x_2, \ldots, x_n]$, in each bin are assumed to be independent and equally distributed, the maximum-likelihood function for each bin can be written as $$f(x_1, x_2, \ldots, x_n \mid \mu, \sigma^2) = \prod_{i=1}^{n} f(x_i \mid \mu, \sigma^2) = \left(\frac{1}{2\pi\sigma^2}\right)^{\frac{n}{2}} \cdot e^{\left(\frac{\sum_{i=1}^{n}(x_i-\mu)^2}{2\sigma^2}\right)} \quad (2)$$

By maximizing equation (2) with respect to $\mu$ and $\sigma$, the maximum-likelihood estimation for these parameters are given as the solution to $$\frac{\delta}{\delta\mu}\left[\left(\frac{1}{2\pi\sigma^2}\right)^{\frac{n}{2}} \cdot e^{\left(\frac{\sum_{i=1}^{n}(x_i-\mu)^2}{2\sigma^2}\right)}\right] = 0 \quad (3)$$

and $$\frac{\delta}{\delta\sigma}\left[\left(\frac{1}{2\pi\sigma^2}\right)^{\frac{n}{2}} \cdot e^{\left(\frac{\sum_{i=1}^{n}(x_i-\mu)^2}{2\sigma^2}\right)}\right] = 0 \qquad (4)$$

Straight forward calculations give the parameter estimations $$\hat{\mu} = \bar{x} = \frac{1}{n}\sum_{i=1}^{n} x_i \qquad (5)$$

$$\hat{\sigma}^2 = \frac{1}{n}\sum_{i=1}^{n}(x_i - \hat{\mu}) \qquad (6)$$

Given an estimate of $\mu$ and $\sigma$ for the data in each bin, a normal distribution, $f_i(x)$, can now be defined for each bin. Further, for any probability density function it will hold that $$\int_{-\infty}^{\infty} f(x)dx = 1 \qquad (7)$$

which implies that the estimated normal distribution for each bin has to be weighted so that $$\int_{-\infty}^{\infty} \sum_{i=1}^{k} p_i \cdot f_i(x) dx = 1 \qquad (8)$$

To fulfill equation (8) the weights can be chosen as $$p_i = \frac{n_i}{\sum_{i=1}^{k} n_i} \qquad (9)$$

in which $n_i$ represents the number of samples in each bin. Given the probability density function, $f_i(x)$, and the weight, $p_i$, for each bin the estimated probability density function for the dataset is now defined as $$\tilde{f}(x) = \sum_{i=1}^{k} p_i \cdot f_i(x) \qquad (10)$$

see FIG. 4a. By defining the probability function for each bin as a cumulative distribution function, which for a normal distribution, $N(\mu,\sigma^2)$, is given by $$F(x;\mu,\sigma^2) = \frac{1}{2}\left[1 + \frac{2}{\sqrt{\pi}}\int_{0}^{\left(\frac{x-\mu}{\sigma\sqrt{2}}\right)} e^{-t^2} dt\right] \qquad (11)$$

the estimated cumulative distribution is now given as a weighted sum of normal distributions as $$\tilde{F}(x) = \sum_{i=1}^{n} \frac{p_i}{2}\left[1 + \frac{2}{\sqrt{\pi}}\int_{0}^{\frac{x-\mu_i}{\sigma_i\sqrt{2}}} e^{-t^2} dt\right] \qquad (12)$$

see FIG. 4b. Hence, equation (10) and equation (12) give estimates of the true PDF or the true CDF respectively, i.e. the method can be performed in ether the PDF domain or in the CDF domain. The expressions (10) and (12) give excellent estimates of the data sets true PDF or CDF, regardless of its shape, and form a smooth curve which is advantageous for the transform. FIG. 5 shows a CDF estimated by the described method compared to the true CDF for a data set. The estimated CDF accuracy is proven by the total and exact overlap of the true CDF.

Figure 4C:
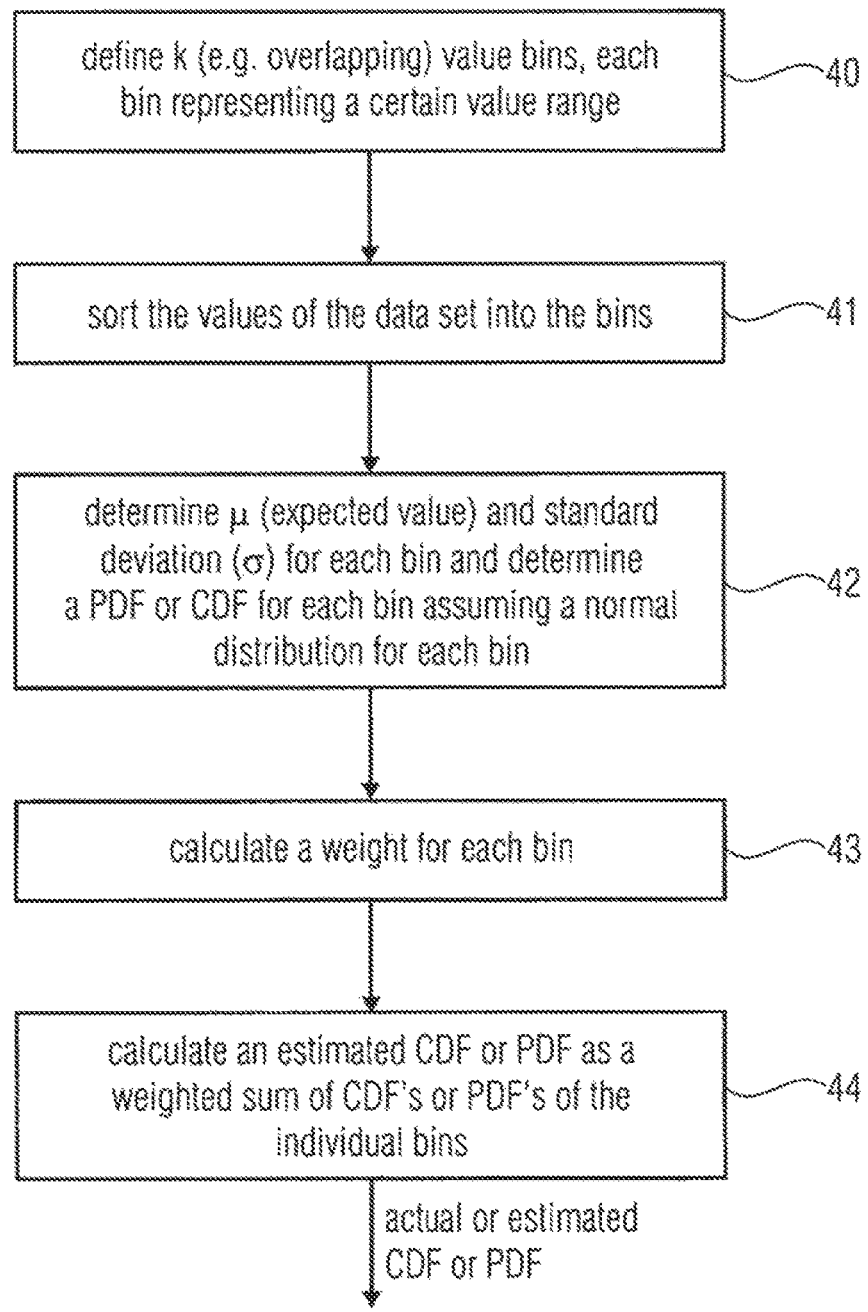

FIG. 4c illustrates a flowchart for illustrating an implementation of the estimated probability function calculator 3a of FIG. 3. In a step 40, k value bins are defined, where the value bins can optionally be overlapping, and where each bin represents a certain value range which is different from bin to bin as illustrated in FIG. 4a or 4b at the x axis. In a step 41, the values of the data set are sorted into the bin.

In step 42, expected values $\mu$ for each bin and a standard deviation a far each bin are determined, and a CDF or PDF for each bin is determined where it is assumed that there is a normal distribution for each bin. Then, in step 43, the weight for each bin is calculated such as by using equation (9). In a final step 44, an estimated cumulative distribution function or an estimated probability density function is calculated as a weighted sum of the cumulative distribution functions or the estimated probability functions of the individual bins. In step 44, equation (12) can be applied. Hence, step 44 results in an estimated or "actual" cumulative distribution function for the actual data set, which is to be transformed into a transform domain by the transform map generator 3b in FIG. 3. Hence, step 44 results in the output of block 3a in FIG. 3, which is, at the same time, the input into block 3b, i.e., the transform map generator or "transform calculator"

Target Function

The transform method according to the invention involves a transform target function. This transform target function, in the form of an CDF, needs to be defined, here denoted $F_{target}(x)$. After transforming data using the transform, the data will now belong to the distribution $F_{target}(x)$ regardless of what distribution the data originated from. What $F_{target}(x)$ to use depends on the application and the embodiment in which the transform will operate. E.g. when calculating statistics the target function is advantageously set as $$F_{target}(x;\mu,\sigma^2) = \frac{1}{2}\left[1 + \frac{2}{\sqrt{\pi}}\int_{0}^{\left(\frac{x-\mu}{\sigma\sqrt{2}}\right)} e^{-t^2} dt\right] \qquad (13)$$

i.e. a normal-distribution. This choice of $F_{target}(x)$ will imply, that the transformed data will be normally distributed as $N(\mu,\sigma^2)$, which will facilitate statistical calculations. In other embodiments $F_{target}(x)$ may be chosen as any cumulative distribution function that suits the application.

Generating the Transform Map/Transform Function

The transform according to the invention takes a value, x, and transforms it to a corresponding value, $x_t$, in the transform domain. Given an estimated CDF for a dataset, $\tilde{F}(x)$, and a target function, $F_{target}(x_t)$, which is the desired CDF for the data in the transform domain, the transform according to the invention can now be calculated by defining the following equality $$F_{target}(x_t) = \tilde{F}(x) \qquad (14)$$

For a given x it is now possible to solve the corresponding transform value $x_t$, see FIG. 6. By defining a set of x-values as $$X=[x_1,x_2,\ldots,x_n] \quad (15)$$

where the values are equidistantly spread, covering a range of the blood glucose space, and solving equation (14) for all values in X, a transform map is created. This creation of the transform map is represented by block 3b in FIG. 3. Each x-value in the transform map has got a corresponding transform value as $$TM = \begin{pmatrix} x_1, x_2, \ldots, x_n \\ x_{t1}, x_{t2}, \ldots, x_{tn} \end{pmatrix} \quad (16)$$

The resolution of the transform map is determined by the size of n and the range the transform covers. The resulting transform is represented by block 3c in FIG. 3.

Transforming Data

The transform according to the invention can be used either as a lookup-table or be converted into a transform function. When using the transform in the form of a lookup-table, the value to be transformed, $x_{in}$, is compared to the x-values in the transform map. The transform value, $x_t$, in the transform map that has the corresponding x-value, x, that is closest to $x_{in}$ is used to represent the transformed value. The same method is applied when de-transforming data from the transform domain to the real domain.

By fitting a polynomial of degree n to the transform map a transform function can be defined. Given a value, $x_{in}$, the transformed value will now be defined as $$x_t = \kappa_n \cdot x_{in} \cdots + \cdots \kappa_1 \cdot x_{in} + m \quad (17)$$

Since the transform function often is of higher order, the inverse transform has to be solved numerically, e.g. with the Newton-Raphson or similar method. The transformation and the inverse transformation of data using either a transform map or a transform function is represented in all block diagrams by the block NLGT and INLGT respectively.

FIG. 9b illustrates implementations of the transform calculator 3b in FIG. 3. In the first implementation 94, the transform map is generated and stored in a look-up table. Alternatively, the transform map can be further processed by step 95, where an analytical function such as a polynomial function is approximated to the transform map. This results in an analytic function for the transform rule where the polynomial parameters, i.e., the weighting parameters $k_i$ of equation 17 are stored in a memory to be used by the transformer. In an implementation, the transformer 3c is configured for storing the transform rule in a look-up table or as a set of parameters as illustrated at 94 and 95, and the transformer is additionally configured for recalculating a new transform rule in accordance with an event, where the event may comprise a user input, a timer expiration, a probability control check resulting in a deviation above a deviation threshold of the actual probability function for an actual set of values in an earlier probability function of an earlier set of values on which the stored transform rule is based, or a randomly generated event. In response to such an event, the apparatus illustrated in FIG. 3 or in other figures is configured to re-calculate the new transform rule and to store the new transform rule for usage by the transformer. Then, the procedure illustrated in FIG. 4a or illustrated in FIG. 13b can be newly performed to finally obtain a new transform rule where, typically, the same target function is used in the (initial) calculation of the transform rule and the (later) re-calculation of the transform rule.

As discussed, it is advantageous to use a cumulative distribution function as the target probability function and to calculate the cumulative distribution function as the actual or estimated probability function. In an implementation, the Gaussian normal distribution is used as the target probability function. In an alternative implementation, a uniform probability distribution over a defined value range is used as the target probability function, and, as discussed later on, an alarm indication for indicating an alarmed state is generated depending on the threshold, where an alarm state is indicated in any physical way, when the transformed further data value exceeds a maximum transformed threshold or is below a minimum transformed threshold, or in which the apparatus further comprises an inverse transformer for transforming the transformed further data value into a non-transformed domain, and where the alarm indicator is configured for generating an alarm, when the first transform data value exceeds the maximum threshold or is below a minimum threshold.

In a further implementation, the transformer comprises an interpolator illustrated at 90 in FIG. 9c. The interpolator is for interpolating the at least one further value or data value not coinciding with a stored, non-transformed value using at least one stored transformed value associated with a stored non-transformed value being closest in value to the further value or the data value and using an interpolation rule. In an implementation, a measurement value 91 is input, where the measurement value does not coincide with stored values of the transform map. In a step 92, a search for stored neighbors to the measurement value 91 is performed, where, in principle, one neighbor would be sufficient for an extrapolation as a specific form of an interpolation, but where, in a further implementation, two neighbors are searched, so that a true interpolation between these neighbors can be performed. Then, in step 93, the transformed values for the two neighbors are retrieved from a look-up table where the transform map is stored. Then, in step 90 of FIG. 9c, an average of the retrieved values is calculated, where this average can be a straightforward average where the two neighbors are added together and where the sum of the two neighbors is divided by 2. Alternatively, a weighted average of the retrieved values can be calculated, where the weighting factors reflect the situation, that the measurement value is closer to one neighbor or the other neighbor. If the measurement value was closer to one neighbor, then this neighbor would be weighted with a higher weighting factor compared to the other neighbor where the measurement value is spaced apart by a higher distance. Then, the transformed measurement value is obtained.

Naturally, an interpolation is not necessary when the transform rule is implemented as a parameterized curve, such as a log/lin transform (equation 18) or when the transform rule is represented by a selection of weighted polynomials, in which the weighting factors for the polynomials have been found by a matching operation.

Universal Transform for a Collection of Datasets

A transform map customized for n individuals can be created by generating a transform map for each individual's data and then calculating the average transform map of these n transform maps. See FIG. 7 where block 7a represents the mean calculation of the n number of transform maps. The functions of the other blocks are similar as in FIG. 3. By creating a transform based on data obtained from a number of individuals, a general transform adapted to a population is obtained. This transform does not perform optimally at the individual patient level, since it is based upon a number of individual's different statistics, but has the advantage that it covers general statistics for a given population of diabetics. For example, one type of glucometer can display and present glucose data and statistics optimized for a population having type 1-diabetes, and another type of glucometer can be optimized for a population having type 2-diabetes.

A Simplified Universal Transform for a Collection of Datasets

A transform customized for n individuals can also be implemented as a general and simplified low complexity transform for blood glucose data. This saves computing power and may be advantageous e.g. in glucose meters with limited computing capacity. By creating such a transform, based on a given population, it demonstrates that this average transform resembles a combination of a log-function and a linear function. Therefore, it can be estimated with reasonable accuracy using a log-linear-transform, see FIG. 8a. Such an estimation can be written in the form $$x_g = P \cdot K(x_{in}) \cdot \ln(x_{in}) + (1-K(x_{in})) \cdot x_{in} \qquad (18)$$

where P is a scale factor that is used as a tuning parameter and K(x) is a weight function defined by $$K(x) = 1 - \ln(z(x)) \qquad (19)$$

in which z(x) is defined as $$z(x) = \frac{e-1}{M-1} x + \left(1 - \frac{e-1}{M-1}\right) \qquad (20)$$

Hence, M is a tuning parameter which defines at which rate the transform will fade from a tog-transform to a linear transform as the values of x increases. FIG. 8 represents a population optimized transform based on data sets from 60 individuals from the DCCT study compared to, the estimated Log-linear transform with a specific P and M. e is the Euler constant (2.7 . . . ) or an approximation thereof. In an embodiment, the approximation of e may be between 2.5 and 2.9 or advantageously between 2.6 and 2.8.

Figure 8A:
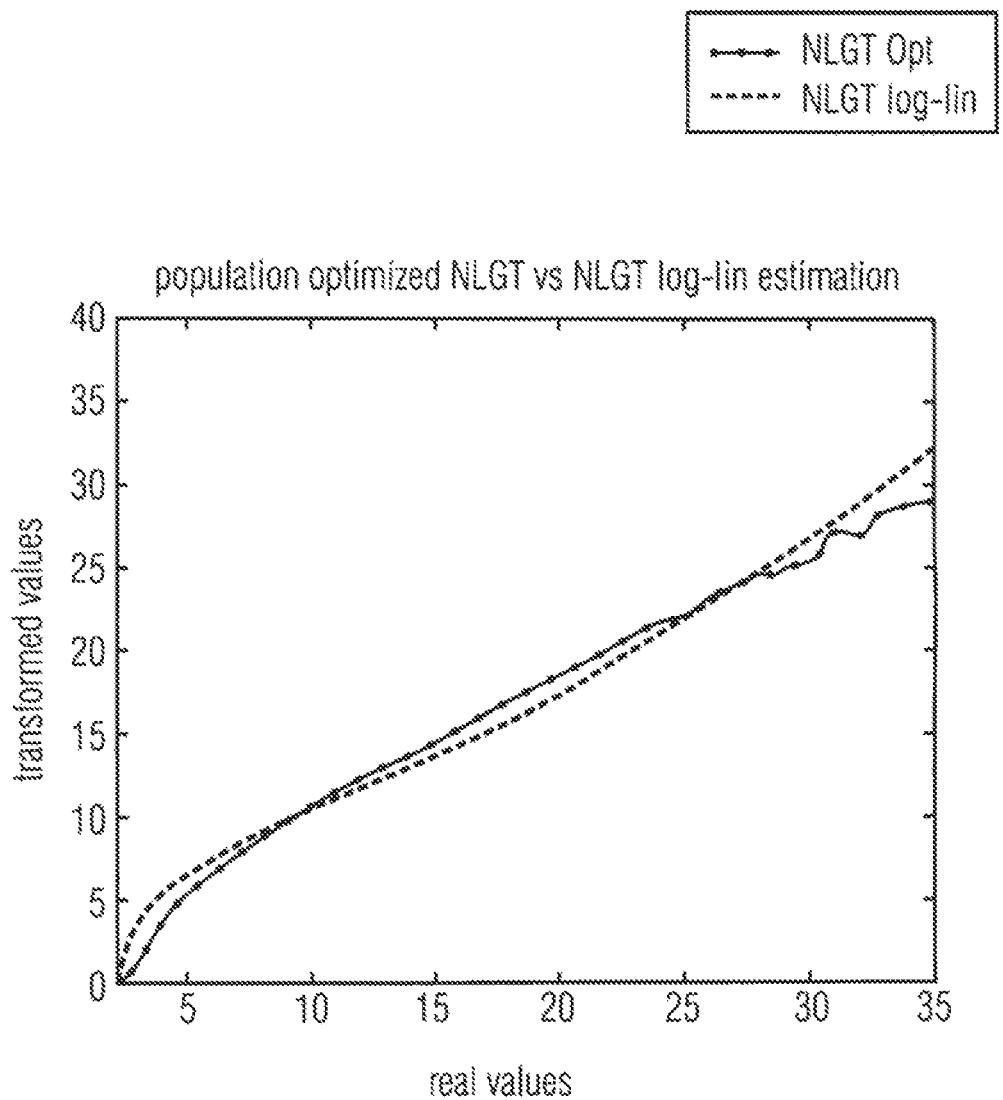
FIG. 8b is a schematic block chart for illustrating an implementation of the log/lin transformer.
FIG. 8c is a diagram illustrating the logarithmic characteristic, the linear characteristic and the blending of both characteristics in a large mutual influence region extending over almost the whole value range of the real values.
FIG. 8d illustrates an implementation of the transformer when being implemented for applying a parametric formula.
FIG. 8e illustrates an advantageous implementation of the apparatus for processing a glycemic data in accordance with one aspect of the invention.
Figure 8B:
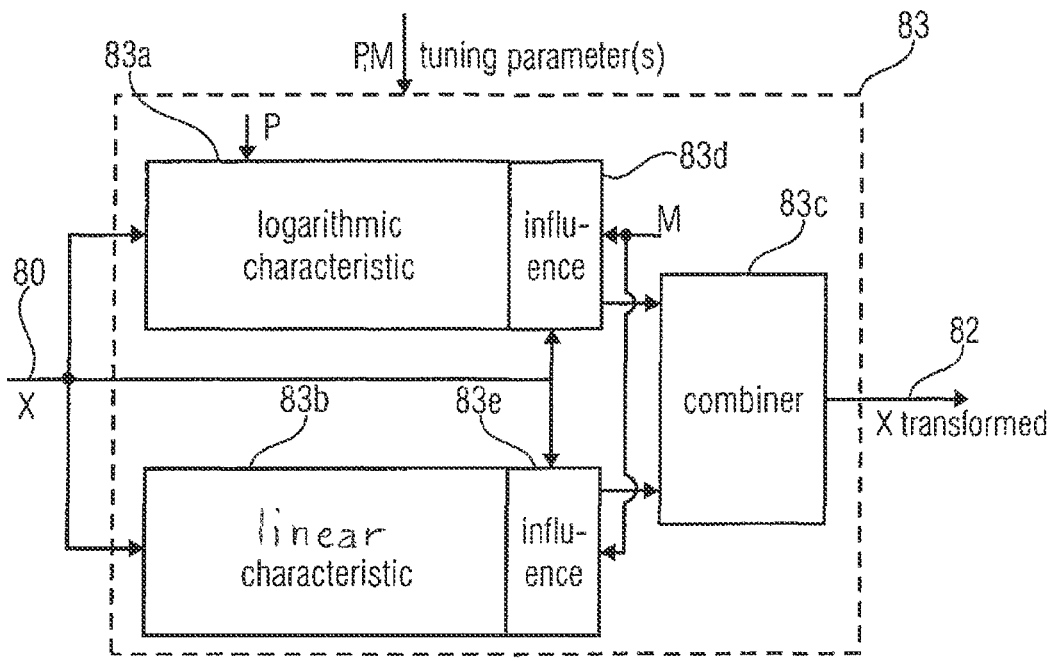
Figure 8C:
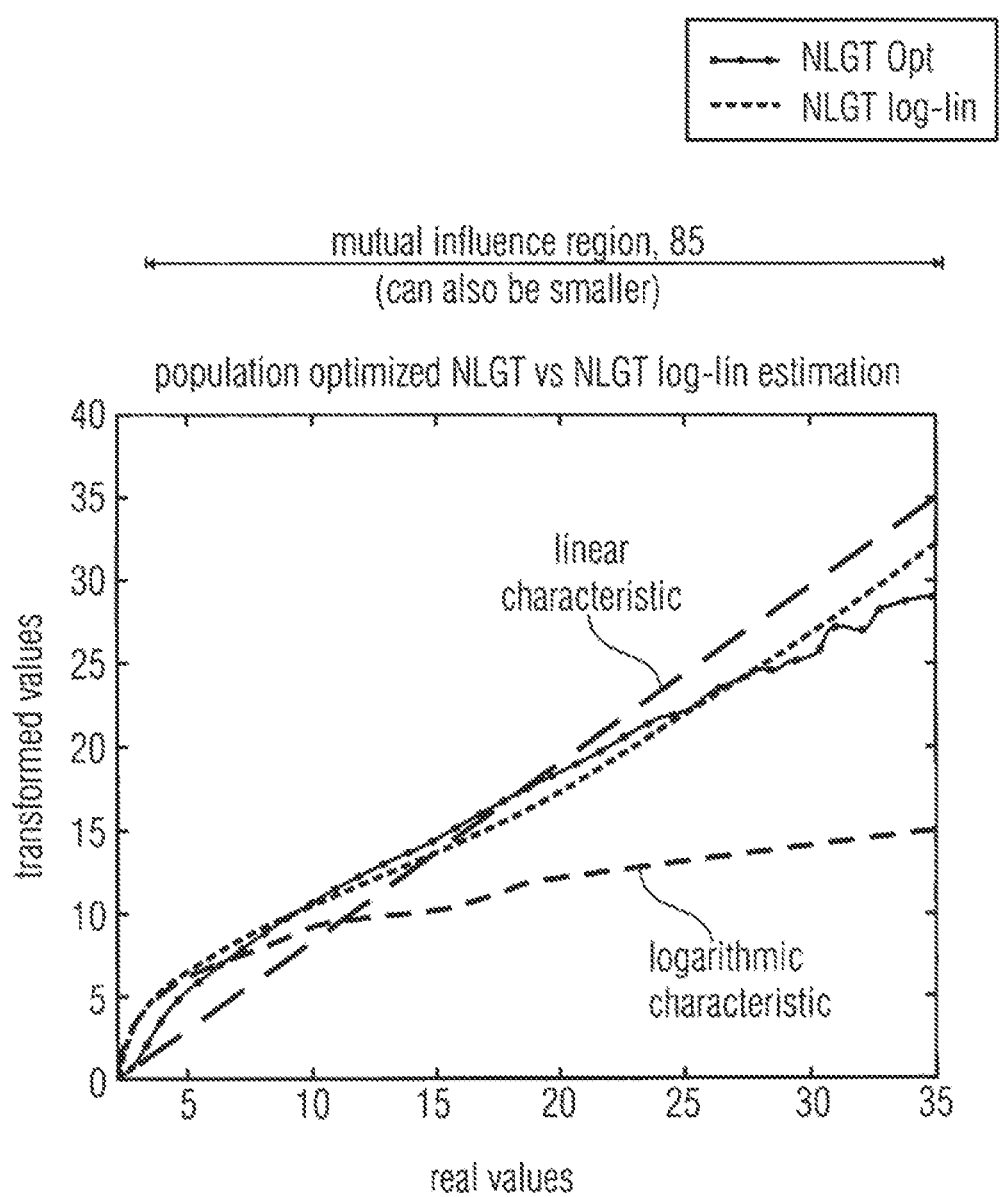
Figure 8D:
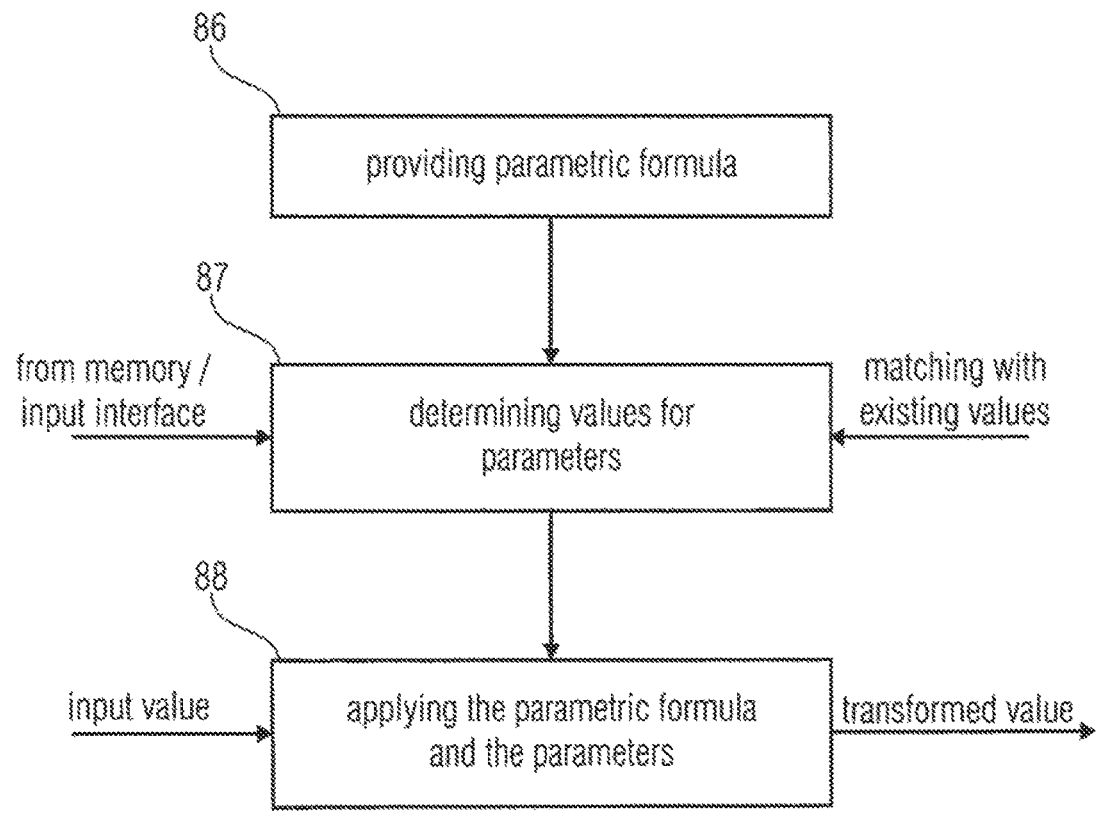
Figure 8E:
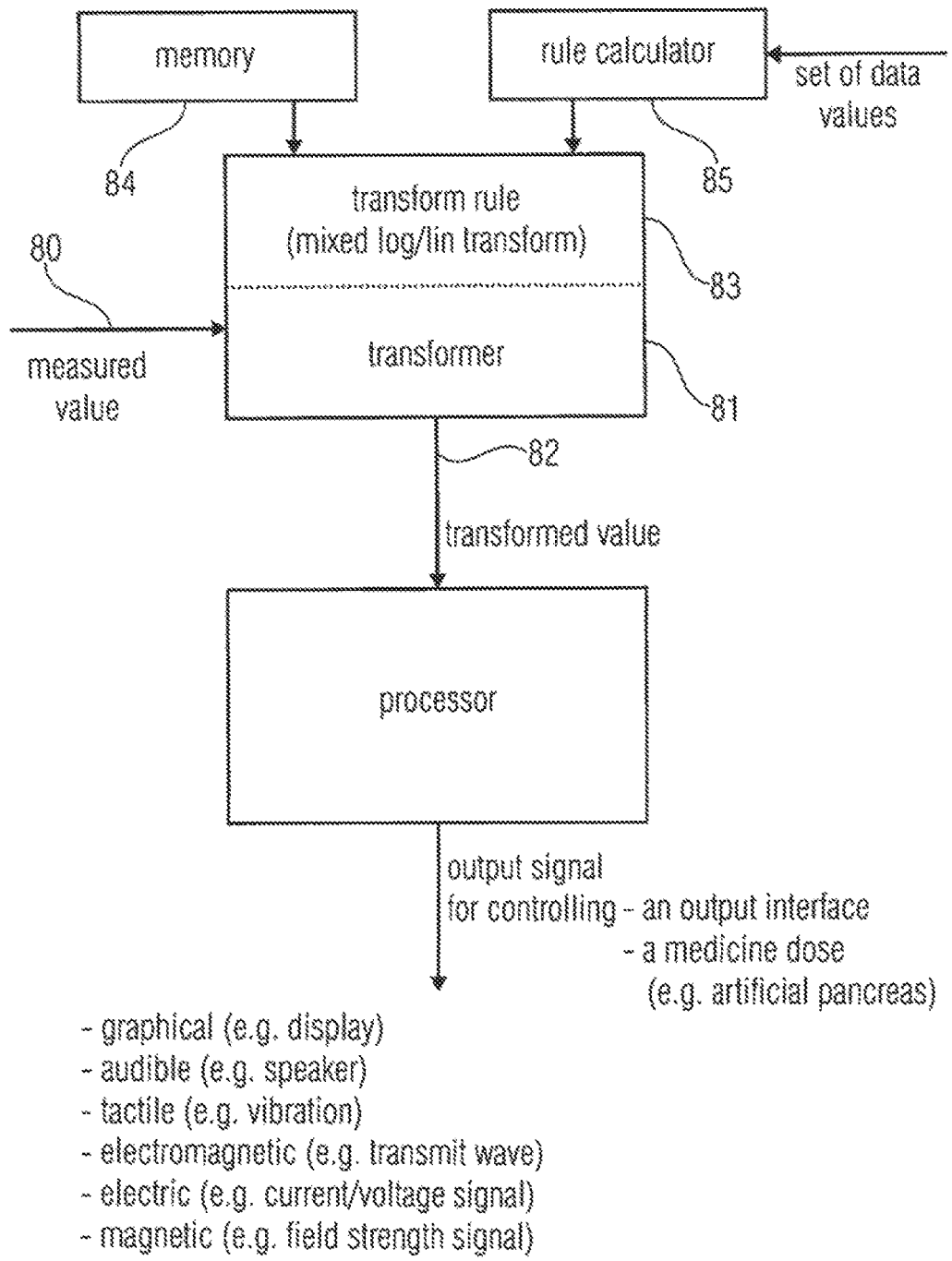

FIG. 8e illustrates an apparatus for processing a glycemic value, where the glycemic value is a measured value 80. The apparatus comprises a transformer 81 for transforming the glycemic value into a transformed glycemic value at the output 82, wherein the transformer 81 is configured for applying a transform rule 83 to the glycemic value, the transform rule 83 comprising a combination of a first logarithmic term comprising a logarithm of the glycemic value, and of a second linear term comprising a linear contribution of the glycemic value, and wherein the transform rule is such that, for each glycemic value of a set of glycemic values having more than one glycemic value, the first logarithmic term and the second linear term both influence the corresponding glycemic value. FIG. 8b illustrates a schematic representation of the transform rule 83. Specifically, the transform rule 83 comprises a logarithmic term contribution 83a, and a linear characteristic or a linear term contribution 83b. Both terms are combined by a combiner characteristic 83c, where each term 83a, 83b can be influenced by an influencer 83d and 83e, so that, dependent on the value of x, the influence of both terms 83a, 83b is different on the finally obtained transformed glycemic value 82. In an implementation, two tuning parameters P, M are used, where the parameter P is a scaler for scaling the logarithmic characteristic, and where the other tuning parameter M controls the influencers 83d, 83e in order to control the actual change from a mostly logarithmic characteristic to a mostly linear characteristic with respect to the values of the input data 80. Specifically, for low values, the influence of the logarithmic characteristic is high and the influence of the linear characteristic is low, but not zero. Analogously, the influence of the logarithmic characteristic for high glycemic values is low, but not zero, and the influence of the linear characteristic is comparatively high. This is illustrated in FIG. 8c, where it becomes clear that the NLGT log/lin illustrated in FIG. 8c is quite close to the logarithmic characteristic at low real values and is quite close to the linear characteristic at high real values. Importantly, there exists a significant mutual influence region which is, advantageously, much higher than the at least two glycemic values. Particularly, the mutual influence region, i.e., the "fade-over" region from the logarithmic to a linear characteristic covers almost the whole range of real values as indicated at 85. Advantageously, the mutual influence region covers at least 50% of the useful range of real values extending from a value of 2 mmol/liter to 35 mmol/liter for glycemic data.

Subsequently, the calculation of the tuning parameters P, M from equation (18) or (20) is illustrated with respect to FIG. 8b. However, it is to be emphasized that other formulas than equation 18 and other and more or less tuning parameters can be applied, as long as the transform rule illustrated in FIG. 8 has a mixed log/lin characteristic, where, advantageously, the logarithmic characteristic is predominantly occurring in the lower value range and the linear characteristic is predominantly occurring at the higher range. In a step 86, a parametric formula is provided such as formula 18 or any other formula which has a considerable range of blending over from a logarithmic characteristic to linear characteristic in a blend-over or fade-over region being larger than 50% of the useful measurement range of the physiological values to be measured. For glycaemic data, the useful measurement range would extend e.g. between 1 and 40 mmol/l in order to cover a bit more than most of the measured values of a typical population.

Values for the parameters are determined as illustrated at 87. The values can be retrieved from a memory or from an input interface which receives a user input or a remote computer input or the like. Alternatively, as illustrated to the right side of block 87, a matching of the transform rule to this existing data can be performed. In this case, different parameters are tried and the distribution of the transformed data is compared with an intended distribution such as a normal distribution. Then, certain tries for different parameters are performed and, for each try, it is determined how well the distribution of the transformed data coincides with the target distribution. Then, the parameters are selected as the used parameters in step 87, which have resulted in the best try result. Then, the parametric formula and the parameters determined in step 87 are applied in step 88 to an input value to finally obtain the transformed value.

Graphical Interpretation

One embodiment of the invention corrects the above described presentation biases in present graphical presentations, thus improving feedback to the patient and increase the beneficial potential of self-treatment, see FIG. 9a. Unlike current, presentations based on normal distributed glucose data, this method can adjust for any size group of individuals averaged distribution, or any single individual's unique distribution. An individualized glucose scale renders several self-care and treatment benefits. The graphic, diagram space will be optimized for the individuals specific glucose dynamics meaning that even mirror—but from a treatment perspective important—glucose concentration changes will not be suppressed but instead shown adequately. For instance, an individualized presentation scale will reveal that a small glucose decrease in the hypoglycemic range will render a more significant physiological impact than a small decrease in the euglycemic range. Using a linear scale for nonlinear glucose data will result in asymmetric data clusters making the interpretation of mean value and variability measures unreliable and possibly even risky. However, a glycemic presentation scale based on the individual's specific distribution shows a symmetrical cluster around the real glucose mean value—improving the interpretation of changes over time. For most patients, where the distribution differs from current presumptions, an adjusted scale will improve the possibility of understanding the correlation and interaction of important influencing factors like food intake, physical activity and medication.

The transform is applicable and can be optimized for one individual or any number of individuals. To some extent, individuals with similar DM state and DM management will have a quite similar glucose distribution. Therefore, it is possible to generate scales for wisely selected populations used for any type of treatment, clinical or research purpose. This is achieved by, using the method described in FIG. 7. For instance when optimizing for one individual, it may be advantageous to choose an, initial glucose scale based on some clinical DM state and statistic characteristics. When sufficient amount of readings have been collected, according to FIG. 3, a new optimized and automatically upgraded personalized scale for the individual user of the device can be obtained. This can be implemented in real-time using a given time window and a suitable data updating algorithm.

A new method according to the invention is introduced for presenting blood glucose data in a symmetrical manner, where the blood glucose identity is preserved and where the individual's physiological condition and unique blood glucose dynamics are captured in an improved way. The proposed invention offers amore indicative and improved utilization of diagram space since the glycemic ranges that is of importance for the individual will be more clearly visible and accentuated in the diagram.

Since arbitrary blood glucose data has an asymmetrical statistical probability density function, where the degree of asymmetry is highly affected by the mean value of the blood glucose data, the above mentioned transform method can be used to symmetrize the data. As target function, $F_{target}(x)$, a normal distribution is selected:

$$F_{target}(x;\mu,\sigma) = \frac{1}{2}\left[1 + \frac{2}{\sqrt{\pi}} \int_0^{\frac{x-\mu}{\sigma\sqrt{2}}} e^{-t^2} dt\right] \quad (21)$$

where $$\mu = \frac{1}{n}\sum_{i=1}^{n} x_i \quad (22)$$

and $$\sigma = \sqrt{\frac{1}{n}\sum_{i=1}^{n}(x_i - \mu)^2} \quad (23)$$

When the blood glucose data has been transformed using the transform, see block 9a in FIG. 9a, it has lost the blood glucose identity for example in mmol/l or mg/dl. By using the same transform, but in reverse on the values of the y-axis and substituting these values by the de-transformed values the blood glucose identity is restored, see block 9c in FIG. 9a. The result of block 9c and 9b in FIG. 9a is depicted in FIG. 10.

The de-transformed y-axis can be designed and constructed to resemble the appearance of the widely used and established linear y-axis—an axis where the tick-marks are evenly spread and the values that correspond to the tick-marks follows a linear and symmetric pattern. This can be obtained by placing the tick-marks evenly with an exact distance on the y-axis with the corresponding values de-transformed and substituted, see FIG. 11a. It can also be accomplished by prioritizing the de-transformed values and placing the tick-marks approximately on equal distance, see FIG. 11b. The de-transformed y-axis can also be designed in a non-linear way with respect to the de-transformed values, see FIG. 11c.

Predictive Alarms and Glucose Dynamics Interpretation

Continuous glucose monitoring devices use predictive alarms and rate of change indicators. Since the outcome of such alarms and indicators is affected by the fact that glucose changes do not follow a linear behavior, a new method for linearizing these changes is presented. Another embodiment of the invention will increase the precision in the predictive alarms and make the rate of change indicators better reflect the health risk related to a blood glucose level change, see FIGS. 12a and 17.

By using knowledge on how the biological and physical restraints affect the behavior of blood glucose dynamics and by using continuously sampled blood glucose data originating from a population, a generic perturbation of blood glucose can be estimated, here denoted $\tilde{Y}_{per}$, see FIG. 13a. The population data from which $\tilde{Y}_{per}$ is estimated can be selected with respect to the intended use of the application, for instance T1DM, T2DM or any combination of populations in general or even optimized on an individual level, i.e. $\tilde{Y}_{per}$ may be continuously and adaptively re-estimated and optimized from real-time patient statistics using appropriate methods. Hence the alarm algorithm can be continuously updated over time to suite the specific user.

By finding a transform that linearizes $\tilde{Y}_{per}$ that transform will approximately linearize blood glucose perturbations derived from a similar population from where $\tilde{Y}_{per}$ was estimated. The design of a such transform can be accomplished by using the fact that a linear equidistant function, by definition, belongs to a uniform distribution. By using the above presented transformation method and defining the target function, $F_{target}(x)$, as a CDF for a uniform distribution as $$F_{target}(x) = \begin{cases} 0, & x < a \\ \frac{x-a}{b-a}, & a \le x < b \\ 1, & x \ge b \end{cases} \quad (24)$$

where a and b is defined by the cumulative distribution function of $\tilde{Y}_{per}$, a transform map or function can be generated by using $\tilde{Y}_{per}$ as input data, see FIG. 3, FIG. 13c and FIG. 13d. Hence, $\tilde{Y}_{per}$ will belong to a uniform distribution after transformation using this transform. By definition, the transformed $\tilde{Y}_{per}$ will now be a linear perturbation. Thus, this transform can be used to approximately linearize the perturbations of glycemic data derived from a similar population from where $\tilde{Y}_{per}$ was estimated.

FIG. 13e illustrates an alternative implementation and determination of the transform rule for linearizing the certain characteristic, i.e., the blood glucose fall characteristic. The actual curve 140 as determined by the procedure illustrated in FIG. 12*a* to FIG. 12*h* would be applied to block 3*b* in FIG. 3 instead of the estimated CDF. Furthermore, a target function is determined as a linear function between two points of the function 140. Advantageously, the highest value 142*a* and the lowest value 142*b* of the estimated actual function 140 are used, but other two points can be used as well, such as the values at 25 mmol/l and κ mmol/l, but this might negatively influence the accuracy of the linearization. Hence, it is advantageous to select the two points 142*a* and 142*b* as far apart as possible to obtain a maximally accurate linearization. The thus determined function 141 of FIG. 13*e* is then used as the target function in FIG. 3 and is input into block 3*b*. Then, the transform rule is calculated/determined as discussed with respect to equation (14). Depending on the implementation, the function 140 can be approximated by a high order polynomial function or can be used as a table. The function 141 is available as an analytical linear function determined by two points 142*a* and 142*b*.

Predictive alarms are commonly used in today's continuous glucometers, and its purpose is to warn the user of future critical blood glucose concentration levels. Therefore it is of utmost importance that these alarms are accurate and trust worthy. By linearizing the blood glucose perturbations, using the above mentioned transform, before the use of classic prediction alarm algorithms, the precision and reliability of such alarms will increase significantly, regardless of prediction algorithm used, the theory is shown in FIG. 14.

A case study consisting of 30 T1DM patients, using continuous glucometers, shows that the mean of precision in the predictive alarms was improved by 21% and the reliability was improved by 36% when using the NLGT-transform, see FIGS. 15 and 16.

Changes in blood glucose levels are often presented, in continuous glucometers and software, as arrows, where fixed pre-determined levels in blood glucose rate of change correspond to a tilt angle of the arrow and thus risk relating to the change. Due to the non-linearities in blood glucose dynamics, current indicators does not show the true risk a given glucose rate of change may impose on an individual. For instance, a blood glucose change in the hypoglycemic area may usually not get adequate attention in the lower range. Small concentration changes may imply severe impact and consequences on the individual's physical and mental state of health. Contrary, in the upper end of the blood glucose range, where long term complications and side effects typically develops exponentially relating to glucose level, small changes in glucose concentration may, from a risk perspective, be suppressed, obscured and not reflected adequately.

In one embodiment the transform can be used for improved rate of change indication, see FIG. 17. By linearizing the blood glucose level changes before calculating the rate of change, small changes in critical areas will offer improved response of the indicators, thus more accurately indicate the true health risk such changes may impose, see FIG. 18.

FIG. 12*d* illustrates an apparatus for generating a condition indication in accordance with the further aspect of the invention. The apparatus receives, as an input, a time sequence of data values 130 and outputs the condition indication at an output 131. In the time sequence of data values, each data value represents a physiological measure of a condition of a subject at a time. The time sequence of data values can, for example, be a certain portion of a blood glucose concentration of a human being over time as generated by a continuous glucose metering device. Specifically, the time sequence of data values can represent a certain specified characteristic such as a blood glucose fall or a blood glucose rise, but other physiological measures can be processed using the apparatus in FIG. 12*d* as well. The apparatus for generating the condition indication comprises a transformer 132 for transforming the time sequence of data values into a transformed sequence of data values using a transform rule 133, wherein the transform rule is such that a certain characteristic in a time-course of the physiological measure represented by the transform sequence of data values is more linear than the time course before the transform. Specifically, the certain characteristic is a blood glucose fall as illustrated in FIG. 13*a*.

The output of the transformer 132 is a sequence of transformed values 134, where the sequence of transformed values is input into a rate of change calculator 135 for calculating an estimated rate of change for the transform sequence of data values. The rate of change calculated in the transform domain on line 136 is input into a processor 137, where the processor is configured for processing the estimated rate of change to output the condition indication 131. Specifically, the processor 137 is configured for generating a graphical, audible or tactile display of the estimated rate of change or for generating an electrical, magnetic or electromagnetic signal representing the estimated rate of change. The display can be similar to FIG. 18, where the rate of change is graphically illustrated via an arrow. Alternatively, an audible indication would be, for example, a certain tone/frequency for a certain rate of change where a higher tone could correspond to a higher rate of change and vice versa. Alternatively, the repeat frequency of an audible tone could be adjusted depending on the rate of change value. Regarding a tactile tile display, depending on the rate of change, the higher or lower vibration frequency could, for example, be used. Regarding an electromagnetic indication, reference is made to an implementation where the processor is a telemetry processor which does not include in itself a display or an audible or tactile output. Instead, the processor would be implemented to transmit a wireless data signal or a wired data signal to a remote device for display or any other way of processing on the remote device. Regarding an electric condition indication, reference is made to an implementation, where the processor is a driver for driving an output amplifier which is connected to a wire, and where this wire is connected to a receiver at a remote location. Then, the processor would generate and output the electric signal such as a current signal or a voltage signal. Similarly, a magnetic signal could be generated representing the condition indication, for example, for being transmitted to a remote receiver. The above described processing operation of values can also be applied to all other values generated by the different aspects of the invention.

The transform rule provided to the transformer 133 can be actually calculated as discussed in connection with FIG. 3 or can be stored on the look-up table as discussed in the context of FIG. 9*b* or can be implemented as a parameterized function as generated, for example, by the procedure illustrated in FIG. 8*d* or as illustrated at 95 in FIG. 9*b*. The transform rule applied by the transformer is, however, a transformer which is different from the transform rule applied for the purpose of obtaining a normal distribution. Instead, the transform rule is so that a uniform probability density function for a blood glucose dynamic is obtained which corresponds to the linearly increasing target function. This linearly increasing target function is illustrated in FIG. 13*c*.

Starting point for calculating the transform rule is the certain characteristic which is to be linearized. FIG. 13a illustrates, as an example for the certain characteristic, data on a blood glucose fall. Subsequently, this aspect will be discussed in the context of FIG. 12h. FIG. 12h illustrates a similar illustration as FIG. 13a, but, in contrast to FIG. 13a, where 105 divisions of the value range (y axis) have been performed, there will exist only five divisions in FIG. 12h for a better understanding.

The first division extends from value 0 to value 5. The second division extends from value 5 to value 10, the third division extends from value 10 to value 15, the fourth division extends from value 15 to value 20 and the fifth division extends from value 20 to value 25.

Additionally, raw sample values having the certain characteristics such as a fall have to be selected from a general set of measurement data having the certain characteristic and other characteristics as indicated at 121 in FIG. 12b. A measurement data set can be, for example, a blood glucose development of a plurality of patients such as 30 patients over a period of days or so. It is to be emphasized that the data for FIG. 13a can be obtained from an individual person or can be selected from a collection of data from many persons.

Each selected measurement data will comprise a blood glucose rise or a blood glucose fall, where the blood glucose falls will extend over a certain range such as from a value of 30 to a value of 1 in a first instance, from a value of 10 to a value of 5 in a second instance, from a value of 20 to a value of 5 in a third instance, from a value of 25 to a value of 15 in a fourth instance or from a value of 50 to a value of 7, for example, in a fifth instance.

In accordance with step 122 of FIG. 12b, the y axis is divided into the plurality of, for example, five regions as discussed. Then, in step 123, for each region of the exemplary five regions, an average rate of change or a "fall speed or rise speed" is calculated. This is done by looking at which of the selected "raw" data falls contribute to the certain value range. For example, for the value region from 25 to 20, two data instances contribute. Now the average rate of change between these two data instances is calculated and a linear function 124a is introduced into the figure at an arbitrarily selected time $t_1$ which can also be the zero time, where the y shift is defined by the value of 25 where the value region starts. Depending on the rate of change, the time $t_2$ is close to $t_1$ (for a high rate of change) or is further apart from $t_1$ for a lower rate of change.

Then, the same procedure is done for the second region from 20 to 15. Particularly, an average rate of change for this region using the available data instance is calculated and a further linear function is added to the end of the function 124a, where the further linear function is indicated as 124b. The same procedure is done for a third averaged high rate of change for the region between 10 and 15, which receives the further linear function 124c. Similar linear functions are introduced in the remaining two regions which are indicated as 124d and 124e. Thus, a "characteristic" dynamic behavior curve is built from the average rates of change as indicated at step 125 in FIG. 12b. FIG. 12b has a characteristic curve consisting of piece wise linear sections 124a to 124d, and it is advantageous to smooth this curve as indicated at 126 in FIG. 12b. However, the smoothing is, in a sense, automatically obtained, when the value regions are made smaller so that many different value regions are processed which was the case for the generation of the data in FIG. 13a where the y axis was separated into 105 value regions.

In step 127 in FIG. 12c, the probability function for the dynamic behavior curve illustrated in 5. FIG. 12h or 13a is calculated. Specifically, a high rate of change will result in a low probability density function or a low rate of change will result in a high probability density function. This means, for the example in FIG. 12h that a minimum PDF will be in the value range between 10 and 15 and a maximum PDF will be obtained in the value range between 20 and 25. Specifically, the probability density function for the dynamic behavior curve indicates the probability that a certain blood glucose value occurs in a fall/rise and, particularly, in a certain region. In this context, reference is made to FIG. 13b illustrating an estimation of a PDF for the blood glucose dynamics illustrated in FIG. 13a, where the individual normal distributions calculated per each region are obtained in the same manner as has already been discussed for the embodiment in FIG. 4a.

When the PDF for the blood glucose dynamics or the specific characteristic in FIG. 13a has been calculated, a target probability function is selected as indicated at 128 in FIG. 12c. In this embodiment, the target probability function is an equal probability that a blood glucose value occurs in a curve for all blood glucose values. Stated differently, the probability density function is a constant line over the range of blood glucose values. The cumulative distribution function CDF which is the integral over the probability density function is, therefore, the linearly increasing cumulative distribution function illustrated in FIG. 13c indicated as the target function. Then, in step 129, the transform rule is calculated in the same manner as has been discussed in the context of equation 14. Then, in step 130, the transform rule is stored as a look-up table or as a set of parameters. The transform rule or transform map belonging to the example in FIG. 13a is illustrated in FIG. 13d.

Subsequently, further embodiments of the rate of change calculator 135 in FIG. 12d are discussed in the context of FIG. 12e. Specifically, the rate of change calculator comprises means for calculating a difference between two transformed values indicated at 135a and means for determining the time coordinates associated with the transformed values indicated at 135b. Specifically, when FIG. 16 is considered, where FIG. 16 is a transformed representation of FIG. 13a, it becomes clear that the transformed value corresponding to the non-transformed value of about 6.8 corresponds to time $t_A$ of about 2 minutes, and the transformed value corresponding to the non-transformed value of about 6.2 mmol/l corresponds to a time $t_B$ where $t_B$ is about 6 minutes. Based on these two values $t_A$, $t_B$, a time difference data $\Delta t$ is calculated. Then, in a means 135d, the rate of change is calculated as the $\Delta BG_t$ divided by $\Delta t$.

The calculated rate of change ROC is then forwarded to the processor 137. In a further implementation of the present invention, the processor 137 corresponding to or comprising the display device 17c in FIG. 17 can be implemented as outlined in FIG. 12f. Specifically, the processor can be implemented for calculating (137a) an intersection point between the linear fall determined by the rate of change obtained by the rate of change calculator and the transformed risk level which is obtained by a step of transforming 137b the risk level using the transform rule. The transformed risk level is indicated in FIG. 16 at 16. The intersection point IP has a time coordinate around 25 minutes, but the time coordinate which is more interesting is the time difference between the last calculated blood glucose value corresponding to real value of 4. Hence, an indication of the predicted alarm time would indicate, in FIG. 16, a time of 25 minutes minus 6 minutes corresponding to about 19 minutes. Hence, an alarm could be that the user is warned that he will reach a critical state in about 19 minutes, and this warning message could be interpreted by the user in such a way that the user starts to eat sugar or sugar-containing nutrition in order to make sure that he will counteract to his blood glucose fall. Alternatively, as indicated at 137c, a comparison with a time period such as a critical time period can be performed so that the user is only warned when the actually calculated time period of, for example, 19 minutes in this example is below the comparison time period. This function can be performed alternatively to the output indication of the predicted alarm time or in addition thereto.

A further implementation illustrated in FIG. 12g for the processor 137 is based on a transformed risk level 137b. Additionally, the processor is configured for calculating a predicted value in a predetermined time distance using the rate of change and a transformed value where the rate of change is, for example, calculated by block 135 in FIG. 12d or is calculated as determined in FIG. 12e. To this end, for example the last transformed value corresponding to a real value of 6.2 mmol/l is, used and a predetermined time distance of, for example, 10 minutes is applied. Then, a predicted value based on the rate of change is calculated for a time distance of 22 minutes which would correspond, in FIG. 16, to the time of 29 minutes indicated at $t_C$. Then, a predicted value of about 3 mmol/l is calculated and the predicted value is compared to the transformed threshold as indicated at 137e. Then, an output alarm message would be generated as indicated at 137f depending on the result of the comparison. In the example discussed in connection with FIG. 16, the transformed value at time $t_C$ is lower than the transformed alarm threshold 16 so that an output message would be generated.

It is to be noted that higher order or more advanced predictors apart from linear predictors can be applied as well, but linear predictors may be advantageous due to their simple and intuitive implementation.

Estimation of Central Tendency

In diagnosis, classification and treatment of various types and stages of diabetes and pre-diabetes it is of great importance to observe how both the mean value and the variability of the glucose concentration changes with different treatment strategies. An accurate estimate of the mean value has a strong correlation to the clinical risk measure HbA1c, the long term glycemic measure, which is currently the most recognized indicator for glycemic control. Hence, the mean value estimation from glucometer readings provides continuous feedback relating to long term risk to the patient. In addition, it has become more common to use the standard deviation of glycemic data to bring another dimension to the classification of blood glucose control. For the mean value and standard deviation to provide the intended aid in diagnosis, classification and treatment, it is of great importance that the presented values are correct and accurate. Measurements by means of glucometers imply high running costs. It is therefore desirable to obtain correct mean values and variability estimates with as few glucometer readings as possible.

When estimating the mean value, or central tendency, of a variable from observations it is important to know the underlying distribution from where the observations originate. Depending on the underlying distribution of the observations, different methods will perform more or less well. When evaluating statistical estimation methods, mainly two parameters are taken into account: Robustness and efficiency. Robustness refers to how the method is affected by skewness of the distribution and outliers. Efficiency is a measure of how the variance of the estimator depends on the number of readings or samples used in the point estimation.

Estimation of central tendency of glycemic data, by means of an arithmetic sample mean, is a widely used method to classify patients and evaluate treatment methods. However, this method does not take into consideration that the distribution of glycemic data is unknown, individual and often skewed. The arithmetic sample mean is not robust and therefore highly affected by skewed distributions and outliers. A more robust standard method is the sample median. However, this method suffers from low efficiency which means that many samples are needed to reduce the variance of the estimate.

As mentioned, glycemic data has different distributions depending on glucose control, treatment regimen and how the earlier mentioned biological boundaries affects blood glucose dynamics. In one embodiment of the invention, the transform is utilized for generating an mean value estimation method, see FIG. 19, that is substantially less sensitive to different shapes of the distribution, i.e. more robust, than the arithmetic mean, yet still effective to reduce the variance in the estimate. Let $$X[n] = \mathcal{F}_N(x[n]) \tag{25}$$

denote the transformation of data x into X, using a normal distribution as the target function, $F_{target}(x_t)$, for the transform. The corresponding inverse transform is written as $$x[n] = \mathcal{F}_N^{-1}(X[n]) \tag{26}$$

The robust, NLGT-mean estimator of central tendency is now given by $$\bar{x}_{NLGT} = \mathcal{F}_N^{-1}\left(\frac{1}{n}\sum_{i=1}^{n} \mathcal{F}_N(x_i)\right) \tag{27}$$

This functionality is illustrated in block 19a, 19b and 19c in FIG. 19. Hence, this estimator is an arithmetic mean in the transform domain, i.e. the arithmetic mean for a normally distributed variable. It will be as robust as the median value since the transform will make the data normally distributed if the transform goal is set to a normal distribution. However, it can also be shown that the NLGT-mean estimator is a substantially more efficient estimator than the median. One commonly used measure to compare the efficiency of two methods is the asymptotic relative efficiency, ARE. The ARE represents the ratio between the number of samples at which the result of the two estimation methods have the same variance.

It can be shown that the variance of the arithmetic mean estimation from $n_1$ samples drawn from a normal distribution is given by $$\sigma_{\tilde{x}}^2 = \frac{\sigma^2}{n_1} \tag{28}$$

where $\sigma^2$ is the variance of the normal distribution. Further, it can be shown that the variance of the median given $n_2$ samples from an arbitrary distribution is $$\sigma_{\tilde{x}}^2 = \frac{1}{4n_2[f(\theta)]^2} \tag{29}$$

where f(..) is the probability distribution function of the variable and θ is the true median, x. ARE between the arithmetic mean for normally distributed data and the median for arbitrary distributed data is now defined as $$\sigma_{\bar{x}}^2 = \sigma_{\tilde{x}}^2 \Rightarrow \frac{\sigma^2}{n_1} = \frac{1}{4n_2[f(\theta)]^2} \Rightarrow \frac{n_1}{n_2} = 4\sigma^2[f(\theta)]^2 = ARE \quad (30)$$

Since f(θ) is unknown and different for every diabetic, real data from the DCCT-study was used to prove that the NLGT-mean estimator is a more efficient estimator than the median. From the DCCT-study, datasets with over 180 samples where studied to ensure statistic reliability. That gave over 500 datasets with varying mean values and shapes of f(..). For each dataset ARE was calculated, the results are depicted in FIG. 20. It is obvious that ARE has a value less than 1 and most commonly a value around 0.5-0.6 using the NLGT. This means that the NLGT-mean estimator only needs around half as many samples as the median to produce an estimate with the same variance. FIGS. 21 and 22 (zoomed) shows that the NLGT-mean estimator produces estimates around the median. The deviations from the median are a result of the NLGT-means better efficiency, i.e. less deviation from the expected value. The FIGS. 21 and 22 also show that the arithmetic mean is less robust and deviates from the median and NLGT-mean. Especially for datasets with low mean and a highly skewed f(..), the deviation of the arithmetic mean from the robust estimators is often around 15-20%.

Estimation of Variability

When evaluating a patient's ability to reach good glucose control it is of great importance to analyze how stable or unstable the individuals glucose concentration is over time. A commonly used risk measure of glucose control and glucose stability is the standard deviation. The standard deviation for a dataset, $[x_1, x_2, \ldots, x_n]$, is given by $$\sigma = \sqrt{\frac{1}{N}\sum_{i=1}^{n}(x_i - \mu)^2} \quad (31)$$

and presents the average deviation from the mean value, μ. This mean value is estimated as an arithmetic mean value of the data. Hence, the calculation of the standard deviation depends on the arithmetic mean that is a non-robust estimator that will be highly affected by the distribution of the data. Since the distribution for glycemic data is unknown and often skewed the standard deviation will be in error due to errors in μ. Further, the standard deviation describes both the deviations over and under the mean value as a single value, thus necessitates non-skewed data for a correct result. For data with skewed distributions it is obvious that the deviation over and under the mean value will differ. Hence, the standard deviation, that is an established measure of glucose control, suffers from the above mentioned two major drawbacks.

By using the robust, efficient NLGT-mean estimator according to the invention, the NLGT-standard-deviation is defined as $$\sigma_{NLGT} = \sqrt{\frac{1}{N}\sum_{i=1}^{n}(x_i - \bar{x}_{NLGT})^2} \quad (32)$$

For any shape of the distribution, the NLGT-standard deviation will represent the mean deviation from the correct mean value. However, the problem with the different size of the deviations over and under the mean value still exists. By splitting the standard deviation into two separate values, upside and downside standard deviation, this problem is eliminated. The upside and downside NLGT-standard deviation is now defined as $$\sigma_{NLGT}^U = \sqrt{\frac{1}{N}\sum_{i=1}^{n}(x_i - \bar{x}_{NLGT})^2}, x > \bar{x}_{NLGT} \quad (33)$$

$$\sigma_{NLGT}^D = \sqrt{\frac{1}{N}\sum_{i=1}^{n}(x_i - \bar{x}_{NLGT})^2}, x < \bar{x}_{NLGT} \quad (34)$$

see block 19d in FIG. 19. A normalized variation and risk measure according to the invention is made available by defining the NLGT-Upside Coefficient of Variation ($UCV_{NLGT}$) and NLGT-downside Coefficient of Variation ($DCV_{NLGT}$). Given the $\sigma_{NLGT}^U$ and $\sigma_{NLGT}^D$ the $UCV_{NLGT}$ and $DCV_{NLGT}$ can be defined as $$UCV_{NLGT} = \frac{\sigma_{NLGT}^U}{\bar{x}_{NLGT}} \quad (35)$$

$$DCV_{NLGT} = \frac{\sigma_{NLGT}^D}{\bar{x}_{NLGT}} \quad (36)$$

This is represented in block 19e in FIG. 19.

Together, the upside and downside NLGT-standard deviation will provide accurate indicators of the glucose deviations around the true mean, and together with $UCV_{NLGT}$ and $DCV_{NLGT}$ form new and improved risk measures. These new measures will help making diagnosis, classification, self-care and treatment easier and more accurate.

The apparatus for processing a set of data values in accordance with the aspect illustrated in FIG. 3 further comprises, in an embodiment, a mean value calculator 25b or 19b for calculating a transformed mean value for the plurality of transformed values of the set. Furthermore, an inverse transformer 19c for inverse transforming the transformed mean value to a back-transformed mean value is provided, where the inverse transformer is configured for using an inverse transform rule. Furthermore, a processor such as a display device 19f or any other device for using the back-transform mean value is provided for generating an audible, visual, tactile, mechanical, electro or magnetic indication thereof.

Additionally, or alternatively, a standard deviation calculator 25d or 19d is configured for calculating an upper standard deviation USD for a non-transformed value greater than the back-transformed (inversely transformed) mean value or for calculating a lower standard deviation (DSD) for non-transformed values lower than the back-transformed mean values provided, where the processor 25i or 19f is again configured for generating an audible, visual, tactile, mechanical, electrical or magnetic indication derived from the upper standard deviation or the lower standard deviation. Alternatively, an upper coefficient of variation or a downside coefficient of variation (DCV) can be calculated in accordance with equations 35 and 36 as illustrated at 25e or 19e.

Elaborate System

By combining the above described embodiments, an elaborate device according to FIG. 25 is obtained intended for precise and accurate monitoring, display and interpretation of glucose data in a new and improved way, heretofore not possible using conventional methods.

Artificial Pancreas

The artificial pancreas is a promising technology that mimics endocrine function of a healthy pancreas. It uses an insulin pump under closed loop or semi-closed loop control using real-time data from a blood glucose sensor, see FIG. 23. Depending on the complexity of the artificial pancreas, additional inputs and outputs may exist as well as more advanced regulators.

Regardless of complexity, the desired glucose set-point is input into the artificial pancreas as well as the actual metabolic glucose level. In a simplified artificial pancreas, as the one shown in FIG. 23, a PID regulator is used. This type of regulator processes the difference between the two glucose levels, and sends a control signal to an insulin pump to adjust the insulin dosage in order to meet the insulin requirement.

Traditionally these glucose level signals are processed in a linear fashion, meaning that the same control signals are being sent to the insulin pump regardless of the absolute actual glucose level as long as the BG error signal level is the same.

However in yet another embodiment of the invention, the NLGT transform is applied on the set-point reference and the actual glucose level, as shown in FIG. 24. This will increase the error signal when the actual glucose level is in the hypo- or hyperglycemic range. This in turn gives a stronger response by the regulator at these critical ranges compared to a regulator having non-transformed glucose levels. For example, when the actual glucose level is decreasing when in the hypoglycemic range, the insulin pump infusion rate will decrease (or completely stop) faster when the NLGT transform is used. When the actual glucose level is in the hyperglycemic range, the infusion rate will increase faster when applying the NLGT transform. Thus, the NLGT transform improves regulation and control of the artificial pancreas.

The artificial pancreas comprises a controller having a feed-forward portion consisting of items 24b, 24d and a combiner connected to the input of 24b for combining a result from the feedback portion 24e, 24f and the reference value to obtain an input for the feed-forward portion. Specifically, the transformer 3c of FIG. 3 is configured for transforming the reference value and the feedback value using the transform rule, where the combiner is configured for combining the transformed value generated by the transformer. An implemented combination rule is that the feed-transformed feedback value is subtracted from the transformed reference value.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Depending on certain implementation requirements, embodiments of the invention can be implemented, in hardware or in software. The implementation can be performed using a digital storage medium, for example a floppy disk, a DVD, a CD, a ROM, a PROM, an EPROM, an EEPROM or a FLASH memory, having electronically readable control signals stored thereon, which cooperate (or are capable of cooperating) with a programmable computer system such that the respective method is performed.

Some embodiments according to the invention comprise a non-transitory or tangible data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine readable carrier.

Other embodiments comprise the computer program for performing one of the methods described herein, stored on a machine readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein.

A further embodiment of the inventive method is, therefore, a data stream or a sequence of signals representing the computer program for performing one of the methods described herein. The data stream or the sequence of signals may for example be configured to be transferred via a data communication connection, for example via the Internet.

A further embodiment comprises a processing means, for example a computer, or a programmable logic device, configured to or adapted to perform one of the methods described herein.

A further embodiment comprises a computer having installed thereon the computer program for performing one of the methods described herein.

In some embodiments, a programmable logic device (for example a field programmable gate array) may be used to perform some or all of the functionalities of the methods described herein. In some embodiments, a field programmable gate array may cooperate with a microprocessor in order to perform one of the methods, described herein. Generally, the methods are advantageously performed by any hardware apparatus.

The above described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

While this invention has been described in terms of several embodiments, there are alterations, permutations, and equivalents which, fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for processing a set of data values, a data value representing a physiological measure of a body fluid at a time instant, wherein the physiological measure is a blood glucose value, comprising:
- an estimated probability function calculator for calculating an estimated probability function associated with the set of data values;
- a transform calculator for calculating a non-linear transform rule using a predetermined target probability function being different from the estimated probability function and using the estimated probability function associated with the set of data values, so that the probability function of a set of transform data values is closer to the target probability function than the estimated probability function;
- a transformer for applying the transform rule to the set of data values or to at least one further data value not comprised by the set of data values and sampled at the different time instant from the time instants for the set of data values to acquire at least one transformed value representing the physiological measure; and
- a device for using the at least one transformed value for controlling a device for dosing a medicament in a closed or open loop configuration or for generating a visual, audible, tactile, mechanical, electro or magnetic indication of a medical characteristic of the body from which the set of data values or the further data value have been taken;
- wherein the transform calculator is configured for using a cumulative distribution function (CDF) as the target probability function, and in which the estimated probability function calculator is configured for calculating the CDF as the estimated probability function,
- wherein the transform calculator is configured for calculating a function value of the estimated CDF for an actual data value and for finding a transformed value, wherein the transformed value is selected by the transform calculator so that the function value of the estimated CDF is equal to the function value of the target CDF; and
- wherein at least one of the estimated probability function calculator, the transform calculator, and the transformer comprises a hardware implementation.

2. The apparatus in accordance with claim 1, in which the transform calculator is configured for using a constant probability distribution over a defined value range as the target probability function, and
- in which the apparatus further comprises an alarm indicator for indicating an alarm state when the transformed further data value exceeds a maximum transformed threshold or is below a minimum transformed threshold, or
- in which the apparatus further comprises an inverse transformer for transforming the transformed further data value into a non-transformed domain, and wherein the alarm indicator is configured for generating an alarm when the inverse transform data value exceeds a maximum threshold or is below a minimum threshold.

3. The apparatus in accordance with claim 1, in which the estimated probability function calculator is configured for calculating a plurality of k normal distributions for a plurality of k bins, where each bin represents a value range, and wherein adjacent bins overlap each other, so that, for each bin, a Gaussian normal distribution is calculated using values in the corresponding bins, and wherein the estimated probability function calculator is configured for calculating weights for each bin, so that an integral over the sum of the k weighted normal distributions results in unity, wherein k is an integer greater than 2.

4. The apparatus in accordance with claim 3, in which the estimated probability function calculator is configured for calculating an estimated cumulative distribution function as a weighted sum of normal distributions.

5. The apparatus in accordance with claim 1, in which the transformer is configured for storing a plurality of non-transformed values and, for each non-transformed value, an associated transformed value, and
- in which the transformer comprises an interpolator for interpolating the further value or a data value not coinciding with a stored, non-transformed value using at least one stored transformed value associated with a stored non-transformed value being closest in value to the further value or the data value and using an interpolation rule.

6. The apparatus in accordance with claim 1, further comprising a mean value calculator for calculating a transformed mean value for the plurality of a transformed values of the set;
- an inverse transformer for inverse transforming the transformed mean value to a back-transformed mean value using an inverse transform rule; and
- a processor for using the back-transformed mean value for generating an audible, visual, tactile, mechanical, electric or magnetic indication thereof.

7. The apparatus in accordance with claim 1, further comprising:
- a mean value calculator for calculating a transformed mean value for the plurality of transformed values of the set;
- an inverse transformer for inverse transforming the transformed mean value to a back-transformed mean value using an inverse transform rule; and
- a standard deviation calculator for calculating an upper standard deviation (USD) for a non-transformed value greater than the back-transformed mean value or for calculating a lower standard deviation (DSD) for a non-transformed value lower than the back-transformed mean value, or upper coefficient of variation (UCV) for a non-transformed value greater than the back-transformed mean value or for calculating a lower coefficient of variation (DCV) for a non-transformed value lower than the back-transformed mean value, or for calculating a regular standard deviation; and
- a processor for generating an audible, visual, tactile, mechanical, electrical or magnetic indication derived from the upper standard deviation or the lower standard deviation or the regular standard deviation or UCV or DCV.

8. The apparatus in accordance with claim 1, further comprising a controller comprising a feed-forward portion, a feedback portion and a combiner for combining a result from the feedback portion and a reference value to acquire an input for the feed-forward portion,
- wherein the transformer comprises a first transformer for transforming the reference value using the transform rule and a second transformer for transforming the feedback value using the transform rule, and wherein the combiner is configured for combining the transformed values generated by the first and second transformers, and
- wherein an output of the first transformer is connected to a first input of the combiner, wherein the second transformer is comprised by the feedback portion, and wherein an output of the second transformer is connected to a second input of the combiner.

9. The apparatus in accordance with claim 1, in which the physiological measure is a glycemic measure and the data values are glycemic data values.

10. The apparatus in accordance with claim 1, in which the transformer is configured for storing the transform rule in a look-up table and in which the apparatus is configured for re-calculating a new transform rule in accordance with an event, the event comprising:
a user input, a timer expiration, a probability control check resulting in a deviation above a deviation threshold of the estimated probability function for an actual set of values and an earlier probability function of an earlier set of values on which the stored transform rule is based, or a randomly-generated event,
wherein the apparatus is configured to re-calculate the new transform rule and to store the new transform rule for usage by the transformer in response to the event.

11. The apparatus in accordance with claim 1, in which the probability function is a probability density function (PDF), a cumulative distribution function (CDF) or a similar probability-related function.

12. A method of processing a set of data values, a data value representing a physiological measure of a body fluid at a time instant, wherein the physiological measure is a blood glucose value, comprising:
calculating an estimated probability function associated with the set of data values;
calculating a non-linear transform rule using a predetermined target probability function being different from the estimated probability function and using the estimated probability function associated with the set of data values, so that the probability function of a set of transform data values is closer to the target probability function than the estimated probability function;
applying the transform rule to the set of data values or to at least one further data value not comprised by the set of data values and sampled at the different time instant from the time instants for the set of data values to obtain at least one transformed value representing the physiological measure; and
using, by a device, the at least one transformed value for controlling a device for dosing a medicament in a closed or open loop configuration or for generating a visual, audible, tactile, mechanical, electro or magnetic indication of a medical characteristic of the body from which the set of data values or the further data value have been taken;
wherein the non-linear transform rule is calculated using a cumulative distribution function (CDF) as the target probability function, and wherein the CDF is calculated as the estimated probability function, and
wherein a function value of the estimated CDF is calculated for an actual data value, and wherein the transformed value is selected so that the function value of the estimated CDF is equal to the function value of the target CDF.

13. A non-transitory computer-readable storage medium having stored thereon a computer program comprising a program code for performing, when running on a computer or a processor, the method of processing a set of data values, a data value representing a physiological measure of a body fluid at a time instant, wherein the physiological measure is a blood glucose value, said method comprising:
calculating an estimated probability function associated with the set of data values;
calculating a non-linear transform rule using a predetermined target probability function being different from the estimated probability function and using the estimated probability function associated with the set of data values, so that the probability function of a set of transform data values is closer to the target probability function than the estimated probability function;
applying the transform rule to the set of data values or to at least one further data value not comprised by the set of data values and sampled at the different time instant from the time instants for the set of data values to acquire at least one transformed value representing the physiological measure; and
causing a device to use the at least one transformed value for controlling a device for dosing a medicament in a closed or open loop configuration or for generating a visual, audible, tactile, mechanical, electro or magnetic indication of a medical characteristic of the body from which the set of data values or the further data value have been taken;
wherein the non-linear transform rule is calculated using a cumulative distribution function (CDF) as the target probability function, and wherein the CDF is calculated as the estimated probability function, and
wherein a function value of the estimated CDF is calculated for an actual data value, and wherein the transformed value is selected so that the function value of the estimated CDF is equal to the function value of the target CDF.

* * * * *